(12) United States Patent
Jackson et al.

(10) Patent No.: US 7,811,787 B2
(45) Date of Patent: Oct. 12, 2010

(54) POLYNUCLEOTIDES ENCODING HUMAN SLAP-2 VARIANT, HSLAP-2V3

(75) Inventors: Donald G. Jackson, Lawrenceville, NJ (US); Stanley R. Krystek, Jr., Ringoes, NJ (US); Donna A. Bassolino, Hamilton, NJ (US); Rolf-Peter Ryseck, Ewing, NJ (US); Thomas C. Nelson, Lawrenceville, NJ (US); Gena S. Whitney, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 160 days.

(21) Appl. No.: 11/789,322

(22) Filed: Apr. 24, 2007

(65) Prior Publication Data

US 2007/0264662 A1 Nov. 15, 2007

Related U.S. Application Data

(60) Provisional application No. 60/794,630, filed on Apr. 25, 2006.

(51) Int. Cl.
*C12P 21/06* (2006.01)
*C12N 15/00* (2006.01)
*C12N 5/02* (2006.01)
*C12N 1/20* (2006.01)
*C07H 21/04* (2006.01)

(52) U.S. Cl. .................. 435/69.1; 435/320.1; 435/325; 435/252.3; 435/254.11; 536/23.1; 536/23.4; 536/23.5; 536/24.3; 536/24.31

(58) Field of Classification Search ........................ None
See application file for complete search history.

(56) References Cited

U.S. PATENT DOCUMENTS

| | | | |
|---|---|---|---|
| 6,989,232 B2 | 1/2006 | Burgess et al. | |
| 7,101,686 B1 | 9/2006 | Chang et al. | |
| 2004/0171537 A1 | 9/2004 | McGlade et al. | |
| 2005/0118625 A1 | 6/2005 | Mounts | |
| 2005/0196754 A1 | 9/2005 | Drmanac et al. | |
| 2006/0193858 A1 | 8/2006 | Chang et al. | |
| 2007/0048301 A1 | 3/2007 | Bodary-Winter et al. | |
| 2007/0083334 A1 | 4/2007 | Mintz et al. | |
| 2007/0264662 A1 | 11/2007 | Jackson et al. | |
| 2008/0050393 A1 | 2/2008 | Tang et al. | |

FOREIGN PATENT DOCUMENTS

| | | |
|---|---|---|
| JP | 2003250556 | 9/2003 |
| JP | 2003259877 | 9/2003 |
| WO | WO00/58473 A2 | 10/2000 |
| WO | WO02/42452 A2 | 5/2002 |
| WO | WO02/42457 A1 | 5/2002 |
| WO | WO02/055707 A2 | 7/2002 |
| WO | WO02/059260 A2 | 8/2002 |
| WO | WO03/039443 A2 | 5/2003 |
| WO | WO2004/067712 A2 | 8/2004 |
| WO | WO2005/016962 A2 | 2/2005 |

OTHER PUBLICATIONS

Merriam-Websters online dictionary definition of "represent", obtained from www.merriam-webster.com/dictionary/represent, last viewed on Mar. 26, 2009, 2 pages.*
Definition of "mRNA" by "Encyclopedia of Molecular Biology", Creighton, T., Ed., John Wiley and Sons, New York, 1999; online version at http://knovel.com/web/portal/browse/display?_EXT_KNOVEL_DISPLAY_bookid=737&VerticalID=0, last viewed on Feb. 15, 2010, 1 page.*
Definition of "cDNA" by "Encyclopedia of Molecular Biology", Creighton, T., Ed., John Wiley and Sons, New York, 1999; online version at http://knovel.com/web/portal/browse/display?_EXT_KNOVEL_DISPLAY_bookid=737&VerticalID=0, last viewed on Feb. 15, 2010, 16 pages.*
Ota, T. et al., "Complete sequencing and characterization of 21,243 full-length human cDNAs", Nature Genetics, vol. 36(1), pp. 40-45 (2004).
NCBI Entrez Accession No. Q9H6Q3 (gi:30173374), Holland, S.J. et al., Jun. 10, 2008.
Berry, et al., "Caspase-dependent cleavage of the hematopoietic specific adaptor protein Gads alters signaling from the T cell receptor", Oncogene, vol. 20, pp. 1203-1211 (2001).
Cao, et al., "Clnk, a Novel SLP-76-related Adaptor Molecule Expressed in Cytokine-stimulated Hemopoietic Cells", J. Exp. Med., vol. 190 (10), pp. 1527-1534 (1999).
Deloukas, et al., "The DNA sequence and comparative analysis of human chromosome 20", Nature, vol. 414, pp. 865-871 (2001).
Downward, Julian,"The GRB2/Sem-5 adaptor protein", FEBS Ltrs, vol. 338, pp. 113-117 (1994).
Fischer, et al., "Assigning folds to the proteins encoded by the genome of Mycoplasma genitalium", PNAS, vol. 94, pp. 11929-11934 (1997).
Gout, et al., "The GTPase Dynamin Binds to and Is Activated by a Subset of SH3 Domains", Cell, vol. 75, pp. 25-36 (1993).
Holland, et al., "Functional Cloning of Src-like Adapter Protein-2 (SLAP-2), a Novel Inhibitor of Antigen Receptor Signaling", J. Exp. Med., vol. 194 (9), pp. 1263-1276 (2001).
Jackman, et al. "Molecular Cloning of SLP-76, a 76-kDa Tyrosine Phosphoprotein Associated with Grb2 in T Cells", J. Biol. Chem., vol. 270 (13), pp. 7029-7032 (1995).

(Continued)

*Primary Examiner*—David J Steadman
(74) *Attorney, Agent, or Firm*—Stephen C. D'Amico

(57) ABSTRACT

The invention relates to the identification and cloning of a two novel full-length human SLAP-2 variants and their encoded polypeptides, hSLAP-2v3 and hSLAP-2v4. hSLAP-2v3 and hSLAP-2v4 are members of the SLAP family of adapter proteins and are involved in the negative regulation of intracellular T-cell signal transduction. The invention further relates to the use of these novel hSLAP-2v3 and hSLAP-2v4 polynucleotides and their encoded polypeptides as targets for therapeutic intervention in immunological and inflammatory disorders, autoimmune diseases, pulmonary diseases, proliferative immune disorders, and cancer.

20 Claims, 10 Drawing Sheets

OTHER PUBLICATIONS

Liu, et al., "The hematopoietic-specific adaptor protein Gads functions in T-cell signaling via interactions with the SLP-76 and LAT adaptors", Current Biol., vol. 9, pp. 67-75 (1999).

Loreto, et al., "Cloning and characterization of human Src-like adaptor protein 2 and a novel splice isoform, SLAP-2-v", Oncogene, vol. 22, pp. 266-273 (2003).

Loreto, et al., "Functional Cooperation between c-Cbl and Src-Like Adaptor Protein 2 in the Negative Regulation of T-Cell Receptor Signaling", Molec. Cell. Biol., vol. 22 (12), pp. 4241-4255 (2002).

Lowenstein, et al., "The SH2 and SH3 Domain-Containing Protein GRB2 Links Receptor Tyrosine Kinases to ras Signaling", Cell. vol. 70, pp. 431-442 (1992).

Motto, et al., "In Vivo Association of Grb2 with pp116, a Substrate of the T Cell Antigen Receptor-activated Protein Tyrosine Kinase", J. Biol. Chem., vol. 269 (34), pp. 21608-21613 (1994).

Myung, et al., "Adapter proteins in lymphocyte antigen-receptor signaling", Curr. Opin. Immun., vol. 12, pp. 256-266 (2000).

Pandey, et al., "A Novel Src Homology 2 Domain-containing Molecule, Src-like Adapter Protein-2 (SLAP-2), Which Negatively Regulates T Cell Receptor Signaling", J. Biol. Chem., vol. 277 (21), pp. 19131-19138 (2002).

Reif, et al., "SH3 Domains of the Adapter Molecule Grb2 Complex with Two Proteins in T Cells: The Guanine Nucleotide Exchange Protein Sos and a 75-kDa Protein That is a Substrate for T Cell Antigen Receptor-activated Tyrosine Kinases", J. Biol. Chem., vol. 269 (19), pp. 14081-14087 (1994).

Ren, et al., "Abl protein-tyrosine kinase selects the Crk adapter as a substrate using SH3-binding sites", Genes Dev., vol. 8, pp. 783-795 (1994).

Roche, et al., "Src-like adaptor protein (SLAP) is a negative regulator of mitogenesis", Curr. Biol., vol. 8, pp. 975-978 (1998).

Sali, et al., "Evaluation of Comparative Protein Modeling by MODELLER", Proteins: Structure, Function and Genetics, vol. 23, pp. 318-326 (1995).

Sosinowski, et al., "Src-like Adaptor Protein (SLAP) Is a Negative Regulator of T Cell Receptor Signaling", J. Exp. Med., vol. 191 (3), pp. 463-473 (2000).

Tang, et al., "SLAP, a dimeric adapter protein, plays a functional role in T cell receptor signaling", PNAS, vol. 96, pp. 9775-9780 (1999).

Tuosto, et al., "p95$^{vav}$ Associates with Tyrosine-phosphorylated SLP-76 in Antigen-stimulated T Cells", J. Exp. Med., vol. 184, pp. 1161-1166 (1996).

Wu, et al., "Vav and SLP-76 Interact ad Functionally Cooperate in IL-2 Gene Activation", Immunity, vol. 4, pp. 593-602 (1996).

Ye, et al., "Binding of Vav to Grb2 through dimerization of Src homology 3 domains", PNAS, vol. 91, pp. 12629-12633 (1994).

NCBI Entrez Accession No. AK025645 (gi:10438227), Kawabata, et al., Sep. 12, 2006.

NCBI Entrez Accession No. AL050318 (gi:9581785), Lloyd, D., Jul. 9, 2007.

NCBI Entrez Accession No. AL132768 (gi:8218107), Whitehead, S., Jul. 10, 2007.

NCBI Entrez Accession No. NM_032214 (gi:28416422), Loreto, et al., Jun. 3, 2007.

NCBI Entrez Accession No. NM_175077 (gi:28416423), Loreto, et al., Jun. 3, 2007.

Chan, A. et al., "Activation of ZAP-70 kinase activity by phosphorylation of tyrosine 493 is required for lymphocyte antigen receptor function", The EMBO Journal, vol. 14(11), pp. 2499-2508 (1995).

Chan, A. et al., "ZAP-70: A 70 kd Protein-Tyrosine Kinase That Associates with the TCR ζ Chain", Cell, vol. 71, pp. 649-662 (1992).

Finck, B. et al., "Treatment of Murine Lupus with CTLA4Ig", Science, vol. 265, pp. 1225-1227 (1994).

Kremer, J. et al., "Treatment of Rheumatoid Arthritis by Selective Inhibition of T-Cell Activation with Fusion Protein CTLA4Ig", The New England J of Medicine, vol. 349(20), pp. 1907-1915 (2003).

Leach, D. et al., "Enhancement of Antitumor Immunity of CTLA-4 Blockade", Science, vol. 271, pp. 1734-1736 (1996).

Tan, P. et al., "Induction of Alloantigen-specific Hyporesponsiveness in Human T Lymphocytes by Blocking Interaction of CD28 with its Natural Ligand B7/BB1", J. Exp. Med., vol. 177, pp. 165-173 (1993).

Wardenburg, J. et al., "Phosphorylation of SLP-76 by the ZAP-70 Protein-tyrosine Kinase is Required for T-cell Receptor Function", The J. of Biological Chemistry, vol. 271(33), pp. 19641-19644 (1996).

Webb, L. et al., "Prevention and amelioration of collagen-induced arthritis by blockade of the CD28 co-stimulatory pathway: requirement for both B7-1 and B7-2", Eur J Immunol., vol. 26, pp. 2320-2328 (1996).

Williams, B. et al., "Genetic Evidence for Differential Coupling of Syk Family Kinases to the T-Cell Receptor: Reconstitution Studies in a ZAP-70-Deficient Jurkat T-Cell Line", Molecular & Cellular Biology, vol. 18(3), pp. 1388-1399 (1998).

Zhang, W. et al., "LAT: The ZAP-70 Tyrosine Kinase Substrate that Links T Cell Receptor to Cellular Activation", Cell, vol. 92, pp. 83-92 (1998).

* cited by examiner

FIG. 1A

```
  1 GTGCTTCTGAGTGCTCTGCTGAGGAACAATGGGAAGTCTGCCCAGCAGAAGAAAATCTCT  60
  1                                  M  G  S  L  P  S  R  R  K  S  L  11

61 GCCAAGCCCAAGCTTGAGTTCCTCTGTCCAAGGCCAGGGACCTGTGACCATGGAAGCAGA 120
 12  P  S  P  S  L  S  S  S  V  Q  G  Q  G  P  V  T  M  E  A  E   31

121 GAGAAGCAAGGCCACAGCCGTGGCCCTGGGCAGTTTCCCGGCAGGTGGCCCGGCCGAGCT 180
 32  R  S  K  A  T  A  V  A  L  G  S  F  P  A  G  G  P  A  E  L   51

181 GTCGCTGAGACTCGGGGAGCCATTGACCATCGTCTCTGAGGATGGAGACTGGTGGACGGT 240
 52  S  L  R  L  G  E  P  L  T  I  V  S  E  D  G  D  W  W  T  V   71

241 GCTGTCTGAAGTCTCAGGCAGAGAGTATAACATCCCCAGCGTCCACGTGGCCAAAGTCTC 300
 72  L  S  E  V  S  G  R  E  Y  N  I  P  S  V  H  V  A  K  V  S   91

301 CCATGGGTGGCTGTATGAGGGCCTGAGCAGGGAGAAAGCAGAGGAACTGCTGTTGTTACC 360
 92  H  G  W  L  Y  E  G  L  S  R  E  K  A  E  E  L  L  L  L  P  111

361 TGGGAACCCTGGAGGGGCCTTCCTCATCCGGGAGAGCCAGACCAGGAGAGGCTCTTACTC 420
112  G  N  P  G  G  A  F  L  I  R  E  S  Q  T  R  R  G  S  Y  S  131

421 TCTGTCAGTCCGCCTCAGCCGCCCTGCATCCTGGGACCGGATCAGACACTACAGGATCCA 480
132  L  S  V  R  L  S  R  P  A  S  W  D  R  I  R  H  Y  R  I  H  151

481 CTGCCTTGACAATGGCTGGCTGTACATCTCACCGCGCCTCACCTTCCCCTCACTCCAGGC 540
152  C  L  D  N  G  W  L  Y  I  S  P  R  L  T  F  P  S  L  Q  A  171

541 CCTGGTGGACCATTACTCTGAGCTGGCGGATGACATCTGCTGCCTACTCAAGGAGCCCTG 600
172  L  V  D  H  Y  S  E  L  A  D  D  I  C  C  L  L  K  E  P  C  191

601 TGTCCTGCAGAGGGCTGGCCCGCTCCCTGGCAAGGATATACCCCTACCTGTGACTGTGCA 660
192  V  L  Q  R  A  G  P  L  P  G  K  D  I  P  L  P  V  T  V  Q  211

661 GAGGACACCACTCAACTGGAAAGAGCTGGACAGATGCTGCATGTACTGTGCTATGGACCA 720
212  R  T  P  L  N  W  K  E  L  D  R  C  C  M  Y  C  A  M  D  H  231

721 CGCACATACAGCCATGCTGTTTCAGAAGACTTGAAATGCCATTGATAGTTTAAAAACTCT 780
232  A  H  T  A  M  L  F  Q  K  T  *                            241

781 ACACCCGATGGAGAATCGAGGAAGACAATTTAATGTTTCATCTGAATCCAGAGGTGCATC 840
```

FIG. 1B

```
841 AAATTAAATGACAGCTCCACTTGGCAAAAAAAAAAAAAAAAAAAAAAAAAAAAAAAAAA 900

901 AAAAAAAAAAAAAAAAAAA 919
```

FIG. 2A

```
  1 GGGCAGCTGATCCATCCCTGGTGTACAAACTGCTGACTGCAGACAGATGCTGAGCTACCC  60

61 AAACCAACACCTAGCCTCTCCCTGAAGATCCTCCCAGGCTGAGAGAGTTCTGGGTGTCCT 120

121 AGGACCAAGGACACTGGCAGACTTCCAGAAGGGCCCCCAAAGCCCTAACCTGTCCAGCCA 180

181 GAGCATGCGTCTCAGCAGAGCTGTCTTCCCAAGCCTTTGATGACAAACCAATTTCCCTCG 240

241 ATGATGTGCTTCTGAGTGCTCTGCTGAGGAACAATGGGAAGTCTGCCCAGCAGAAGAAAA 300
  1                                      M  G  S  L  P  S  R  R  K     9

301 TCTCTGCCAAGCCCAAGCTTGAGTTCCTCTGTCCAAGGCCAGGGACCTGTGACCATGGAA 360
 10  S  L  P  S  P  S  L  S  S  S  V  Q  G  Q  G  P  V  T  M  E    29

361 GCAGAGAGAAGCAAGGCCACAGCCGTGGCCCTGGGCAGTTTCCCGGCAGGTGGCCCGGCC 420
 30  A  E  R  S  K  A  T  A  V  A  L  G  S  F  P  A  G  G  P  A    49

421 GAGCTGTCGCTGAGACTCGGGGAGCCATTGACCATCGTCTCTGAGGATGGAGACTGGTGG 480
 50  E  L  S  L  R  L  G  E  P  L  T  I  V  S  E  D  G  D  W  W    69

481 ACGGTGCTGTCTGAAGTCTCAGGCAGAGAGTATAACATCCCCAGCGTCCACGTGGCCAAA 540
 70  T  V  L  S  E  V  S  G  R  E  Y  N  I  P  S  V  H  V  A  K    89

541 GTCTCCCATGGGTGGCTGTATGAGGGCCTGAGCAGGGAGAAAGCAGAGGAACTGCTGTTG 600
 90  V  S  H  G  W  L  Y  E  G  L  S  R  E  K  A  E  E  L  L  L   109

601 TTACCTGGGAACCCTGGAGGGGCCTTCCTCATCCGGGAGAGCCAGACCAGGAGAGGCTCT 660
110  L  P  G  N  P  G  G  A  F  L  I  R  E  S  Q  T  R  R  G  S   129

661 TACTCTCTGTCAGTCCGCCTCAGCCGCCCTGCATCCTGGGACCGGATCAGACACTACAGG 720
130  Y  S  L  S  V  R  L  S  R  P  A  S  W  D  R  I  R  H  Y  R   149

721 ATCCACTGCCTTGACAATGGCTGGCTGTACATCTCACCGCGCCTCACCTTCCCCTCACTC 780
150  I  H  C  L  D  N  G  W  L  Y  I  S  P  R  L  T  F  P  S  L   169

781 CAGGCCCTGGTGGACCATTACTCTGAGGGCTGGCCCGCTCCCTGGCAAGGATATACCCCT 840
170  Q  A  L  V  D  H  Y  S  E  G  W  P  A  P  W  Q  G  Y  T  P   189

841 ACCTGTGACTGTGCAGAGGACACCACTCAACTGGAAAGAGCTGGACAGGAACTTCAGGAA 900
190  T  C  D  C  A  E  D  T  T  Q  L  E  R  A  G  Q  E  L  Q  E   209
```

FIG. 2B

```
 901 GGAAAATCCACTTCGGCAGCCCAGAAAACCAAGAAATGACTGCAAATATAATACGCTTTT  960
 210  G  K  S  T  S  A  A  Q  K  T  K  K  *                        221

961 CAAGCTACCTGGAATCAAGCTGTTTGTGATGGCCCCTTCCAGATCATGGAGCAGAGTTAC 1020

1021 GAAGCATCCTCCGAATGGGACGAGTAAGAACGTTCTGAAGTCCCAACCAATTCTCGCACA 1080

1081 TATCTGGTGGCGTTTCTCCACCCCCACACCTCACACTCACCCAGCGGGTGGTCTCAGTCT 1140

1141 CCCCTCTTGACTCATGCTTATCAAAGTATTCGGTCCTTTACATTCAACAAGCAACAGCAG 1200

1201 CTCAAGATTAGCGAGCCTCACTATGTGCAAAAGGCTTTAATGTACCACAGTACCCCACTT 1260

1261 CAGAGTTATTCTGAGTTAAACGAGATTCCGCTTGCAGAGCACCTGGCACGTAGAAAGCAT 1320

1321 TCTCAGCAGAAGTCTGTTACTGTTAATGTTTGTGCTACTTAATTCGAAAGAAACAAGTAA 1380

1381 CCTACTCAAAACCCTACTGCACATAAAAGGCGGAGGCCGAATCGAAAAAAAAAAAAAAAA 1440

1441 AAAAAAAAAAAAAAG 1456
```

FIG. 3

```
  1 AGGTGGCTGTATGAGGGCCTGAGCAGGGAGAAAGCAGAGGAACTGCTGTTGTTACCTGGG  60
  1 R  W  L  Y  E  G  L  S  R  E  K  A  E  E  L  L  L  L  P  G   20

61 AACCCTGGAGGGGCCTTCCTCATCCGGGAGAGCCAGACCAGGAGAGGCTCTTACTCTCTG 120
 21 N  P  G  G  A  F  L  I  R  E  S  Q  T  R  R  G  S  Y  S  L   40

121 TCAGTCCGCCTCAGCCGCCCTGCATCCTGGGACCGGATCAGACACTACAGGATCCACTGC 180
 41 S  V  R  L  S  R  P  A  S  W  D  R  I  R  H  Y  R  I  H  C   60

181 CTTGACAATGGCTGGCTGTACATCTCACCGCGCCTCACCTTCCCCTCACTCCAGGCCCTG 240
 61 L  D  N  G  W  L  Y  I  S  P  R  L  T  F  P  S  L  Q  A  L   80

241 GTGGACCATTAC 252
 81 V  D  H  Y   84
```

FIG. 4

FIG. 5
1) hSLAP-2
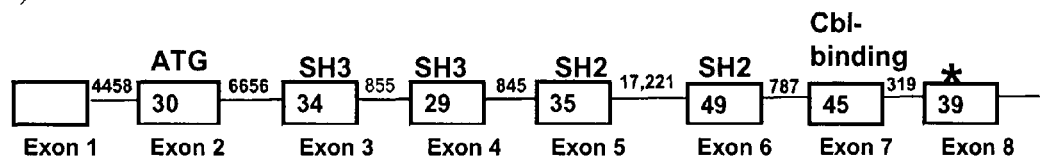
2) SLAP-2-v
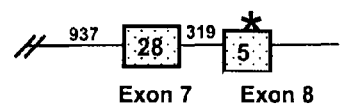
3) hSLAP-2v3
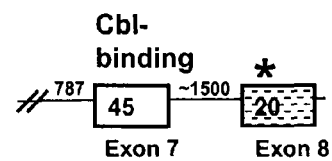
4) hSLAP-2v4
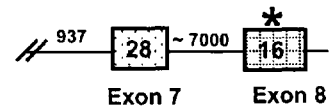

FIG. 6
a. Control_GFP
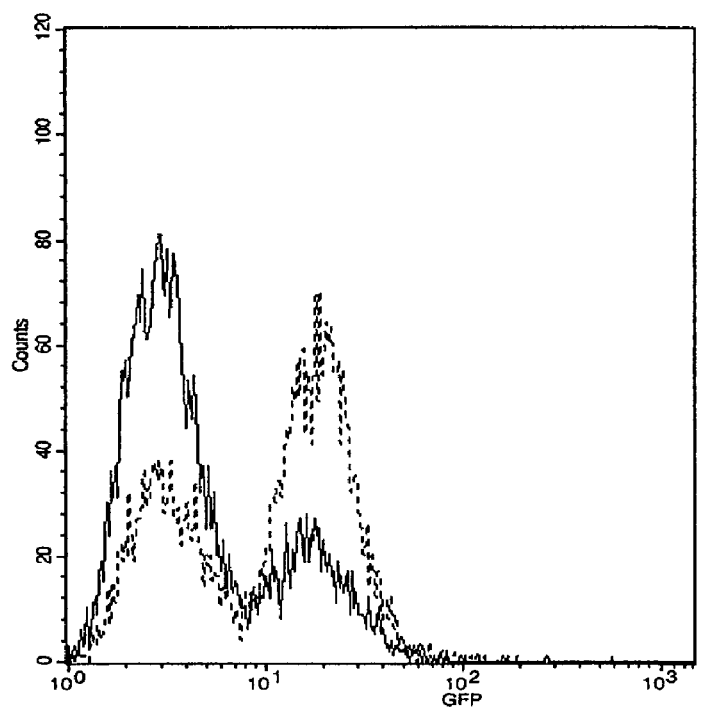
b. SLAP-2_GFP
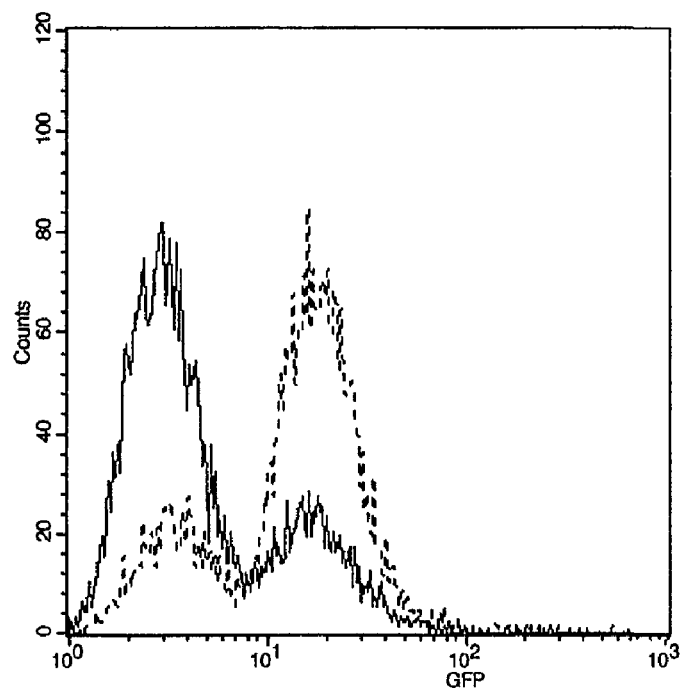

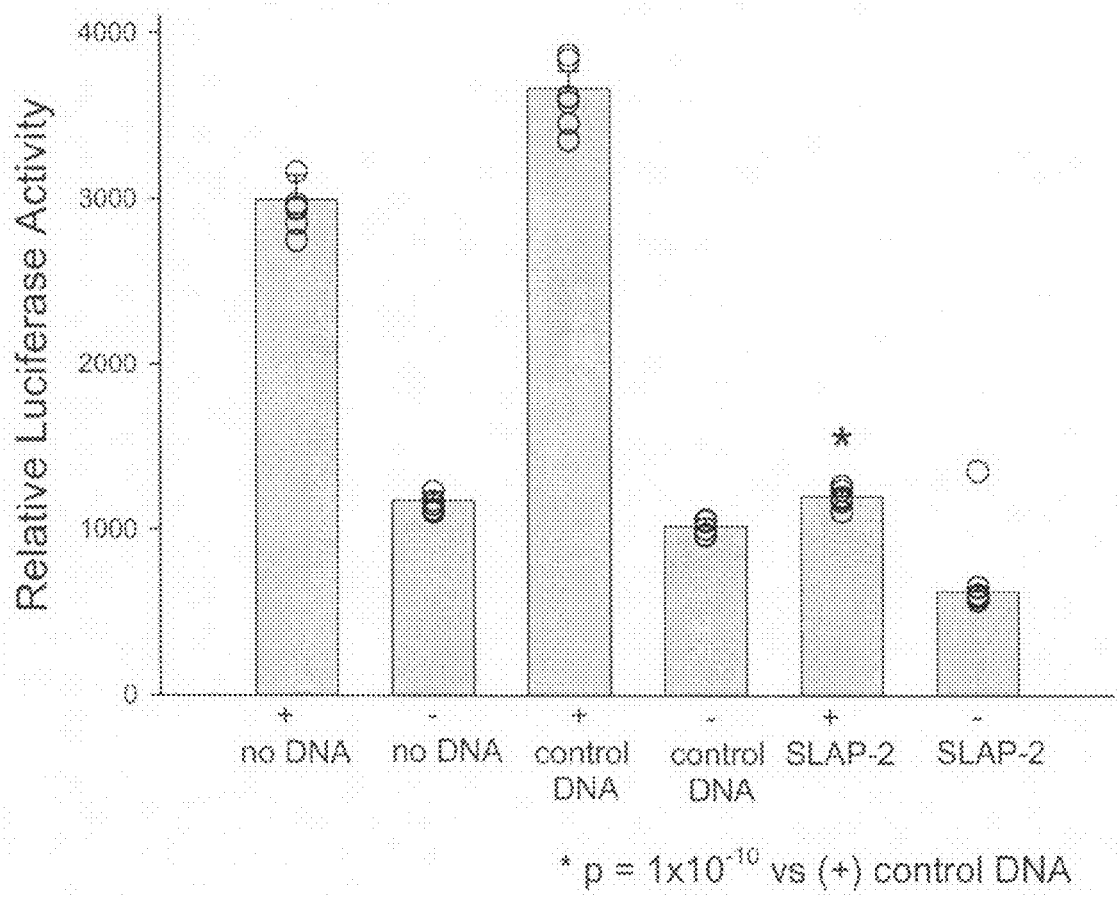

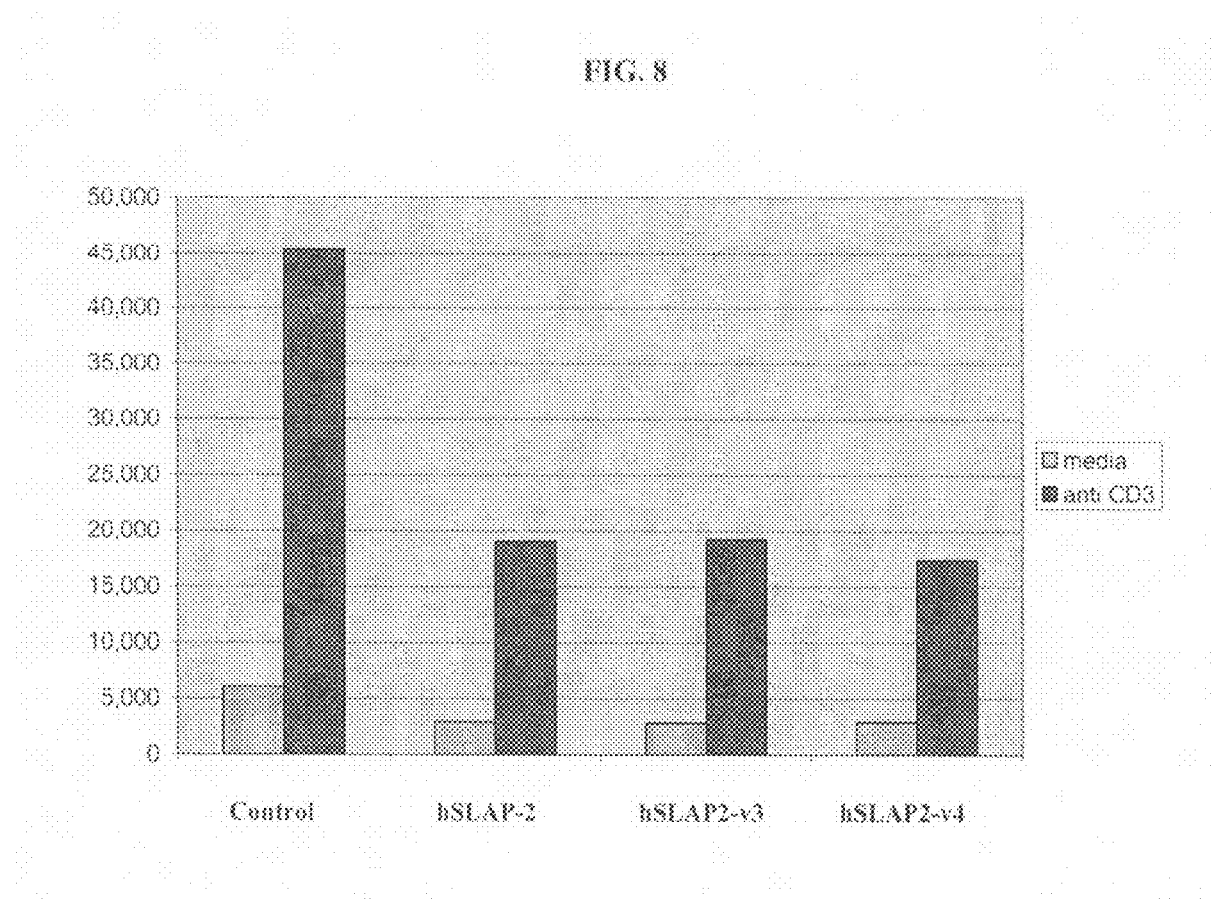

POLYNUCLEOTIDES ENCODING HUMAN SLAP-2 VARIANT, HSLAP-2V3

This application claims benefit to provisional application U.S. Ser. No. 60/794,630 filed Apr. 25, 2006 under 35 U.S.C. 119(e). The entire teachings of the referenced applications are incorporated herein by reference.

FIELD OF THE INVENTION

The invention relates to the identification and cloning of a two novel full-length human SLAP-2 variants and their encoded polypeptides, hSLAP-2v3 and hSLAP-2v4. hSLAP-2v3 and hSLAP-2v4 are members of the SLAP family of adapter proteins and are involved in the negative regulation of intracellular T-cell signal transduction. The invention further relates to the use of these novel hSLAP-2v3 and hSLAP-2v4 polynucleotides and their encoded polypeptides as targets for therapeutic intervention in immunological and inflammatory disorders, autoimmune diseases, pulmonary diseases, proliferative immune disorders, and cancer.

BACKGROUND OF THE INVENTION

Receptor signaling pathways and intracellular signaling by receptor tyrosine kinases are intimately involved in cell growth and differentiation. The binding of a particular growth factor or cellular ligand to its receptor on a cell's plasma membrane can stimulate a wide variety of biochemical responses, including changes in ion fluxes, activation of various kinases, alteration of cell shape, transcription of various genes and modulation of enzymatic activities in cellular metabolism.

Many cell receptors are tyrosine kinases whose signaling is dependent upon tyrosine phosphorylation of both the receptor and other molecules. Specific phosphorylated tyrosine residues on these receptors recruit soluble intracellular signaling molecules to the receptor-ligand complex upon extracellular ligand stimulation, thus initiating the intracellular signaling cascade that involves secondary signal transducer molecules generated by the activated receptor. The signal can then proceed through a series of steps to the nucleus and other subcellular locations where the final effects of activation by the extracellular ligand are produced. Recruitment of other molecules in the signaling pathway is often accomplished by adapter molecules, which contain only protein-protein interaction domains (e.g., SH2 and SH3 domains) and have no associated enzymatic activity. By isolating and characterizing the adapter proteins and the molecules that interact with these adapters, important components of the signaling mechanism can be discovered, monitored and controlled.

For example, one such adapter protein is Grb2, a 24-25 kDa cytosolic adapter protein containing two SH3 domains flanking an SH2 domain, which is known to be involved in linking many important molecules in receptor-ligand signal transduction (E. J. Lowenstein et al., 1992, *Cell*, 70:431-442 and J. Downward, 1994, *FEBS Letters*, 338:113-117). The central SH2 domain of Grb2 binds to an autophosphorylation site on the receptor and the two flanking SH3 domains link to intracellular effector target molecules. An example of one such target molecule is the mammalian homologue of the *Drosophila* 'son of sevenless' (SOS) protein, which is a guanine nucleotide exchange factor for ras; thus, Grb2 links receptors with the ras signal transduction pathway. It is now known that the SH3 domains also link to a number of other proteins involved in the signaling pathway, including Vav (R. Ren et al., 1994, *Genes Dev.*, 8:783-795; J. Wu et al., 1996, *Immunity*, 4:593; and L. Tuosto et al., 1996, *J. Exp. Med.*, 184:1161); c-abl (Z. S. Ye and D. Baltimore, 1994, *Proc. Natl. Acad. Sci.*, USA, 91:12629-12633); dynamin (I. Gout et al., 1993, *Cell*, 75:25-36); and SLP-76 (J. K. Jackman et al., 1995, *J. Biol. Chem.*, 270:7029-7032). In addition, several other binding proteins have been noted during B- and T-cell signaling (see, e.g., K. Reif et al., 1994, *J. Biol. Chem.*, 269:14081-14087 and D. G. Motto et al., 1994, *J. Biol. Chem.*, 269:21608-21613).

The SLP-76 family of adapter protein molecules includes the SLP-76, BLNK and Clnk proteins (P. S. Myung et al., 2000, "Adapter proteins in lymphocyte antigen-receptor signaling", *Curr. Opin. Immunol.*, 12:256-266 and M. Y. Cao et al., 1999, "Clnk, a novel SLP-76-related adapter molecule expressed in cytokine-stimulated hemopoietic cells", *J. Exp. Med.*, 190:1527-1534). Expressed exclusively in cells of hematopoietic origin, these adapter proteins are involved in intracellular signal transduction. SLP-76 is an SH2/SH3 domain-containing 76 kDa leukocyte protein that undergoes tyrosine phosphorylation following activation of the T-cell antigen receptor (TCR). SLP-76, upon tyrosine phosphorylation, interacts with Grb2 and phospholipase C-γ (PLC-γ), (J. K. Jackman et al., supra). The phosphorylation of SLP-76 on tyrosine is required for TCR-mediated cytokine secretion.

SH2 domain-containing proteins bind phosphorylated tyrosine residues and transmit important intracellular signals in many cell types. In the immune system, SH2 domain-containing proteins, such as SLP-76 and BLNK, play crucial roles in T-cell and B-cell activation. Therefore, SH2 domain-containing proteins are likely to be important targets for therapeutic intervention in immunological disorders, including autoimmune disorders and inflammatory indications.

With particular regard to B-cells, cell function is dependent on the ability of the membrane B-cell receptor (BCR) to bind to antigen and induce an efficient cascade of intracellular biochemical signaling events from the membrane to the nucleus. These events culminate in the cytosol to rearrange the morphology of the cell through cytoskeletal reorganization and in the nucleus to activate the transcription of new genes to promote cellular proliferation and differentiation. Such biochemical and cellular mechanisms are required for B-cells to mature and function to produce an efficient immune response to foreign pathogens. Conversely, the abnormal activation of B-cells can lead to unregulated cellular proliferation and uncontrolled clonal expansion, resulting in B-cell tumors, lymphomas and leukemias. In addition, unregulated activation of B-cells may also contribute to a variety of autoimmune diseases mediated by self-reactive antibodies.

In the case of T-cells, unregulated activation of the TCR can lead to aberrant T-cell growth, resulting in, for example, T-cell tumors, lymphomas, leukemias and thymomas. Thus, the ability to modulate TCR- and BCR-mediated signaling events may provide a rational approach to the treatment of T- and B-cell mediated tumors, and the like, as well as provide therapies for autoimmune diseases in which aberrant B-cell activation may be the culprit for cell destruction by autoreactive antibodies.

Because aberrant or uncontrolled regulation of the cellular processes involved in cell growth can have disastrous effects, it is important to elucidate and gain control over these processes. This requires identifying molecules that participate in the signaling events that lead to mitogenesis and dissecting their functions and mechanisms of action. The identification of these participants is important for a wide range of diagnostic, therapeutic and screening applications. More specifically, by understanding the structure of a particular participant in a receptor ligand activation cascade, one can rationally design compounds that affect that cascade, to either activate an otherwise inactive pathway, or inactivate an overly active pathway.

Similarly, having identified a particular molecule in a ligand receptor cascade, situations in which that cascade is defective can also be identified and intervention can be achieved by means of therapeutic compounds or drugs, to prevent the development of a particular pathological state. The identification of participants in particular receptor ligand activation cascades and intracellular signaling events is thus of critical importance for screening compounds that affect these cascades and events, and for treating a variety of disorders resulting from anomalies in these cascades and events as therapeutic agents. The present invention meets these and several additional needs.

Also, the discovery of two novel variants of hSLAP-2 polypeptides, and the polynucleotide encoding the same, provides the art with new compositions and methods of use and treatment for the diagnosis, screening, monitoring, therapy, and prevention of immune system related conditions or diseases, particularly those involving T-cells and B-cells.

SUMMARY OF THE INVENTION

The present invention provides two newly discovered variants of the hSLAP-2 (Human Src-Like Adapter Protein-2) polypeptide, referred to as hSLAP-2v3 and hSLAP-2-v2. All references to "hSLAP-2" shall be construed to apply to hSLAP-2v3, and/or hSLAP-2v4 unless otherwise specified herein.

The present invention provides isolated nucleic acid molecules, that comprise, or alternatively consist of, a polynucleotide encoding the hSLAP-2v3 protein having the amino acid sequence shown in FIGS. 1A-B (SEQ ID NO:2), respectively, or the amino acid sequence encoded by the cDNA clone, hSLAP-2v3 (also referred to as BMY_HPP34 variant 1, and/or bmy_hpp34-T71-2h), deposited as ATCC® Deposit Number PTA-7622 on May 10$^{th}$, 2006.

The present invention provides isolated nucleic acid molecules, that comprise, or alternatively consist of, a polynucleotide encoding the hSLAP-2v4 protein having the amino acid sequence shown in FIGS. 2A-B (SEQ ID NO:4), respectively, or the amino acid sequence encoded by the cDNA clone, hSLAP-2v4 (also referred to as BMY_HPP34 variant 2, and/or bmy_hpp34_T71-6F), deposited as ATCC® Deposit Number PTA-7622 on May 10$^{th}$, 2006.

It is an object of the present invention to provide an isolated full-length hSLAP-2v3 polynucleotide as depicted in SEQ ID NO:1, or an isolated full-length hSLAP-2v4 polynucleotide as depicted in SEQ ID NO:3. The present invention also provides a polynucleotide sequence comprising the complement of SEQ ID NO:1, SEQ ID NO:3, or variants thereof. In addition, the present invention features polynucleotide sequences which hybridize under moderate or high stringency conditions to the polynucleotide sequence of SEQ ID NO:1 or SEQ ID NO:3.

It is another object of the present invention to provide the human hSLAP-2v3 polypeptide, encoded by the polynucleotide of SEQ ID NO:1 and having the amino acid sequence of SEQ ID NO:2, or a functional or biologically active portion thereof. In accordance with the present invention, an isolated, substantially purified full-length human hSLAP-2v3 protein is provided.

It is another object of the present invention to provide the human hSLAP-2v4 polypeptide, encoded by the polynucleotide of SEQ ID NO:3 and having the amino acid sequence of SEQ ID NO:4, or a functional or biologically active portion thereof. In accordance with the present invention, an isolated, substantially purified full-length human hSLAP-2v4 protein is provided.

It is a further object of the present invention to provide compositions comprising the human hSLAP-2v3 polynucleotide sequence, or a fragment thereof, or the encoded hSLAP-2v3 polypeptide, or a fragment or portion thereof. Also provided by the present invention are pharmaceutical compositions comprising at least one hSLAP-2v3 polypeptide, or a functional portion thereof, wherein the compositions further comprise a pharmaceutically acceptable carrier, excipient, or diluent.

It is a further object of the present invention to provide compositions comprising the human hSLAP-2v4 polynucleotide sequence, or a fragment thereof, or the encoded hSLAP-2v4 polypeptide, or a fragment or portion thereof. Also provided by the present invention are pharmaceutical compositions comprising at least one hSLAP-2v4 polypeptide, or a functional portion thereof, wherein the compositions further comprise a pharmaceutically acceptable carrier, excipient, or diluent.

It is a further object of the invention to provide an anti-sense of the human hSLAP-2v3 or hSLAP-2v4 nucleic acid sequence, as well as oligonucleotides, fragments, or portions of the hSLAP-2v3 or hSLAP-2v4 nucleic acid molecule or anti-sense molecule. Also provided are expression vectors and host cells comprising polynucleotides that encode the human hSLAP-2v3 or hSLAP-2v4 polypeptide, or portions or fragments thereof.

It is an object of the present invention to provide methods for producing a polypeptide comprising the amino acid sequence depicted in SEQ ID NO:2, SEQ ID NO:4, or a fragment thereof, comprising the steps of a) cultivating a host cell containing an expression vector containing at least a functional fragment of the polynucleotide sequence encoding the human hSLAP-2v3 or hSLAP-2v4 polypeptide according to this invention under conditions suitable for the expression of the polynucleotide; and b) recovering the polypeptide from the host cell.

It is a further object of the present invention to provide antibodies, and binding fragments thereof, which bind specifically to the hSLAP-2v3 or hSLAP-2v4 polypeptide, or an epitope thereof, for use as therapeutics and diagnostic agents.

It is an object of the present invention to provide methods for screening for agents or molecules which bind to and/or modulate human hSLAP-2v3 or hSLAP-2v4 polypeptide, e.g., inhibitors, other intracellular signaling molecules and antagonists, as well as the modulators, particularly, inhibitors and antagonists, particularly those that are obtained from the screening methods described. Also provided are methods to screen for inhibitors of the interaction, e.g., a binding interaction, of the hSLAP-2v3 or hSLAP-2v4 protein with other signaling proteins, particularly those having SH2 and SH3 interaction domains.

It is also an object of the present invention to provide a substantially purified antagonist or inhibitor of the polypeptide of SEQ ID NO:2 or SEQ ID NO:4. In this regard, and by way of example, a purified antibody that binds to a polypeptide comprising the amino acid sequence of SEQ ID NO:2 or SEQ ID NO:4 is provided.

It is a further object of the present invention to provide hSLAP-2v3 or hSLAP-2v4 nucleic acid sequences, polypeptide, peptides and antibodies for use in the diagnosis and/or screening of disorders or diseases associated with expression of the polynucleotide and its encoded polypeptide as described herein.

It is an object of the present invention to provide kits for screening and diagnosis of disorders associated with aberrant or uncontrolled cellular development and with the expression of the hSLAP-2v3 or hSLAP-2v4 polynucleotide and its encoded polypeptide as described herein.

It is an object of the present invention to further provide methods for the treatment, diagnosis or prevention of T-cell and B-cell neoplasms; inflammation disorders, diseases and conditions, rheumatoid arthritis, osteoarthritis, psoriasis, rhinitis, inflammatory bowel disease (Crohn's and ulcerative colitis), allergies, particularly those involving hyperactivity of B-cells and T-cells, or other immune cells, such as mast cells or eosinophils; autoimmune diseases such as systemic lupus erythematosus and multiple sclerosis; pulmonary diseases including asthma, acute respiratory distress syndrome, and chronic obstructive pulmonary disorder; tissue/organ rejection; and cancer.

It is an object of the present invention to further provide methods for the treatment, diagnosis or prevention of immune cell disorders or diseases, e.g., B- or T-cell tumors, lymphomas, leukemias, autoimmune diseases, or inflammation, involving administering to an individual in need of treatment or prevention an effective amount of a purified antagonist or agonist of the hSLAP-2v3 or hSLAP-2v4 polypeptide. It is an object of the present invention to provide a method for detecting a polynucleotide that encodes the hSLAP-2v3 or hSLAP-2v4 polypeptide in a biological sample comprising the steps of: a) hybridizing the complement of the polynucleotide sequence encoding SEQ ID NO:2 or SEQ ID NO:4 to a nucleic acid material of a biological sample, thereby forming a hybridization complex; and b) detecting the hybridization complex, wherein the presence of the complex correlates with the presence of a polynucleotide encoding the hSLAP-2v3 or hSLAP-2v4 polypeptide in the biological sample. The nucleic acid material may be further amplified by the polymerase chain reaction prior to hybridization.

Further objects, features and advantages of the present invention will be better understood upon a reading of the detailed description of the invention when considered in connection with the accompanying figures/drawings.

BRIEF DESCRIPTION OF THE FIGURES

FIGS. 1A-B show the polynucleotide sequence (SEQ ID NO:1) and deduced amino acid sequence (SEQ ID NO:2) of the novel human hSLAP-2 variant, hSLAP-2v3, of the present invention. The standard one-letter abbreviation for amino acids is used to illustrate the deduced amino acid sequence. The polynucleotide sequence contains a sequence of 919 nucleotides (SEQ ID NO:1), encoding a polypeptide of 241 amino acids (SEQ ID NO:2). An analysis of the hSLAP-2v3 polypeptide determined that it comprised the following features: an SH3 domain located from about amino acid 35 to about amino acid 90 of SEQ ID NO:2, denoted by single underlining; an SH2 domain located from about amino acid 94 to about amino acid 176 of SEQ ID NO:2, denoted by double underlining; and conserved tyrosine phosphorylation sites at amino acid positions 80, 96, 130, 148, 159, and 176 of SEQ ID NO:2, denoted in bold. The hSLAP-2v3 polypeptide functions as an inhibitor of T-cell receptor activation as described more particularly elsewhere herein.

FIGS. 2A-B show the polynucleotide sequence (SEQ ID NO:3) and deduced amino acid sequence (SEQ ID NO:4) of the novel human hSLAP-2 variant, hSLAP-2v4, of the present invention. The standard one-letter abbreviation for amino acids is used to illustrate the deduced amino acid sequence. The polynucleotide sequence contains a sequence of 1456 nucleotides (SEQ ID NO:3), encoding a polypeptide of 221 amino acids (SEQ ID NO:4). An analysis of the hSLAP-2v4 polypeptide determined that it comprised the following features: an SH3 domain located from about amino acid 35 to about amino acid 90 of SEQ ID NO:4, denoted by single underlining; an SH2 domain located from about amino acid 94 to about amino acid 176 of SEQ ID NO:4, denoted by double underlining; and conserved tyrosine phosphorylation sites at amino acid positions 80, 96, 130, 148, 159, and 176 of SEQ ID NO:4, denoted in bold. The hSLAP-2v4 polypeptide functions as an inhibitor of T-cell receptor activation as described more particularly elsewhere herein.

FIG. 3 shows the partial polynucleotide sequence (SEQ ID NO:5) and partial deduced amino acid sequence (SEQ ID NO:6) of the novel human hSLAP-2 variant, hSLAP-2v3, of the present invention. The standard one-letter abbreviation for amino acids is used to illustrate the deduced amino acid sequence. The polynucleotide sequence contains a sequence of 252 nucleotides (SEQ ID NO:5), encoding a polypeptide of 84 amino acids (SEQ ID NO:6).

FIG. 4 shows the regions of identity and similarity between the encoded hSLAP-2v3 (SEQ ID NO:2), hSLAP-2v4 (SEQ ID NO:4), and partial hSLAP-2v3 (SEQ ID NO:6) polypeptides to the hSLAP-2 polypeptide (hSLAP-2; disclosed in U.S. Pat. No. 7,101,686, issued Sep. 5, 2006; SEQ ID NO:9); and SLAP-2-v (GENBANK® Accession No. gi|NM_175077; SEQ ID NO:14). The alignment was performed using the CLUSTALW algorithm using default parameters as described herein (VECTOR NTI® suite of programs). The darkly shaded amino acids represent regions of matching identity. The lightly shaded amino acids represent regions of matching similarity. Dots ("•") between residues indicate gapped regions of non-identity for the aligned polypeptides.

FIG. 5 shows a schematic representation of the exons, introns, and functional domains contained within the hSLAP-2 (hSLAP-2; disclosed in U.S. Pat. No. 7,101,686, issued Sep. 5, 2006; SEQ ID NO:9); SLAP-2-v (GENBANK® Accession No. gi|NM_175077; SEQ ID NO:14), hSLAP-2v3 (SEQ ID NO:2), and hSLAP-2v4 (SEQ ID NO:4) polypeptides. The length of each exon, intron, and functional domain is provided either above or within each feature in nucleotides. In hSLAP-2, Exon 1 contains the 5' untranslated sequence; Exon 2 contains the initiating ATG, Exons 3 and 4 code for the SH3 domain, Exons 5 and 6 code for the SH2 domain, Exon 7 codes for the down-regulating Cbl-binding domain, and Exon 8 contains the stop codon and 3' untranslated region, and overlaps with the 3' untranslated exon of another gene C20orf24/RAB5-interacting protein. As shown, the CBL binding domain of hSLAP-2 is disrupted in the hSLAP-2-v and hSLAP-2v4 polypeptides, but retained in hSLAP-2v3.

FIG. 6 shows an assessment of transfection efficiency by FACs analysis for hSLAP-2. Histograms for green fluorescent protein-positive cells were created by using CellQuest software. On the histograms, cells transfected with no DNA are shown with a solid line and transfected cells, Control_GFP (a) and SLAP-2_GFP (b) are shown as an overlays with dotted lines.

FIG. 7 shows NFAT promoter activation is inhibited by SLAP-2. NFAT promoter-luciferase Jurkat cells were transiently transfected with no DNA, 40 μg of a Control_GFP plasmid or 40 μg of SLAP-2_GFP plasmid by electroporation (300 V, 975 μF). After 40 hours, the cells were centrifuged and resuspended in assay media. Six replicates of each transfection of 40,000 viable cells/well in a 100 μl volume were plated in 96-well assay plate. Half of the cells were incubated for six hours with anti-human CD3 antibody (+) and the other half were left untreated (−). After six hours stimulation, luciferase activity was assayed. Error bars indicate standard deviations.

FIG. 8 shows NFAT promoter activation is inhibited by both SLAP-2-v3 and SLAP-2-v4 at levels comparable to the wild-type SLAP-2. NFAT promoter-luciferase Jurkat cells were transiently transfected with no DNA, 40 µg of a Control_GFP plasmid or 40 µg of SLAP-2_GFP plasmid by electroporation (300 V, 975 µF). After 40 hours, the cells were centrifuged and resuspended in assay media. Three replicates of each transfection of cells in a 100 µl volume were plated in 96-well assay plate. Half of the cells were incubated for six hours with anti-human CD3 antibody (darkly shaded bars) and the other half were left untreated (lightly shaded bars). After six hours stimulation, luciferase activity was assayed and normalized using the co-transfected renilla reporter. The X-axis shows the normalized level of firefly luciferase after taking into account the level of renilla activity to control for transfection efficiencies.

DETAILED DESCRIPTION OF THE INVENTION

The present invention provides a novel isolated polynucleotide (SEQ ID NO:1) encoding the full-length hSLAP-2v3 polypeptide (SEQ ID NO:2), in addition to providing a novel isolated polynucleotide (SEQ ID NO:3) encoding the full-length hSLAP-2v4 polypeptide (SEQ ID NO:4), both proteins being variants of the hSLAP-2 protein, and thus members of Src homology domain, SH2/SH3-domain containing adapter proteins which function in the receptor-ligand signal transduction pathway in cells of the hematopoietic lineage.

The following definitions are provided to more fully describe the present invention in its various aspects. The definitions are intended to be useful for guidance and elucidation, and are not intended to limit the disclosed invention and its embodiments.

DEFINITIONS

The "hSLAP-2v3 polypeptide" or "hSLAP-2v4 polypeptide" (or protein) refers to the amino acid sequence of substantially purified hSLAP-2v3 or hSLAP-2v4, which, although isolated from a human cDNA library source according to the present invention, may be obtained from any species, preferably mammalian, including mouse, rat, non-human primates, and more preferably, human; and from a variety of sources, including natural, synthetic, semi-synthetic, or recombinant. Functional fragments of the hSLAP-2v3 or hSLAP-2v4 polypeptide are also embraced by the present invention.

An "agonist" refers to a molecule which, when bound to the hSLAP-2v3 or hSLAP-2v4 polypeptide, or a functional fragment thereof, increases or prolongs the duration of the effect of the hSLAP-2v3 or hSLAP-2v4 polypeptide. Agonists may include proteins, nucleic acids, carbohydrates, or any other molecules that bind to and modulate the effect of hSLAP-2v3 or hSLAP-2v4 polypeptide. An "antagonist" (e.g., inhibitor) refers to a molecule which, when bound to the hSLAP-2v3 or hSLAP-2v4 polypeptide, or a functional fragment thereof, decreases or eliminates the amount or duration of the biological or immunological activity of hSLAP-2v3 or hSLAP-2v4 polypeptide. Antagonists may include proteins, nucleic acids, carbohydrates, antibodies, or any other molecules that decrease, reduce or eliminate the effect of the hSLAP-2v3 or hSLAP-2v4 polypeptide.

"Nucleic acid sequence", as used herein, refers to an oligonucleotide, nucleotide, or polynucleotide, and fragments or portions thereof, and to DNA or RNA of genomic or synthetic origin which may be single- or double-stranded, and represent the sense or anti-sense strand. By way of nonlimiting example, fragments include contiguous nucleic acid sequences that are greater than 20-60 nucleotides in length, and preferably include fragments that are at least about 537 to 666 contiguous nucleotides, or which are at least 1000 nucleotides or greater in length. In this context, the term "about" refers to 1, 2, 3, 4, 5, 6, 7, 8, 9 or 10 additional nucleotides either on the 5' or 3' end or both. Nucleic acids for use as probes or primers may differ in length as described herein.

Similarly, "amino acid sequence" as used herein refers to an oligopeptide, peptide, polypeptide, or protein sequence, and fragments or portions thereof, and to naturally occurring or synthetic molecules. Amino acid sequence fragments are typically from about 4 or 5 to about 35 contiguous amino acids in length, preferably from about 5 to about 15 or 20 amino acids in length, from about 179 to 222 amino acids in length, and optimally, retain the biological activity or function of the hSLAP-2v3 or hSLAP-2v4 polypeptide. In this context, the term "about" refers to 1, 2, 3, 4, 5, 6, 7, 8, 9 or 10 additional amino acids either on the N- or C-terminus or both.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule. In addition, the terms "polypeptide" and "protein" are frequently used interchangeably herein to refer to the encoded product of the hSLAP-2v3 or hSLAP-2v4 nucleic acid sequence of the present invention.

A "variant" of the hSLAP-2v3 or hSLAP-2v4 polypeptide can refer to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Minor variations may also include amino acid deletions or insertions, or both. Guidance in determining which amino acid residues may be substituted, inserted, or deleted without abolishing functional biological or immunological activity may be found using computer programs well known in the art, for example, DNASTAR® software, or VECTOR NTI®.

An "allele" or "allelic sequence" is an alternative form of the hSLAP-2v3 or hSLAP-2v4 nucleic acid sequence. Alleles may result from at least one mutation in the nucleic acid sequence and may yield altered mRNAs or polypeptides whose structure or function may or may not be altered. Any given gene, whether natural or recombinant, may have none, one, or many allelic forms. Common mutational changes, which give rise to alleles, are generally ascribed to natural deletions, additions, or substitutions of nucleotides. Each of these types of changes may occur alone, or in combination with the others, one or more times in a given sequence.

Altered nucleic acid sequences encoding the hSLAP-2v3 or hSLAP-2v4 polypeptide include nucleic acid sequences containing deletions, insertions and/or substitutions of different nucleotides resulting in a polynucleotide that encodes the same or a functionally equivalent hSLAP-2v3 or hSLAP-2v4 polypeptide. Altered nucleic acid sequences may further include polymorphisms of the polynucleotide encoding the hSLAP-2v3 or hSLAP-2v4 polypeptide; such polymorphisms may or may not be readily detectable using a particular oligonucleotide probe. The encoded protein may also contain deletions, insertions, or substitutions of amino acid residues, which produce a silent change and result in a functionally equivalent hSLAP-2v3 or hSLAP-2v4 protein of the present invention. Deliberate amino acid substitutions may be made on the basis of similarity in polarity, charge, solubility, hydrophobicity, hydrophilicity, and/or the amphipathic nature of the residues, as long as the biological activity or function of hSLAP-2v3 or hSLAP-2v4 protein is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; and phenylalanine and tyrosine.

"Peptide nucleic acid" (PNA) refers to an antisense molecule or anti-gene agent which comprises an oligonucleotide ("oligo") linked via an amide bond, similar to the peptide backbone of amino acid residues. PNAs typically comprise oligos of at least 5 nucleotides linked via amide bonds. PNAs may or may not terminate in positively charged amino acid residues to enhance binding affinities to DNA. Such amino acids include, for example, lysine and arginine, among others. These small molecules stop transcript elongation by binding to their complementary strand of nucleic acid (P. E. Nielsen et al., 1993, *Anticancer Drug Des.,* 8:53-63). PNA may be pegylated to extend their lifespan in the cell where they preferentially bind to complementary single stranded DNA and RNA.

"Oligonucleotides" or "oligomers" refer to a nucleic acid sequence, preferably comprising contiguous nucleotides, of at least about 6 nucleotides to about 60 nucleotides, preferably at least about 8 to 10 nucleotides in length, more preferably at least about 12 nucleotides in length, e.g., about 15 to 35 nucleotides, or about 15 to 25 nucleotides, or about 20 to 35 nucleotides, which can be typically used, for example, as probes or primers, in PCR amplification assays, hybridization assays, or in microarrays. It will be understood that the term oligonucleotide is substantially equivalent to the terms primer, probe, or amplimer, as commonly defined in the art. It will also be appreciated by those skilled in the pertinent art that a longer oligonucleotide probe, or mixtures of probes, e.g., degenerate probes, can be used to detect longer, or more complex, nucleic acid sequences, for example, genomic DNA. In such cases, the probe may comprise at least 20-200 nucleotides, preferably, at least 30-100 nucleotides, and more preferably, 50-100 nucleotides.

"Amplification" refers to the production of additional copies of a nucleic acid sequence and is generally carried out using polymerase chain reaction (PCR) technologies, which are well known and practiced in the art (see, D. W. Dieffenbach and G. S. Dveksler, 1995, *PCR Primer, a Laboratory Manual,* Cold Spring Harbor Press, Plainview, N.Y.).

"Microarray" is an array of distinct polynucleotides or oligonucleotides synthesized on a substrate, such as paper, nylon, or other type of membrane; filter; chip; glass slide; or any other type of suitable solid support.

The term "antisense" refers to nucleotide sequences, and compositions containing nucleic acid sequences, which are complementary to a specific DNA or RNA sequence. The term "antisense strand" is used in reference to a nucleic acid strand that is complementary to the "sense" strand. Antisense (i.e., complementary) nucleic acid molecules include PNA and may be produced by any method, including synthesis or transcription. Once introduced into a cell, the complementary nucleotides combine with natural sequences produced by the cell to form duplexes, which block either transcription or translation. The designation "negative" is sometimes used in reference to the antisense strand, and "positive" is sometimes used in reference to the sense strand.

The term "consensus" refers to the sequence that reflects the most common choice of base or amino acid at each position among a series of related DNA, RNA or protein sequences. Areas of particularly good agreement often represent conserved functional domains.

A "deletion" refers to a change in either nucleotide or amino acid sequence and results in the absence of one or more nucleotides or amino acid residues. By contrast, an insertion (also termed "addition") refers to a change in a nucleotide or amino acid sequence that results in the addition of one or more nucleotides or amino acid residues, as compared with the naturally occurring molecule. A "substitution" refers to the replacement of one or more nucleotides or amino acids by different nucleotides or amino acids.

A "derivative nucleic acid molecule" refers to the chemical modification of a nucleic acid encoding, or complementary to, the encoded hSLAP-2v3 or hSLAP-2v4 polypeptide. Such modifications include, for example, replacement of hydrogen by an alkyl, acyl, or amino group. A nucleic acid derivative encodes a polypeptide, which retains the essential biological and/or functional characteristics of the natural molecule. A derivative polypeptide is one which is modified by glycosylation, pegylation, or any similar process that retains the biological and/or functional or immunological activity of the polypeptide from which it is derived.

The term "biologically active", i.e., functional, refers to a protein or polypeptide or peptide fragment thereof having structural, regulatory, or biochemical functions of a naturally occurring molecule. In the case of hSLAP-2v3 and/or hSLAP-2v4, biologically active refers to the same or similar negative T-cell or B-cell regulation of intracellular signal transduction activity observed for wild-type hSLAP-2. Likewise, "immunologically active" refers to the capability of the natural, recombinant, or synthetic hSLAP-2v3 or hSLAP-2v4, or any oligopeptide thereof, to induce a specific immune response in appropriate animals or cells, for example, to generate antibodies, and to bind with specific antibodies.

The term "hybridization" refers to any process by which a strand of nucleic acid binds with a complementary strand through base pairing.

The term "hybridization complex" refers to a complex formed between two nucleic acid sequences by virtue of the formation of hydrogen bonds between complementary G and C bases and between complementary A and T bases. The hydrogen bonds may be further stabilized by base stacking interactions. The two complementary nucleic acid sequences hydrogen bond in an anti-parallel configuration. A hybridization complex may be formed in solution (e.g., $C_o t$ or $R_o t$ analysis), or between one nucleic acid sequence present in solution and another nucleic acid sequence immobilized on a solid support (e.g., membranes, filters, chips, pins, or glass slides, or any other appropriate substrate to which cells or their nucleic acids have been affixed).

The terms "stringency" or "stringent conditions" refer to the conditions for hybridization as defined by nucleic acid composition, salt and temperature. These conditions are well known in the art and may be altered to identify and/or detect identical or related polynucleotide sequences in a sample. A variety of equivalent conditions comprising either low, moderate, or high stringency depend on factors such as the length and nature of the sequence (DNA, RNA, base composition), reaction milieu (in solution or immobilized on a solid substrate), nature of the target nucleic acid (DNA, RNA, base composition), concentration of salts and the presence or absence of other reaction components (e.g., formamide, dextran sulfate and/or polyethylene glycol) and reaction temperature (within a range of from about 5° C. below the melting temperature of the probe to about 20° C. to 25° C. below the melting temperature). One or more factors may be varied to generate conditions, either low or high stringency, that is different from but equivalent to the aforementioned conditions.

As will be understood by those of skill in the art, the stringency of hybridization may be altered in order to identify or detect identical or related polynucleotide sequences. As will be further appreciated by the skilled practitioner, the melting temperature, Tm, can be approximated by the formulas as known in the art, depending on a number of parameters, such as the length of the hybrid or probe in number of nucleotides, or hybridization buffer ingredients and conditions (see, for example, T. Maniatis et al., *Molecular Cloning: A Laboratory Manual*, Cold Spring Harbor Laboratory, Cold Spring Harbor, N.Y., 1982 and J. Sambrook et al., *Molecular Cloning: A Laboratory Manual*, Cold Spring Harbor Laboratory, Cold Spring Harbor, N.Y., 1989; *Current Protocols in Molecular Biology*, Eds. F. M. Ausubel et al., Vol. 1, "Preparation and Analysis of DNA", John Wiley and Sons, Inc., 1994-1995, Suppls. 26, 29, 35 and 42; pp. 2.10.7-2.10.16; G. M. Wahl and S. L. Berger (1987; *Methods Enzymol.* 152:399-407); and A. R. Kimmel, 1987; *Methods of Enzymol.* 152: 507-511). As a general guide, Tm decreases approximately 1° C.-1.5° C. with every 1% decrease in sequence homology. Also, in general, the stability of a hybrid is a function of sodium ion concentration and temperature. Typically, the hybridization reaction is initially performed under conditions of low stringency, followed by washes of varying, but higher stringency. Reference to hybridization stringency, e.g., high, moderate, or low stringency, typically relates to such washing conditions.

Thus, by way of non-limiting example, "high stringency" refers to conditions that permit hybridization of those nucleic acid sequences that form stable hybrids in 0.018M NaCl at about 65° C. (i.e., if a hybrid is not stable in 0.018M NaCl at about 65° C., it will not be stable under high stringency conditions). High stringency conditions can be provided, for instance, by hybridization in 50% formamide, 5×Denhardt's solution, 5×SSPE (saline sodium phosphate EDTA) (1×SSPE buffer comprises 0.15 M NaCl, 10 mM $Na_2HPO_4$, 1 mM EDTA), (or 1×SSC buffer containing 150 mM NaCl, 15 mM $Na_3$ citrate•$2H_2O$, pH 7.0), 0.2% SDS at about 42° C., followed by washing in 1×SSPE (or saline sodium citrate, SSC) and 0.1% SDS at a temperature of at least about 42° C., preferably about 55° C., more preferably about 65° C.

"Moderate stringency" refers, by nonlimiting example, to conditions that permit hybridization in 50% formamide, 5×Denhardt's solution, 5×SSPE (or SSC), 0.2% SDS at 42° C. (to about 50° C.), followed by washing in 0.2×SSPE (or SSC) and 0.2% SDS at a temperature of at least about 42° C., preferably about 55° C., more preferably about 65° C.

"Low stringency" refers, by non-limiting example, to conditions that permit hybridization in 10% formamide, 5×Denhardt's solution, 6×SSPE (or SSC), 0.2% SDS at 42° C., followed by washing in 1×SSPE (or SSC) and 0.2% SDS at a temperature of about 45° C., preferably about 50° C.

For additional stringency conditions, see T. Maniatis et al., *Molecular Cloning: A Laboratory Manual*, Cold Spring Harbor Laboratory, Cold Spring Harbor, N.Y. (1982). It is to be understood that the low, moderate and high stringency hybridization/washing conditions may be varied using a variety of ingredients, buffers and temperatures well known to and practiced by the skilled practitioner.

The terms "complementary" or "complementarity" refer to the natural binding of polynucleotides under permissive salt and temperature conditions by base pairing. For example, the sequence "A-G-T" binds to the complementary sequence "T-C-A". Complementarity between two single-stranded molecules may be "partial", in which only some of the nucleic acids bind, or it may be complete when total complementarity exists between single-stranded molecules. The degree of complementarity between nucleic acid strands has significant effects on the efficiency and strength of hybridization between nucleic acid strands. This is of particular importance in amplification reactions, which depend upon binding between nucleic acids strands, as well as in the design and use of PNA molecules.

The term "homology" refers to a degree of complementarity. There may be partial sequence homology or complete homology, wherein "complete homology" is equivalent to identity, e.g., 100% identity. A partially complementary sequence that at least partially inhibits an identical sequence from hybridizing to a target nucleic acid is referred to using the functional term "substantially homologous". The inhibition of hybridization of the completely complementary sequence to the target sequence may be examined using a hybridization assay (e.g., Southern or Northern blot, solution hybridization, and the like) under conditions of low stringency. A substantially homologous sequence or probe will compete for and inhibit the binding (i.e., the hybridization) of a completely homologous sequence or probe to the target sequence under conditions of low stringency. Nonetheless, conditions of low stringency do not permit non-specific binding; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

The present invention is also directed to nucleic acid molecules which comprise, or alternatively, consist of, a nucleotide sequence which is at least about 80%, 85%, 90%, 91%, 92%, 93%, 93.6%, 94%, 95%, 96%, 97%, 97.9%, 98%, 99%, 99.1%, 99.2%, 99.3%, 99.4%, 99.5%, 99.6%, 99.7%, 99.8%, or 99.9% identical to, for example, any of the nucleotide sequences disclosed herein.

The present invention encompasses polypeptide sequences which comprise, or alternatively consist of, an amino acid sequence which is at least about 80%, 85%, 90%, 91%, 92%, 93%, 94%, 95%, 96%, 96.2%, 97%, 98%, 99%, 99.1%, 99.2%, 99.3%, 99.4%, 99.5%, 99.6%, 99.7%, 99.8%, or 99.9% identical to, the following non-limited examples, the polypeptide sequence identified as SEQ ID NO:2 or 4, the polypeptide sequence encoded by a cDNA provided in the deposited clone, and/or polypeptide fragments of any of the polypeptides provided herein. Polynucleotides encoded by these nucleic acid molecules are also encompassed by the invention. In another embodiment, the invention encompasses nucleic acid molecules which comprise, or alternatively, consist of a polynucleotide which hybridizes under stringent conditions, or alternatively, under lower stringency conditions, to any of the polynucleotides disclosed herein. Polynucleotides which hybridize to the complement of these nucleic acid molecules under stringent hybridization conditions or alternatively, under lower stringency conditions, are also encompassed by the invention, as are polypeptides encoded by these polypeptides.

The present invention is also directed to polypeptides which comprise, or alternatively consist of, an amino acid sequence which is at least about 80%, 85%, 90%, 91%, 92%, 93%, 94%, 95%, 96%, 96.2%, 97%, 98%, 99%, 99.1%, 99.2%, 99.3%, 99.4%, 99.5%, 99.6%, 99.7%, 99.8%, or 99.9% identical to, for example, the polypeptide sequence shown in SEQ ID NO:2 or 4, a polypeptide sequence encoded by the nucleotide sequence in SEQ ID NO:1 or 3, a polypeptide sequence encoded by the cDNA, and/or polypeptide fragments of any of these polypeptides (e.g., those fragments described herein). Polynucleotides which hybridize to the complement of the nucleic acid molecules encoding these polypeptides under stringent hybridization conditions or alternatively, under lower stringency conditions, are also encompasses by the present invention, as are the polypeptides encoded by these polynucleotides.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence referenced in Table 1, the ORF (open reading frame), or any fragment specified as described herein.

As a practical matter, whether any particular nucleic acid molecule or polypeptide is at least about 80%, 85%, 90%, 91%, 92%, 93%, 94%, 95%, 96%, 96.2%, 97%, 97.9%, 98%, 99%, 99.1%, 99.2%, 99.3%, 99.4%, 99.5%, 99.6%, 99.7%, 99.8%, or 99.9% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673-4680, (1994)), which is based on the algorithm of Higgins, D. G., et al., Computer Applications in the Biosciences (CABIOS), 8(2):189-191, (1992). In a sequence alignment the query and subject sequences are both DNA sequences. An RNA sequence can be compared by converting U's to T's. However, the CLUSTALW algorithm automatically converts U's to T's when comparing RNA sequences to DNA sequences. The result of said global sequence alignment is in percent identity. Preferred parameters used in a CLUSTALW alignment of DNA sequences to calculate percent identity via pairwise alignments are: Matrix=IUB, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps:Off; Hydrophilic Residue Gap=Off; and Transition Weighting=0. The pairwise and multiple alignment parameters provided for CLUSTALW above represent the default parameters as provided with the ALIGNX® software program (VECTOR NTI® suite of programs, version 6.0).

The present invention encompasses the application of a manual correction to the percent identity results, in the instance where the subject sequence is shorter than the query sequence because of 5' or 3' deletions, not because of internal deletions. If only the local pairwise percent identity is required, no manual correction is needed. However, a manual correction may be applied to determine the global percent identity from a global polynucleotide alignment. Percent identity calculations based upon global polynucleotide alignments are often preferred since they reflect the percent identity between the polynucleotide molecules as a whole (i.e., including any polynucleotide overhangs, not just overlapping regions), as opposed to, only local matching polynucleotides. Manual corrections for global percent identity determinations are required since the CLUSTALW program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the CLUSTALW sequence alignment. This percentage is then subtracted from the percent identity, calculated by the above CLUSTALW program using the specified parameters, to arrive at a final percent identity score. This corrected score may be used for the purposes of the present invention. Only bases outside the 5' and 3' bases of the subject sequence, as displayed by the CLUSTALW alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the CLUSTALW alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the CLUSTALW program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by CLUSTALW is not manually corrected. Once again, only bases 5' and 3' of the subject sequence which are not matched/aligned with the query sequence are manually corrected for. No other manual corrections are required for the purposes of the present invention.

In addition to the above method of aligning two or more polynucleotide or polypeptide sequences to arrive at a percent identity value for the aligned sequences, it may be desirable in some circumstances to use a modified version of the CLUSTALW algorithm which takes into account known structural features of the sequences to be aligned, such as for example, the SWISS-PROT® designations for each sequence. The result of such a modified CLUSTALW algorithm may provide a more accurate value of the percent identity for two polynucleotide or polypeptide sequences. Support for such a modified version of CLUSTALW is provided within the CLUSTALW algorithm and would be readily appreciated to one of skill in the art of bioinformatics.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred. Polynucleotide variants can be produced for a variety of reasons, e.g., to optimize codon expression for a particular host (change codons in the mRNA to those preferred by a bacterial host such as *E. coli*).

A "composition comprising a given polynucleotide sequence" refers broadly to any composition containing the given polynucleotide sequence. The composition may comprise a dry formulation or an aqueous solution. Compositions comprising the polynucleotide sequence (SEQ ID NO:1) encoding hSLAP-2v3 or hSLAP-2v4 polypeptide (SEQ ID NO:2 or SEQ ID NO:4), or fragments thereof, may be employed as hybridization probes. The probes may be stored in freeze-dried form and may be in association with a stabilizing agent such as a carbohydrate. In hybridizations, the probe may be employed in an aqueous solution containing salts (e.g., NaCl), detergents or surfactants (e.g., SDS), and other components (e.g., Denhardt's solution, dry milk, salmon sperm DNA, and the like).

The term "substantially purified" refers to nucleic acid sequences or amino acid sequences that are removed from their natural environment, i.e., isolated or separated by a variety of means, and are at least 60% free, preferably 75% to 85% free, and most preferably 90% or greater free from other components with which they are naturally associated.

The term "sample", or "biological sample", is meant to be interpreted in its broadest sense. A biological sample suspected of containing nucleic acid encoding the hSLAP-2v3 or hSLAP-2v4 protein, or fragments thereof, or the hSLAP-2v3 or hSLAP-2v4 protein itself, may comprise a body fluid, an extract from cells or tissue, chromosomes isolated from a cell (e.g., a spread of metaphase chromosomes), organelle, or membrane isolated from a cell, a cell, nucleic acid such as genomic DNA (in solution or bound to a solid support such as for Southern analysis), RNA (in solution or bound to a solid support such as for Northern analysis), cDNA (in solution or bound to a solid support), a tissue, a tissue print and the like.

"Transformation" refers to a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and partial bombardment. Such "transformed" cells include stably transformed cells in which the inserted DNA is capable of replication either as an autonomously replicating plasmid or as part of the host chromosome. Transformed cells also include those cells which transiently express the inserted DNA or RNA for limited periods of time.

The term "mimetic" refers to a molecule, the structure of which is developed from knowledge of the structure of the hSLAP-2v3 or hSLAP-2v4 protein, or portions thereof, and as such, is able to affect some or all of the actions of the hSLAP-2v3 or hSLAP-2v4 protein.

The term "portion" with regard to a protein (as in "a portion of a given protein") refers to fragments or segments, for example, peptides, of that protein. The fragments may range in size from four or five amino acid residues to the entire amino acid sequence minus one amino acid. Thus, a protein "comprising at least a portion of the amino acid sequence of SEQ ID NO: 2" encompasses the full-length human hSLAP-2v3 polypeptide, and fragments thereof. Thus, a protein "comprising at least a portion of the amino acid sequence of SEQ ID NO: 4" encompasses the full-length human hSLAP-2v4 polypeptide, and fragments thereof.

The term "antibody" refers to intact molecules as well as fragments thereof, such as Fab, F(ab')$_2$, Fv, which are capable of binding an epitopic or antigenic determinant. Antibodies that bind to hSLAP-2v3 or hSLAP-2v4 polypeptides can be prepared using intact polypeptides or fragments containing small peptides of interest or prepared recombinantly for use as the immunizing antigen. The polypeptide or oligopeptide used to immunize an animal can be derived from the transition of RNA or synthesized chemically, and can be conjugated to a carrier protein, if desired. Commonly used carriers that are chemically coupled to peptides include bovine serum albumin (BSA), keyhole limpet hemocyanin (KLH), and thyroglobulin. The coupled peptide is then used to immunize the animal (e.g, a mouse, a rat, or a rabbit).

The term "humanized" antibody refers to antibody molecules in which amino acids have been replaced in the non-antigen binding regions in order to more closely resemble a human antibody, while still retaining the original binding capability, e.g., as described in U.S. Pat. No. 5,585,089 to C. L. Queen et al.

The term "antigenic determinant" refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding" refer to the interaction between a protein or peptide and a binding molecule, such as an agonist, an antagonist, or an antibody. The interaction is dependent upon the presence of a particular structure (e.g., an antigenic determinant or epitope, or a structural determinant) of the protein that is recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody. In addition, the hSLAP-2v3 or hSLAP-2v4 protein of the present invention contains an SH2/SH3 domain that serves as an interacting region of hSLAP-2v3 or hSLAP-2v4 with other cellular proteins, putative tyrosine residues that may become phosphorylated and could bind to SH2 domains on other cellular proteins and an SH3 binding motif that may serve as a binding domain for other cellular proteins having an SH3 domain.

DESCRIPTION OF THE PRESENT INVENTION

The present invention is based on the discovery of two novel full-length human Src homology 2-/Src homology 3-(SH2/SH3) domain-containing variants of the hSLAP-2 protein, a member of the SLAP family of adapter proteins, referred to as hSLAP-2v3 and hSLAP-2v4. The hSLAP-2 polypeptide, and SLAP proteins, in general, have been shown to be negative regulators of intracellular signal transduction in several cell types, including T-cells. For hSLAP-2 see: co-pending WO 02/42457, filed Nov. 20, 2001 (Bristol-Myers Squibb Company) which is hereby incorporated herein by reference in its entirety, WO 02/42452, published May 30th, 2002; Holland et al (J. Exp. Med., 194 (9):1263-1276 (2001); Pandey et al (J. Biol. Chem., 277(21):19131-19138 (2002), and Loreto et al (Mol. Cell. Biol., 22(12):4241-4255 (2002). For SLAP see: Roche, S. et al., (1998) Src-like adaptor protein (Slap) is a negative regulator of mitogenesis. *Curr. Biol.* 8:975-978; Tang, J. et al., (1999) SLAP, a dimeric adapter protein, plays a functional role in T cell receptor signaling. *Proc. Natl. Acad. Sci. USA* 96:9775-9780; and Sosinowski, T. et al., (2000) Src-like adaptor protein (SLAP) is a negative regulator of T cell receptor signaling. *J. Exp. Med.* 191:463-474).

Polynucleotides and Polypeptides of the Invention

Features of the Polypeptide Encoded by Polynucleotide No: 1

Figure 4:
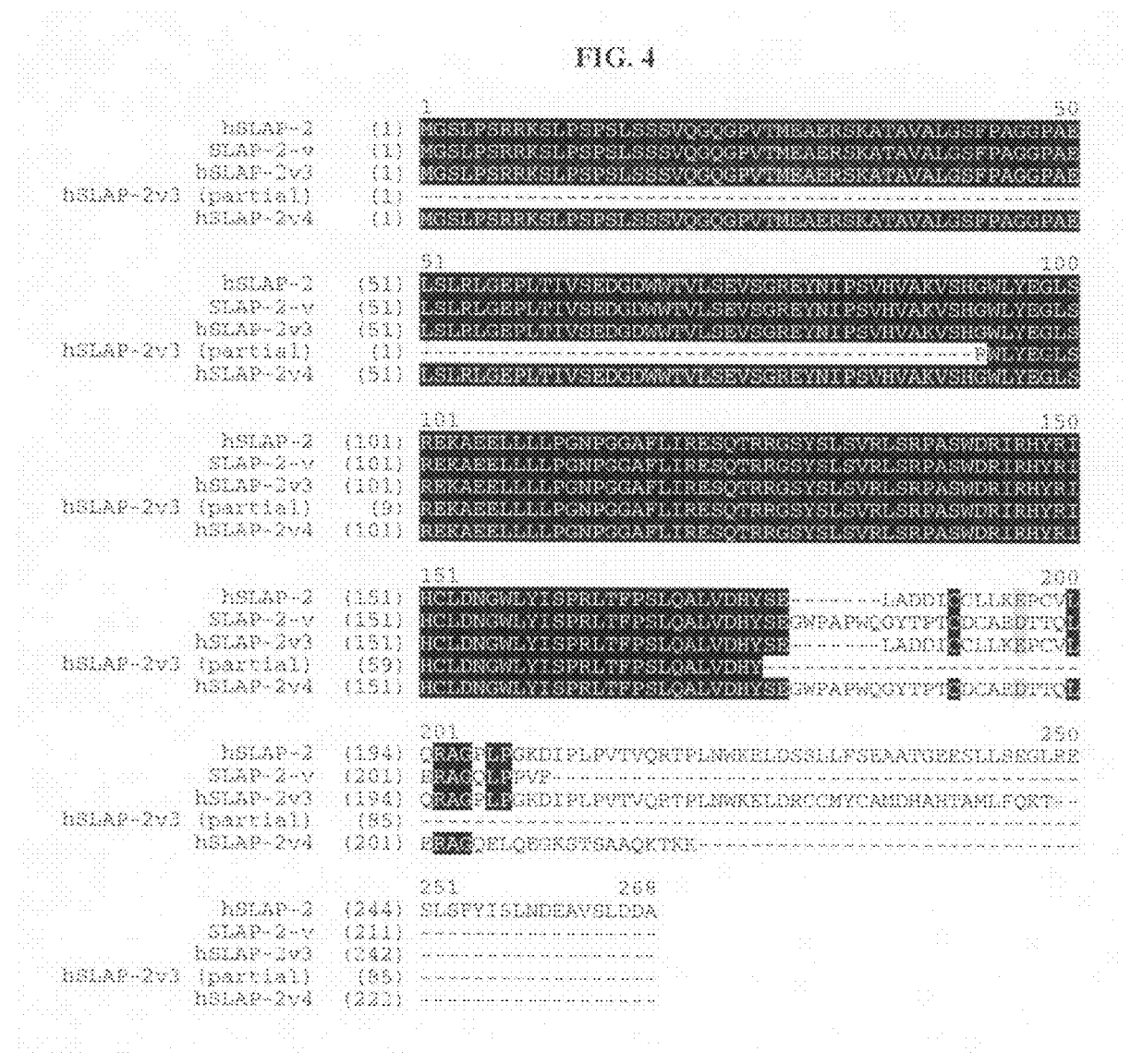

The polypeptide of this polynucleotide provided as SEQ ID NO:2 (FIGS. 1A-B), encoded by the polynucleotide sequence according to SEQ ID NO:1 (FIGS. 1A-B), and/or encoded by the polynucleotide contained within the deposited clone, hSLAP-2v3 (also referred to as BMY_HPP34 variant 1), represents a novel variant of the human hSLAP-2 polypeptide (SEQ ID NO:7), a Src-like adaptor protein that is known to negatively regulate intracellular T-cell signal transduction (see co-pending U.S. Serial 09/988,971, filed Nov. 20, 2001, now U.S. Pat. No. 7,101,686; WO 02/42452, published May 30th, 2002; Holland et al (J. Exp. Med., 194 (9):1263-1276 (2001); Pandey et al (J. Biol. Chem., 277(21): 19131-19138 (2002), and Loreto et al (Mol. Cell. Biol., 22(12):4241-4255 (2002)). An alignment of the hSLAP-2v3 polypeptide with hSLAP-2 is provided in FIG. 4.

The determined nucleotide sequence of the hSLAP-2v3 cDNA in FIGS. 1A-B (SEQ ID NO:1) contains an open reading frame encoding a protein of about 241 amino acid residues, with a deduced molecular weight of about 26.7 kDa. The amino acid sequence of the predicted hSLAP-2v3 polypeptide is shown in FIGS. 1A-B (SEQ ID NO:2).

The hSLAP-2v3 polypeptide retains the SH2 (Src homology 2) domain and the SH3 (Src homology 3) of hSLAP-2 which are both required for its activity. Specifically, the SH3 domain of hSLAP-2v3 is located from about amino acid 35 to about amino acid 90 of SEQ ID NO:2; and the SH2 domain of hSLAP-2v3 is located from about amino acid 94 to about amino acid 176 of SEQ ID NO:2. In this context, the term "about" may be construed to mean 1, 2, 3, 4, 5, 6, 7, 8, 9, or 10 amino acids beyond the N-Terminus and/or C-terminus of the above referenced amino acid locations.

The hSLAP-2v3 polypeptide also contains a c-Cbl binding region in its c-terminus which is thought to be required for the T-cell signal transduction activity of hSLAP-2. The c-Cbl binding region permits hSLAP-2 to bind to E3 ubiquitin ligase c-Cbl, which facilitates the c-Cbl-mediated downregulation of the activated TCR complex which is the likely mechanism for hSLAP-2 mediated T-cell signal transduction activity. Since hSLAP-2v3 retains the c-Cbl domain, it is expected to retain the T-cell signal transduction modulatory activity of hSLAP-2.

The hSLAP-2v3 polypeptide also retains the conserved tyrosine phosphorylation sites of hSLAP-2 as well. The conserved tyrosine phosphorylation sites of hSLAP-2v3 are located at amino acid positions 80, 96, 130, 148, 159, and 176 of SEQ ID NO:2.

The hSLAP-2v3 polypeptide contains Exons 1 to 7 of hSLAP-2 including the Cbl-binding domain and SLAP-2 down-regulation function but then splices to create a different Exon 8 (about 1500 nucleotides downstream) in the 3' untranslated exon of C20orf24/RAB5-interacting protein.

In preferred embodiments, the present invention encompasses a polynucleotide including the start codon, in addition to, the resulting encoded polypeptide of hSLAP-2v3. Specifically, the present invention encompasses the polynucleotide corresponding to nucleotides 29 thru 751 of SEQ ID NO:1, and the polypeptide corresponding to amino acids 1 thru 241 of SEQ ID NO:2. Also encompassed are recombinant vectors comprising said encoding sequence, and host cells comprising said vector.

In preferred embodiments, the present invention encompasses a polynucleotide lacking the initiating start codon, in addition to, the resulting encoded polypeptide of hSLAP-2v3. Specifically, the present invention encompasses the polynucleotide corresponding to nucleotides 32 thru 751 of SEQ ID NO:1, and the polypeptide corresponding to amino acids 2 thru 241 of SEQ ID NO:2. Also encompassed are recombinant vectors comprising said encoding sequence, and host cells comprising said vector.

In preferred embodiments, the present invention also encompasses a polynucleotide that comprises a polypeptide that encodes at least about 222 contiguous amino acids of SEQ ID NO:2. The present invention also encompasses a polynucleotide that comprises at least 666 contiguous nucleotides of SEQ ID NO: 1. Preferably, the polypeptides and/or polypeptides encoded by said polynucleotides retain hSLAP-2 activity. In this context, the term "about" may be construed to mean 1, 2, 3, 4, 5, 6, 7, 8, 9, 10, 11, 12, 13, 14, 15, 16, 17, 18, 19, or 20 amino acids beyond the N-Terminus and/or C-terminus of the above referenced amino acid locations.

Since hSLAP-2v3 represents a variant form of the hSLAP-2, it is expected to share at least some biological activity with hSLAP-2, and in particular, the negative regulation of intracellular T-cell signal transduction of hSLAP-2.

FIGS. 6 and 7 demonstrate that hSLAP-2 is capable of negatively regulating intracellular T-cell signal transduction. FIG. 6 shows the effect of hSLAP-2 on T cell receptor signaling by measuring the level of NFAT activation using an NFAT promoter-luciferase reporter system in cells in which hSLAP-2 was expressed relative to control. As shown, transiently transfected Jurkat/NFAT promoter-luciferase cells with 20 μg and 40 μg of hSLAP-2_GFP or a control_GFP DNA showed marked effects on luciferase activity 40 hours post-transfection and after stimulation with anti-human CD3 antibody for six hours as determined by FACs analysis.

In FIG. 7, hSLAP-2 was found to inhibit anti-human CD3 antibody mediated NFAT promoter activation in a Jurkat cell line. Activation of anti-CD3 triggers an intracellular signaling cascade that leads to the activation of specific nuclear transcription factors, including NFAT. These results are consistent with other findings that show overexpression of SLAP-2 negatively regulates T cell receptor signaling (see Holland, Pandey, Loreto, and McGlade), and in particular that transfection of 40 μg of hSLAP-2 DNA into a T-cell NFAT promoter-luciferase reporter cell system significantly inhibits anti-CD3-induced NFAT promoter activation with a p-value of $1\times10^{10}$. Transfection with 20 ug of hSLAP-2_GFP DNA did not show a significant amount of inhibition when compared to the control.

In FIG. 8, hSLAP-2v3 was found to inhibit anti-human CD3 antibody mediated NFAT promoter activation in a Jurkat cell line at levels comparable to the wild-type hSLAP-2. Activation of anti-CD3 triggers an intracellular signaling cascade that leads to the activation of specific nuclear transcription factors, including NFAT. According, this data confirms the negative regulation of intracellular T-cell and B-cell signal transduction activity of hSLAP-2v3.

The hSLAP-2v3 polynucleotides and polypeptides of the present invention, including modulators and/or fragments thereof, have uses that include detecting, prognosing, diagnosing, treating, preventing, and/or ameliorating the following diseases and/or disorders: disorders associated with aberrant T-cell intracellular signal transduction, disorders associated with aberrant hSLAP-2 expression and/or activity, disorders associated with aberrant ZAP-70 regulation, disorders associated with aberrant E3 ubiquitin ligase c-Cbl regulation, disorders associated with aberrant TCR-mediated NFAT activation regulation, disorders associated with aberrant T-cell receptor activation, proliferative immune cell disorders or diseases, B- or T-cell tumors, lymphomas, leukemias, disorders or diseases associated with hyperactive cells, particularly cells of immunological origin, including B- and T-lymphocytes, monocytes, mast cells and the like; immunological or inflammatory disorders such as rheumatoid arthritis, osteoarthritis, psoriasis, rhinitis, allergies—particularly those involving hyperactivity of B-cells and T-cells, or other immune cells, such as mast cells or eosinophils, rejection of organ or tissue transplants, inflammatory bowel disorders; Crohn's, ulcerative colitis, autoimmune diseases such as systemic lupus erythematosus and multiple sclerosis; pulmonary diseases including asthma and chronic obstructive pulmonary disorder; and cancer. In addition, the hSLAP-2v3 polynucleotide and polypeptide are useful for determining those cellular signaling molecules which associate with hSLAP-2v3 and which provide critical signals for cell activation, preferably, T-cell activation.

The hSLAP-2v3 polynucleotides and polypeptides, including fragments and modulators thereof, may have uses which include, either directly or indirectly, for inhibiting immune responses.

The hSLAP-2v3 polynucleotides and polypeptides, including fragments and/or antagonists thereof, may have uses which include identification of modulators of hSLAP-2v3 function including antibodies (for detection or neutralization), naturally-occurring modulators and small molecule modulators. Antibodies to domains of the hSLAP-2v3 protein could be used as diagnostic agents of inflammatory conditions in patients, are useful in monitoring the activation of signal transduction pathways, and can be used as a biomarker for the involvement of hSLAP-2v3 in disease states.

hSLAP-2v3 polypeptides and polynucleotides have additional uses which include diagnosing diseases related to the over and/or under expression of hSLAP-2v3 by identifying mutations in the hSLAP-2v3 gene by using hSLAP-2v3 sequences as probes or by determining hSLAP-2v3 protein or mRNA expression levels. hSLAP-2v3 polypeptides may be useful for screening compounds that affect the activity of the protein. hSLAP-2v3 peptides can also be used for the generation of specific antibodies and as bait in yeast two hybrid screens to find proteins the specifically interact with hSLAP-2v3 (described elsewhere herein).

In preferred embodiments, the following N-terminal hSLAP-2v3 deletion polypeptides are encompassed by the present invention: M1-T241, G2-T241, S3-T241, L4-T241, P5-T241, S6-T241, R7-T241, R8-T241, K9-T241, S10-T241, L11-T241, P12-T241, S13-T241, P14-T241, S15-T241, L16-T241, S17-T241, S18-T241, S19-T241, V20-T241, Q21-T241, G22-T241, Q23-T241, G24-T241, P25-T241, V26-T241, T27-T241, M28-T241, E29-T241, A30-T241, E31-T241, R32-T241, S33-T241, K34-T241, A35-T241, T241, T36-T241, A37-T241, V38-T241, A39-T241, L40-T241, G41-T241, S42-T241, F43-T241, P44-T241, A45-T241, G46-T241, G47-T241, P48-T241, A49-T241, E50-T241, L51-T241, S52-T241, L53-T241, R54-T241, L55-T241, G56-T241, E57-T241, P58-T241, L59-T241, T60-T241, 161-T241, V62-T241, S63-T241, E64-T241, D65-T241, G66-T241, D67-T241, W68-T241, W69-T241, T70-T241, V71-T241, L72-T241, S73-T241, E74-T241, V75-T241, S76-T241, G77-T241, R78-T241, E79-T241, Y80-T241, N81-T241, 182-T241, P83-T241, S84-T241, V85-T241, H86-T241, V87-T241, A88-T241, K89-T241, V90-T241, S91-T241, H92-T241, G93-T241, W94-T241, L95-T241, Y96-T241, E97-T241, G98-T241, L99-T241, S100-T241, R101-T241, E102-T241, K103-T241, A104-T241, E105-T241, E106-T241, L107-T241, L108-T241, L109-T241, L110-T241, P111-T241, G112-T241, N113-T241, P114-T241, G115-T241, G116-T241, A117-T241, F118-T241, L119-T241, I120-T241, R121-T241, E122-T241, S123-T241, Q124-T241, T125-T241, R126-T241, R127-T241, G128-T241, S129-T241, Y130-T241, S131-T241, L132-T241, S133-T241, V134-T241, R135-T241, L136-T241, 5137-T241, R138-T241, P139-T241, A140-T241, S141-T241, W142-T241, D143-T241, R144-T241, I145-T241, R146-T241, H147-T241, Y148-T241, R149-T241, I150-T241, H151-T241, C152-T241, L153-T241, D154-T241, N155-T241, G156-T241, W157-T241, L158-T241, Y159-T241, I160-T241, 5161-T241, P162-T241, R163-T241, L164-T241, T165-T241, F166-T241, P167-T241, S168-T241, L169-T241, Q170-T241, A171-T241, L172-T241, V173-T241, D174-T241, H175-T241, Y176-T241, S177-T241, E178-T241, L179-T241, A180-T241, D181-T241, D182-T241, I183-T241, C184-T241, C185-T241, L186-T241, L187-T241, K188-T241, E189-T241, P190-T241, C191-T241, V192-T241, L193-T241, Q194-T241, R195-T241, A196-T241, G197-T241, P198-T241, L199-T241, P200-T241, G201-T241, K202-T241, D203-T241, I204-T241, P205-T241, L206-T241, P207-T241, V208-T241, T209-T241, V210-T241, Q211-T241, R212-T241, T213-T241, P214-T241, L215-T241, N216-T241, W217-T241, K218-T241, E219-T241, L220-T241, D221-T241, R222-T241, C223-T241, C224-T241, M225-T241, Y226-T241, C227-T241, A228-T241, M229-T241, D230-T241, H231-T241, A232-T241, H233-T241, T234-T241, and/or A235-T241 of SEQ ID NO:2. Polynucleotide sequences encoding these polypeptides are also provided. The present invention also encompasses the use of these N-terminal hSLAP-2v3 deletion polypeptides as immunogenic and/or antigenic epitopes as described elsewhere herein.

In preferred embodiments, the following C-terminal hSLAP-2v3 deletion polypeptides are encompassed by the present invention: M1-T241, M1-K240, M1-Q239, M1-F238, M1-L237, M1-M236, M1-A235, M1-T234, M1-H233, M1-A232, M1-H231, M1-D230, M1-M229, M1-A228, M1-C227, M1-Y226, M1-M225, M1-C224, M1-C223, M1-R222, M1-D221, M1-L220, M1-E219, M1-K218, M1-W217, M1-N216, M1-L215, M1-P214, M1-T213, M1-R212, M1-Q211, M1-V210, M1-T209, M1-V208, M1-P207, M1-L206, M1-P205, M1-I204, M1-D203, M1-K202, M1-G201, M1-P200, M1-L199, M1-P198, M1-G197, M1-A196, M1-R195, M1-Q194, M1-L193, M1-V192, M1-C191, M1-P190, M1-E189, M1-K188, M1-L187, M1-L186, M1-C185, M1-C184, M1-I183, M1-D182, M1-D181, M1-A180, M1-L179, M1-E178, M1-S177, M1-Y176, M1-H175, M1-D174, M1-V173, M1-L172, M1-A171, M1-Q170, M1-L169, M1-S168, M1-P167, M1-F166, M1-T165, M1-L164, M1-R163, M1-P162, M1-S161, M1-I160, M1-Y159, M1-L158, M1-W157, M1-G156, M1-N155, M1-D154, M1-L153, M1-C152, M1-H151, M1-I150, M1-R149, M1-Y148, M1-H147, M1-R146, M1-I145, M1-R144, M1-D143, M1-W142, M1-S141, M1-A140, M1-P139, M1-R138, M1-S137, M1-L136, M1-R135, M1-V134, M1-S133, M1-L132, M1-S131, M1-Y130, M1-S129, M1-G128, M1-R127, M1-R126, M1-T125, M1-Q124, M1-S123, M1-E122, M1-R121, M1-I120, M1-L119, M1-F118, M1-A117, M1-G116, M1-G115, M1-P114, M1-N113, M1-G112, M1-P111, M1-L110, M1-L109, M1-L108, M1-L107, M1-E106, M1-E105, M1-A104, M1-K103, M1-E102, M1-R101, M1-S100, M1-L99, M1-G98, M1-E97, M1-Y96, M1-L95, M1-W94, M1-G93, M1-H92, M1-S91, M1-V90, M1-K89, M1-A88, M1-V87, M1-H86, M1-V85, M1-S84, M1-P83, M1-I82, M1-N81, M1-Y80, M1-E79, M1-R78, M1-G77, M1-S76, M1-V75, M1-E74, M1-S73, M1-L72, M1-V71, M1-T70, M1-W69, M1-W68, M1-D67, M1-G66, M1-D65, M1-E64, M1-S63, M1-V62, M1-I61, M1-T60, M1-L59, M1-P58, M1-E57, M1-G56, M1-L55, M1-R54, M1-L53, M1-S52, M1-L51, M1-E50, M1-A49, M1-P48, M1-G47, M1-G46, M1-A45, M1-P44, M1-F43, M1-S42, M1-G41, M1-L40, M1-A39, M1-V38, M1-A37, M1-T36, M1-A35, M1-K34, M1-S33, M1-R32, M1-E31, M1-A30, M1-E29, M1-M28, M1-T27, M1-V26, M1-P25, M1-G24, M1-Q23, M1-G22, M1-Q21, M1-V20, M1-S19, M1-S18, M1-S17, M1-L16, M1-S15, M1-P14, M1-S13, M1-P12, M1-S10, M1-K9, M1-R8, and/or M1-R7 of SEQ ID NO:2. Polynucleotide sequences encoding these polypeptides are also provided. The present invention also encompasses the use of these C-terminal hSLAP-2v3 deletion polypeptides as immunogenic and/or antigenic epitopes as described elsewhere herein.

Alternatively, preferred polypeptides of the present invention may comprise polypeptide sequences corresponding to, for example, internal regions of the hSLAP-2v3 polypeptide (e.g., any combination of both N- and C-terminal hSLAP-2v3 polypeptide deletions) of SEQ ID NO:2. For example, internal regions could be defined by the equation: amino acid NX to amino acid CX, wherein NX refers to any N-terminal deletion polypeptide amino acid of hSLAP-2v3 (SEQ ID NO:2), and where CX refers to any C-terminal deletion polypeptide amino acid of hSLAP-2v3 (SEQ ID NO:2). Polynucleotides encoding these polypeptides are also provided. The present invention also encompasses the use of these polypeptides as an immunogenic and/or antigenic epitope as described elsewhere herein.

The present invention also encompasses immunogenic and/or antigenic epitopes of the hSLAP-2v3 polypeptide.

Many polynucleotide sequences, such as EST sequences, are publicly available and accessible through sequence databases. Some of these sequences are related to SEQ ID NO:1 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 905 of SEQ ID NO:1, b is an integer between 15 to 919, where both a and b correspond to the positions of nucleotide residues shown in SEQ ID NO:1, and where b is greater than or equal to a+14.

Features of the Polypeptide Encoded by Polynucleotide No: 2

The polypeptide of this polynucleotide provided as SEQ ID NO:4 (FIGS. 2A-B), encoded by the polynucleotide sequence according to SEQ ID NO:3 (FIGS. 2A-B), and/or encoded by the polynucleotide contained within the deposited clone, hSLAP-2v4 (also referred to as BMY_HPP34 variant 2), represents a novel variant of the human hSLAP-2 polypeptide (SEQ ID NO:7), a Src-like adaptor protein that is known to negatively regulate intracellular T-cell signal transduction (see co-pending U.S. Ser. No. 09/988,971, filed Nov. 20, 2001, now U.S. Pat. No. 7,101,686; WO 02/42452, published May 30th, 2002; Holland et al (J. Exp. Med., 194 (9):1263-1276 (2001); Pandey et al (J. Biol. Chem., 277(21): 19131-19138 (2002), and Loreto et al (Mol. Cell. Biol., 22(12):4241-4255 (2002)). An alignment of the hSLAP-2v4 polypeptide with hSLAP-2 is provided in FIG. 4.

The determined nucleotide sequence of the hSLAP-2v4 cDNA in FIGS. 2A-B (SEQ ID NO:3) contains an open reading frame encoding a protein of about 221 amino acid residues, with a deduced molecular weight of about 24.3 kDa. The amino acid sequence of the predicted hSLAP-2v4 polypeptide is shown in FIGS. 2A-B (SEQ ID NO:4).

The hSLAP-2v4 polypeptide retains the SH2 (Src homology 2) domain and the SH3 (Src homology 3) of hSLAP-2 which are both required for its activity. Specifically, the SH3 domain of hSLAP-2v4 is located from about amino acid 35 to about amino acid 90 of SEQ ID NO:4; and the SH2 domain of hSLAP-2v4 is located from about amino acid 94 to about amino acid 176 of SEQ ID NO:4. In this context, the term "about" may be construed to mean 1, 2, 3, 4, 5, 6, 7, 8, 9, or 10 amino acids beyond the N-Terminus and/or C-terminus of the above referenced amino acid locations.

The hSLAP-2v4 polypeptide also retains the conserved tyrosine phosphorylation sites of hSLAP-2 as well. The conserved tyrosine phosphorylation sites of hSLAP-2v4 are located at amino acid positions 80, 96, 130, 148, 159, and 176 of SEQ ID NO:4.

Unlike hSLAP-2v3, the hSLAP-2v4 polypeptide does not contain a c-Cbl binding region in its c-terminus. The c-Cbl binding region is thought to be required for the T-cell signal transduction activity of hSLAP-2. Since hSLAP-2v4 lacks a complete c-Cbl domain, it was expected to lack the T-cell signal transduction modulatory activity of hSLAP-2. A similar variant of hSLAP-2 lacking a complete c-Cbl domain has been described by Loreto et al. (Oncogene, 22(2):266-273 (2003)) and referred to as SLAP-2-v (SEQ ID NO:14). Like hSLAP-2, SLAP-2-v retained the ability to bind to 70 and 72 kDa proteins (the 70 kDa protein purportedly being ZAP-70), but had reduced capacity (i.e., about 60% reduction) to inhibit TCR-mediated NFAT activation relative to hSLAP-2.

The hSLAP-2v4 polypeptide contains Exons 1 to 7 of SLAP-2-v (does not retain the Cbl-binding domain) but then splices to create a different Exon 8 (~7000 nucleotides downstream) in an intron of C20orf24/RAB5-interacting protein.

The hSLAP-2v4 polypeptide was thus expected to have at least reduced capacity to bind c-Cbl and therefore have at least a reduced ability to inhibit TCR-mediated NFAT activation. In addition, it was expected that hSLAP-2v4 may function as a decoy receptor by sequestering ZAP-70 and thus potentiating TCR-mediated NFAT activation since it would be expected to retain the ability of hSLAP-2 to bind to ZAP-70, though have reduced ability to regulate its expression.

However, contrary to the teachings of Loreto et al. for SLAP-2-v, hSLAP-2v4 was found to inhibit anti-human CD3 antibody mediated NFAT promoter activation in a Jurkat cell line at levels comparable to the wild-type hSLAP-2 (see FIG. 8). In fact, hSLAP-2v4 was found to have only a slightly increased ability to negatively regulate intracellular cell signal transduction activity relative to hSLAP-2 and hSLAP-2v3. Activation of anti-CD3 triggers an intracellular signaling cascade that leads to the activation of specific nuclear transcription factors, including NFAT. According, this data confirms the negative regulation of intracellular T-cell and B-cell signal transduction activity of hSLAP-2v4.

Since hSLAP-2v4 represents a variant form of the hSLAP-2, it is expected to share at least some biological activity with hSLAP-2, and in particular, the negative regulation of intracellular T-cell signal transduction of hSLAP-2, albeit at a reduced level.

In preferred embodiments, the present invention encompasses a polynucleotide including the start codon, in addition to, the resulting encoded polypeptide of hSLAP-2v4. Specifically, the present invention encompasses the polynucleotide corresponding to nucleotides 274 thru 936 of SEQ ID NO:3, and the polypeptide corresponding to amino acids 1 thru 221 of SEQ ID NO:4. Also encompassed are recombinant vectors comprising said encoding sequence, and host cells comprising said vector.

In preferred embodiments, the present invention encompasses a polynucleotide lacking the initiating start codon, in addition to, the resulting encoded polypeptide of hSLAP-2v4. Specifically, the present invention encompasses the polynucleotide corresponding to nucleotides 277 thru 936 of SEQ ID NO:3, and the polypeptide corresponding to amino acids 2 thru 221 of SEQ ID NO:4. Also encompassed are recombinant vectors comprising said encoding sequence, and host cells comprising said vector.

In preferred embodiments, the present invention also encompasses a polynucleotide that comprises a polypeptide that encodes at least about 179 contiguous amino acids of SEQ ID NO:4. The present invention also encompasses a polynucleotide that comprises at least 537 contiguous nucleotides of SEQ ID NO:3. Preferably, the polypeptides and/or polypeptides encoded by said polynucleotides retain hSLAP-2 activity. In this context, the term "about" may be construed to mean 1, 2, 3, 4, 5, 6, 7, 8, 9, 10, 11, 12, 13, 14, 15, 16, 17, 18, 19, or 20 amino acids beyond the N-Terminus and/or C-terminus of the above referenced amino acid locations.

The hSLAP-2v4 polynucleotides and polypeptides of the present invention, including modulators and/or fragments thereof, have uses that include detecting, prognosing, diagnosing, treating, preventing, and/or ameliorating the following diseases and/or disorders: disorders associated with aberrant T-cell intracellular signal transduction, disorders associated with aberrant hSLAP-2 expression and/or activity, disorders associated with aberrant ZAP-70 regulation, disorders associated with aberrant E3 ubiquitin ligase c-Cbl regulation, disorders associated with aberrant TCR-mediated NFAT activation regulation, disorders associated with aberrant T-cell receptor activation, proliferative immune cell disorders or diseases, B- or T-cell tumors, lymphomas, leukemias, disorders or diseases associated with hyperactive cells, particularly cells of immunological origin, including B- and T-lymphocytes, monocytes, mast cells and the like; immunological or inflammatory disorders such as rheumatoid arthritis, osteoarthritis, psoriasis, rhinitis, allergies—particularly those involving hyperactivity of B-cells and T-cells, or other immune cells, such as mast cells or eosinophils, rejection of organ or tissue transplants, inflammatory bowel disorders; Crohn's, ulcerative colitis, autoimmune diseases such as systemic lupus erythematosus and multiple sclerosis; pulmonary diseases including asthma and chronic obstructive pulmonary disorder; and cancer. In addition, the hSLAP-2v4 polynucleotide and polypeptide are useful for determining those cellular signaling molecules which associate with hSLAP-2v4 and which provide critical signals for cell activation, preferably, T-cell activation.

The hSLAP-2v4 polynucleotides and polypeptides, including fragments and modulators thereof, may have uses which include, either directly or indirectly, for inhibiting immune responses.

The hSLAP-2v4 polynucleotides and polypeptides, including fragments and/or antagonists thereof, may have uses which include identification of modulators of hSLAP-2v4 function including antibodies (for detection or neutralization), naturally-occurring modulators and small molecule modulators. Antibodies to domains of the hSLAP-2v4 protein could be used as diagnostic agents of inflammatory conditions in patients, are useful in monitoring the activation of signal transduction pathways, and can be used as a biomarker for the involvement of hSLAP-2v4 in disease states.

hSLAP-2v4 polypeptides and polynucleotides have additional uses which include diagnosing diseases related to the over and/or under expression of hSLAP-2v4 by identifying mutations in the hSLAP-2v4 gene by using hSLAP-2v4 sequences as probes or by determining hSLAP-2v4 protein or mRNA expression levels. hSLAP-2v4 polypeptides may be useful for screening compounds that affect the activity of the protein. hSLAP-2v4 peptides can also be used for the generation of specific antibodies and as bait in yeast two hybrid screens to find proteins the specifically interact with hSLAP-2v4 (described elsewhere herein).

In preferred embodiments, the following N-terminal hSLAP-2v4 deletion polypeptides are encompassed by the present invention: M1-K221, G2-K221, S3-K221, L4-K221, P5-K221, S6-K221, R7-K221, R8-K221, K9-K221, S10-K221, L11-K221, P12-K221, S13-K221, P14-K221, S15-K221, L16-K221, S17-K221, S18-K221, S19-K221, V20-K221, Q21-K221, G22-K221, Q23-K221, G24-K221, P25-K221, V26-K221, T27-K221, M28-K221, E29-K221, A30-K221, E31-K221, R32-K221, S33-K221, K34-K221, A35-K221, T36-K221, A37-K221, V38-K221, A39-K221, L40-K221, G41-K221, S42-K221, F43-K221, P44-K221, A45-K221, G46-K221, G47-K221, P48-K221, A49-K221, E50-K221, L51-K221, S52-K221, L53-K221, R54-K221, L55-K221, G56-K221, E57-K221, P58-K221, L59-K221, T60-K221, I61-K221, V62-K221, S63-K221, E64-K221, D65-K221, G66-K221, D67-K221, W68-K221, W69-K221, T70-K221, V71-K221, L72-K221, S73-K221, E74-K221, V75-K221, S76-K221, G77-K221, R78-K221, E79-K221, Y80-K221, N81-K221, I82-K221, P83-K221, S84-K221, V85-K221, H86-K221, V87-K221, A88-K221, K89-K221, V90-K221, S91-K221, H92-K221, G93-K221, W94-K221, L95-K221, Y96-K221, E97-K221, G98-K221, L99-K221, S100-K221, R101-K221, E102-K221, K103-K221, A104-K221, E105-K221, E106-K221, L107-K221, L108-K221, L109-K221, L110-K221, P111-K221, G112-K221, N113-K221, P114-K221, G115-K221, G116-K221, A117-K221, F118-K221, L119-K221, I120-K221, R121-K221, E122-K221, S123-K221, Q124-K221, T125-K221, R126-K221, R127-K221, G128-K221, S129-K221, Y130-K221, S131-K221, L132-K221, S133-K221, V134-K221, R135-K221, L136-K221, S137-K221, R138-K221, P139-K221, A140-K221, S141-K221, W142-K221, D143-K221, R144-K221, I145-K221, R146-K221, H147-K221, Y148-K221, R149-K221, I150-K221, H151-K221, C152-K221, L153-K221, D154-K221, N155-K221, G156-K221, W157-K221, L158-K221, Y159-K221, I160-K221, S161-K221, P162-K221, R163-K221, L164-K221, T165-K221, F166-K221, P167-K221, S168-K221, L169-K221, Q170-K221, A171-K221, L172-K221, V173-K221, D174-K221, H175-K221, Y176-K221, S177-K221, E178-K221, G179-K221, W180-K221, P181-K221, A182-K221, P183-K221, W184-K221, Q185-K221, G186-K221, Y187-K221, T188-K221, P189-K221, T190-K221, C191-K221, D192-K221, C193-K221, A194-K221, E195-K221, D196-K221, T197-K221, T198-K221, Q199-K221, L200-K221, E201-K221, R202-K221, A203-K221, G204-K221, Q205-K221, E206-K221, L207-K221, Q208-K221, E209-K221, G210-K221, K211-K221, S212-K221, T213-K221, S214-K221, and/or A215-K221 of SEQ ID NO:4. Polynucleotide sequences encoding these polypeptides are also provided. The present invention also encompasses the use of these N-terminal hSLAP-2v4 deletion polypeptides as immunogenic and/or antigenic epitopes as described elsewhere herein.

In preferred embodiments, the following C-terminal hSLAP-2v4 deletion polypeptides are encompassed by the present invention: M1-K221, M1-K220, M1-T219, M1-K218, M1-Q217, M1-A216, M1-A215, M1-S214, M1-T213, M1-S212, M1-K211, M1-G210, M1-E209, M1-Q208, M1-L207, M1-E206, M1-Q205, M1-G204, M1-A203, M1-R202, M1-E201, M1-L200, M1-Q199, M1-T198, M1-T197, M1-D196, M1-E195, M1-A194, M1-C193, M1-D192, M1-C191, M1-T190, M1-P189, M1-T188, M1-Y187, M1-G186, M1-Q185, M1-W184, M1-P183, M1-A182, M1-P181, M1-W180, M1-G179, M1-E178, M1-S177, M1-Y176, M1-H175, M1-D174, M1-V173, M1-L172, M1-A171, M1-Q170, M1-L169, M1-S168, M1-P167, M1-F166, M1-T165, M1-L164, M1-R163, M1-P162, M1-S161, M1-I160, M1-Y159, M1-L158, M1-W157, M1-G156, M1-N155, M1-D154, M1-L153, M1-C152, M1-H151, M1-I150, M1-R149, M1-Y148, M1-H147, M1-R146, M1-I145, M1-R144, M1-D143, M1-W142, M1-S141, M1-A140, M1-P139, M1-R138, M1-S137, M1-L136, M1-R135, M1-V134, M1-S133, M1-L132, M1-S131, M1-Y130, M1-S129, M1-G128, M1-R127, M1-R126, M1-T125, M1-Q124, M1-S123, M1-E122, M1-R121, M1-I120, M1-L119, M1-F118, M1-A117, M1-G116, M1-G115, M1-P114, M1-N113, M1-G112, M1-P111, M1-L110, M1-L109, M1-L108, M1-L107, M1-E106, M1-E105, M1-A104, M1-K103, M1-E102, M1-R101, M1-S100, M1-L99, M1-G98, M1-E97, M1-Y96, M1-L95, M1-W94, M1-G93, M1-H92, M1-S91, M1-V90, M1-K89, M1-A88, M1-V87, M1-H86, M1-V85, M1-S84, M1-P83, M1-I82, M1-N81, M1-Y80, M1-E79, M1-R78, M1-G77, M1-S76, M1-V75, M1-E74, M1-S73, M1-L72, M1-V71, M1-T70, M1-W69, M1-W68, M1-D67, M1-G66, M1-D65, M1-E64, M1-S63, M1-V62, M1-I61, M1-T60, M1-L59, M1-P58, M1-E57, M1-G56, M1-L55, M1-R54, M1-L53, M1-S52, M1-L51, M1-E50, M1-A49, M1-P48, M1-G47, M1-G46, M1-A45, M1-P44, M1-F43, M1-S42, M1-G41, M1-L40, M1-A39, M1-V38, M1-A37, M1-T36, M1-A35, M1-K34, M1-S33, M1-R32, M1-E31, M1-A30, M1-E29, M1-M28, M1-T27, M1-V26, M1-P25, M1-G24, M1-Q23, M1-G22, M1-Q21, M1-V20, M1-S19, M1-S18, M1-S17, M1-L16, M1-S15, M1-P14, M1-S13, M1-P12, M1-L11, M1-S10, M1-K9, M1-R8, and/or M1-R7 of SEQ ID NO:4. Polynucleotide sequences encoding these polypeptides are also provided. The present invention also encompasses the use of these C-terminal hSLAP-2v4 deletion polypeptides as immunogenic and/or antigenic epitopes as described elsewhere herein.

Alternatively, preferred polypeptides of the present invention may comprise polypeptide sequences corresponding to, for example, internal regions of the hSLAP-2v4 polypeptide (e.g., any combination of both N- and C-terminal hSLAP-2v4 polypeptide deletions) of SEQ ID NO:4. For example, internal regions could be defined by the equation: amino acid NX to amino acid CX, wherein NX refers to any N-terminal deletion polypeptide amino acid of hSLAP-2v4 (SEQ ID NO:4), and where CX refers to any C-terminal deletion polypeptide amino acid of hSLAP-2v4 (SEQ ID NO:4). Polynucleotides encoding these polypeptides are also provided. The present invention also encompasses the use of these polypeptides as an immunogenic and/or antigenic epitope as described elsewhere herein.

The present invention also encompasses immunogenic and/or antigenic epitopes of the hSLAP-2v4 polypeptide.

Many polynucleotide sequences, such as EST sequences, are publicly available and accessible through sequence databases. Some of these sequences are related to SEQ ID NO:3 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 1442 of SEQ ID NO:3, b is an integer between 15 to 1456, where both a and b correspond to the positions of nucleotide residues shown in SEQ ID NO:3, and where b is greater than or equal to a+14.

TABLE 1

| Gene No. | CDNA CloneID | ATCC ® Deposit No. and Date | Vector | NT SEQ ID. No. | Total NT Seq of Clone | 5' NT of Start Codon of ORF | 3' NT of ORF | AA Seq ID No. | Total AA of ORF |
|---|---|---|---|---|---|---|---|---|---|
| 1. | hSLAP-2v3 (also referred to as BMY_HPP34 variant 1) | PTA-7622 May 10, 2006 | N/A | 1 | 919 | 29 | 751 | 2 | 241 |
| 2. | hSLAP-2v4 (also referred to as BMY_HPP34 variant 2) | PTA-7622 May 10, 2006 | N/A | 1 | 1456 | 274 | 936 | 2 | 221 |

Variants of the hSLAP-2 polypeptide are also encompassed by the present invention. A preferred hSLAP-2 variant has at least 75 to 80%, more preferably at least 85 to 90%, and even more preferably at least 90% amino acid sequence identity to the amino acid sequence (SEQ ID NO:2) disclosed herein, and which retains at least one biological, immunological, or other functional characteristic or activity of the hSLAP-2 polypeptide. Most preferred is a variant having at least 95% amino acid sequence identity to the amino acid sequence set forth in SEQ ID NO:2. An amino acid sequence variant of the hSLAP-2v3 and hSLAP-2-v2 polypeptides can be categorized into one or more of three classes: substitutional, insertional, or deletional variants. Such variants are typically prepared by site-specific mutagenesis of nucleotides in the DNA encoding the hSLAP-2v3 and hSLAP-2-v2 polypeptides, using cassette or PCR mutagenesis, or other techniques that are well known and practiced in the art, to produce DNA encoding the variant. Thereafter, the DNA is expressed in recombinant cell culture as described herein. Variant hSLAP-2v3 and hSLAP-2-v2 polypeptides fragments having up to about 100-150 residues may be prepared by in vitro synthesis using conventional techniques.

Amino acid sequence variants are characterized by the predetermined nature of the variation, a feature that sets them apart from naturally occurring allelic or interspecies variations of the hSLAP-2v3 and hSLAP-2-v2 polypeptides amino acid sequence. The variants typically exhibit the same qualitative biological activity as that of the naturally occurring analogue, although variants can also be selected having modified characteristics. While the site or region for introducing an amino acid sequence variation is predetermined, the mutation per se need not be predetermined. For example, in order to optimize the performance of a mutation at a given site, random mutagenesis may be performed at the target codon or region, and the expressed hSLAP-2v3 and hSLAP-2-v2 polypeptide variants screened for the optimal combination of desired activity. Techniques for making substitution mutations at predetermined sites in DNA having a known sequence are well known, for example, M13 primer mutagenesis and PCR mutagenesis. Screening of the mutants is accomplished using assays of hSLAP-2v3 and hSLAP-2-v2 polypeptides protein activities, for example, for binding domain mutations, competitive binding studies may be carried out.

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1-5,5-10, 5-25, 5-50, 10-50 or 50-150, conservative amino acid substitutions are preferable.

Preferred deletion and/or substitution variants include the deletion or modification of one or more of the characteristic domains of the hSLAP-2v3 and hSLAP-2v4 polypeptides, i.e., the proline-rich regions, or the SH2/SH3 domains.

Substitutions, deletions, insertions, or any combination thereof, may be used to arrive at a final hSLAP-2v3 and hSLAP-2v4 derivative. Generally, these changes affect only a few amino acids to minimize the alteration of the molecule. However, larger changes may be tolerated in certain circumstances. When small alterations in the characteristics of the hSLAP-2v3 and hSLAP-2v4 polypeptides are desired or warranted, substitutions are generally made in accordance with the following table:

TABLE 2

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Table 2. For example, substitutions may be made which more significantly affect the structure of the polypeptide backbone in the area of the alteration, for example, the alpha-helical, or beta-sheet structure; the charge or hydrophobicity of the molecule at the target site; or the bulk of the side chain. The substitutions which generally are expected to produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl, or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) a residue that does not have a side chain, e.g., glycine.

While hSLAP-2v3 and hSLAP-2v4 variants ordinarily exhibit the same qualitative biological activity or function, and elicit the same immune response, as the naturally occurring analogue, the variants are also selected to modify the characteristics of the hSLAP-2v3 and hSLAP-2v4 polypeptides as needed. Alternatively, the variant may be designed such that the biological activity of the hSLAP-2v3 and hSLAP-2v4 polypeptides is altered. For example, any or all of the domains may be altered, i.e., the SH2 and/or SH3 regions, and/or the amino- and carboxy-terminal regions outside of the SH2 and SH3 domains. For example, one or more of the tyrosine phosphorylation sites may be altered.

In another embodiment, the present invention encompasses polynucleotides which encode the hSLAP-2v3 and hSLAP-2v4 polypeptides. Accordingly, any nucleic acid sequence which encodes the amino acid sequence of the hSLAP-2v3 and hSLAP-2v4 polypeptides can be used to produce recombinant molecules that express hSLAP-2v3 and hSLAP-2v4 polypeptides. In a particular embodiment, the present invention encompasses the hSLAP-2v3 and hSLAP-2v4 polynucleotides comprising the nucleic acid sequence of SEQ ID NO:1 or SEQ ID NO:3 and as shown in FIGS. 1A-B or FIGS. 3A-B. More particularly, the present invention provides the cloned full-length hSLAP-2v3 or hSLAP-2v4 cDNAs, deposited at the American Type Culture Collection (ATCC®), 10801 University Boulevard, Manassas, Va. 20110-2209 on May 10, 2006 and under ATCC® Accession No. PTA-7622 according to the terms of the Budapest Treaty.

As will be appreciated by the skilled practitioner in the art, the degeneracy of the genetic code results in the production of numerous nucleotide sequences encoding the hSLAP-2v3 and hSLAP-2v4 polypeptides of the present invention. Some of the sequences bear minimal homology to the nucleotide sequences of any known and naturally occurring gene. Accordingly, the present invention contemplates each and every possible variation of nucleotide sequence that could be made by selecting combinations based on possible codon choices. These combinations are made in accordance with the standard triplet genetic code as applied to the nucleotide sequence of naturally occurring hSLAP-2v3 and hSLAP-2v4, and all such variations are to be considered as being specifically disclosed.

Although nucleotide sequences which encode the hSLAP-2v3 and hSLAP-2v4 polypeptides and its variants are preferably capable of hybridizing to the nucleotide sequence of the naturally occurring hSLAP-2v3 and hSLAP-2v4 polypeptides under appropriately selected conditions of stringency, it may be advantageous to produce nucleotide sequences encoding the hSLAP-2v3 and hSLAP-2v4 polypeptides, or its derivatives, which possess a substantially different codon usage. Codons may be selected to increase the rate at which expression of the peptide/polypeptide occurs in a particular prokaryotic or eukaryotic host in accordance with the frequency with which particular codons are utilized by the host, for example, in plant cells or yeast cells or amphibian cells. Other reasons for substantially altering the nucleotide sequence encoding the hSLAP-2v3 and hSLAP-2v4 polypeptides, and its derivatives, without altering the encoded amino acid sequences include the production of mRNA transcripts having more desirable properties, such as a greater half-life, than transcripts produced from the naturally occurring sequence.

The present invention also encompasses production of DNA sequences, or portions thereof, which encode the hSLAP-2v3 and hSLAP-2v4 polypeptides, and its derivatives, entirely by synthetic chemistry. After production, the synthetic sequence may be inserted into any of the many available expression vectors and cell systems using reagents that are well known and practiced by those in the art. Moreover, synthetic chemistry may be used to introduce mutations into a sequence encoding hSLAP-2v3 and hSLAP-2v4 polypeptides, or any fragment thereof.

Also encompassed by the present invention are polynucleotide sequences that are capable of hybridizing to the claimed nucleotide sequence of hSLAP-2v3 and hSLAP-2v4, such as that shown in SEQ ID NO:1 or SEQ ID NO:3, under various conditions of stringency. Hybridization conditions are typically based on the melting temperature (Tm) of the nucleic acid binding complex or probe (see, G. M. Wahl and S. L. Berger, 1987; *Methods Enzymol.*, 152:399-407 and A. R. Kimmel, 1987; *Methods Enzymol.*, 152:507-511), and may be used at a defined stringency. For example, included in the present invention are sequences capable of hybridizing under moderately stringent conditions to the hSLAP-2 nucleic acid sequence of SEQ ID NO:1, SEQ ID NO:3, and other sequences which are degenerate to those which encode the hSLAP-2v3 and hSLAP-2v4 polypeptides (e.g., as a non-limiting example: pre-washing solution of 2×SSC, 0.5% SDS, 1.0 mM EDTA, pH 8.0, and hybridization conditions of 50° C., 5×SSC, overnight).

In another embodiment of the present invention, polynucleotide sequences or fragments (peptides) thereof which encode the hSLAP-2v3 and hSLAP-2v4 polypeptides may be used in recombinant DNA molecules to direct the expression of the hSLAP-2v3 and hSLAP-2v4 polypeptides product, or fragments or functional equivalents thereof, in appropriate host cells. Because of the inherent degeneracy of the genetic code, other DNA sequences, which encode substantially the same or a functionally equivalent amino acid sequence, may be produced and these sequences may be used to express hSLAP-2 protein.

Representative examples of polynucleotide fragments of the invention, include, for example, fragments comprising, or alternatively consisting of, a sequence from about nucleotide number 1-50, 51-100, 101-150, 151-200, 201-250, 251-300, 301-350, 351-400, 401-450, 451-500, 501-550, 551-600, 651-700, 701-750, 751-800, 800-850, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-2000, or 2001, or to the end of SEQ ID NO:1 or SEQ ID NO:3, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Also encompassed by the present invention are polynucleotides which hybridize to these nucleic acid molecules under stringent hybridization conditions or lower stringency conditions, as are the polypeptides encoded by these polynucleotides.

Moreover, polynucleotide fragments can be about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, or about 700 contiguous nucleotides in length. In this context "about" includes the particularly recited ranges or values, and ranges or values larger or smaller by several (5, 4, 3, 2, or 1) nucleotides, at either extreme or at both extremes.

In the present invention, a "polypeptide fragment" refers to an amino acid sequence which is a portion of that contained in SEQ ID NO:2 or 4, or encoded by the cDNA contained in a deposited clone. Protein (polypeptide) fragments may be "free-standing" or comprised within a larger polypeptide of which the fragment forms a part or region, most preferably as a single continuous region. Representative examples of polypeptide fragments of the invention, include, for example, fragments comprising, or alternatively consisting of, from about amino acid number 1-20, 21-40, 41-60, 61-80, 81-100, 102-120, 121-140, 141-160, 161, 221, 241 or to the end of the coding region. Moreover, polypeptide fragments can be about 20, 30, 40, 50, 60, 70, 80, 90, 100, 110, 120, 130, 140, 150, 160, 170, 180, 190, 200, 210, 220, 230, or 240 contiguous amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

As will be appreciated by those having skill in the art, it may be advantageous to produce hSLAP-2v3 and hSLAP-2v4 polypeptides-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequence of the present invention can be engineered using methods generally known in the art in order to alter hSLAP-2v3 and hSLAP-2v4 polypeptides-encoding sequences for a variety of reasons, including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and the like.

In another embodiment of the present invention, natural, modified, or recombinant nucleic acid sequences, or a fragment thereof, encoding hSLAP-2v3 and hSLAP-2v4 polypeptides may be ligated to a heterologous sequence to encode a fusion protein. For example, for screening peptide libraries for inhibitors or modulators of hSLAP-2 activity or binding, it may be useful to encode a chimeric hSLAP-2 protein that can be recognized by a commercially available antibody. A fusion protein may also be engineered to contain a cleavage site located between the hSLAP-2 protein-encoding sequence and the heterologous protein sequence, so that the hSLAP-2 protein may be cleaved and purified away from the heterologous moiety.

In another embodiment, sequences encoding the hSLAP-2v3 and hSLAP-2v4 polypeptides may be synthesized in whole, or in part, using chemical methods well known in the art (see, for example, M. H. Caruthers et al., 1980, *Nucl. Acids Res. Symp. Ser.*, 215-223 and Horn, T. et al., 1980, *Nucl. Acids Res. Symp. Ser.*, 225-232). Alternatively, the protein itself may be produced using chemical methods to synthesize the amino acid sequence of the hSLAP-2v3 and hSLAP-2v4 polypeptides, or a fragment or portion thereof. For example, peptide synthesis can be performed using various solid-phase techniques (J. Y. Roberge et al., 1995, *Science,* 269:202-204) and automated synthesis may be achieved, for example, using the ABI 431 A Peptide Synthesizer (PE Biosystems).

The newly synthesized peptide can be substantially purified by preparative high performance liquid chromatography (e.g., T. Creighton, 1983, *Proteins, Structures and Molecular Principles*, WH Freeman and Co., New York, N.Y.), by reversed-phase high performance liquid chromatography, or other purification methods as are known in the art. The composition of the synthetic peptides may be confirmed by amino acid analysis or sequencing (e.g., the Edman degradation procedure; Creighton, supra). In addition, the amino acid sequence of the hSLAP-2v3 and hSLAP-2v4 polypeptides or any portion thereof, may be altered during direct synthesis and/or combined using chemical methods with sequences from other proteins, or any part thereof, to produce a variant polypeptide.

Expression of Human hSLAP-2 Protein

To express a biologically active/functional hSLAP-2v3 and hSLAP-2v4 polypeptides or peptide, the nucleotide sequences encoding the hSLAP-2v3 and hSLAP-2v4 polypeptides, or functional equivalents, may be inserted into an appropriate expression vector, i.e., a vector which contains the necessary elements for the transcription and translation of the inserted coding sequence. Methods which are well known to those skilled in the art may be used to construct expression vectors containing sequences encoding the hSLAP-2v3 and hSLAP-2v4 polypeptides and appropriate transcriptional and translational control elements. These methods include in vitro recombinant DNA techniques, synthetic techniques, and in vivo genetic recombination. Such techniques are described in J. Sambrook et al., 1989, *Molecular Cloning, A Laboratory Manual*, Cold Spring Harbor Press, Plainview, N.Y. and in F. M. Ausubel et al., 1989, *Current Protocols in Molecular Biology*, John Wiley & Sons, New York, N.Y.

A variety of expression vector/host systems may be utilized to contain and express sequences encoding the hSLAP-2v3 and hSLAP-2v4 polypeptides. Such expression vector/host systems include, but are not limited to, microorganisms such as bacteria transformed with recombinant bacteriophage, plasmid, or cosmid DNA expression vectors; yeast or fungi transformed with yeast or fungal expression vectors; insect cell systems infected with virus expression vectors (e.g., baculovirus); plant cell systems transformed with virus expression vectors (e.g., cauliflower mosaic virus (CaMV) and tobacco mosaic virus (TMV)), or with bacterial expression vectors (e.g., Ti or pBR322 plasmids); or animal cell systems. The host cell employed is not limiting to the present invention.

"Control elements" or "regulatory sequences" are those non-translated regions of the vector, e.g., enhancers, promoters, 5' and 3' untranslated regions, which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT® phagemid (Stratagene; La Jolla, Calif.) or PSPORT1 plasmid (Life Technologies), and the like, may be used. The baculovirus polyhedrin promoter may be used in insect cells. Promoters or enhancers derived from the genomes of plant cells (e.g., heat shock, RUBISCO; and storage protein genes), or from plant viruses (e.g., viral promoters or leader sequences), may be cloned into the vector. In mammalian cell systems, promoters from mammalian genes or from mammalian viruses are preferred. If it is necessary to generate a cell line that contains multiple copies of the sequence encoding hSLAP-2v3 or hSLAP-2v4, vectors based on SV40 or EBV may be used with an appropriate selectable marker.

In general, fusion proteins are soluble and can be easily purified from lysed cells. For GST-fusion proteins purification is performed by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used (for reviews, see F. M. Ausubel et al., supra, and Grant et al., 1987, *Methods Enzymol.,* 153:516-544).

Should plant expression vectors be desired and used, the expression of sequences encoding the hSLAP-2v3 and hSLAP-2v4 polypeptides may be driven by any of a number of promoters. For example, viral promoters such as the 35S and 19S promoters of CaMV may be used alone or in combination with the omega leader sequence from TMV (N.

Takamatsu, 1987, *EMBO J.*, 6:307-311). Alternatively, plant promoters such as the small subunit of RUBISCO, or heat shock promoters, may be used (G. Coruzzi et al., 1984, *EMBO J.*, 3:1671-1680; R. Broglie et al., 1984, *Science*, 224:838-843; and J. Winter et al., 1991, *Results Probl. Cell Differ.* 17:85-105). These constructs can be introduced into plant cells by direct DNA transformation or pathogen-mediated transfection. Such techniques are described in a number of generally available reviews (see, for example, S. Hobbs or L. E. Murry, In: McGraw Hill *Yearbook of Science and Technology* (1992) McGraw Hill, New York, N.Y.; pp. 191-196).

An insect system may also be used to express the hSLAP-2v3 and hSLAP-2v4 polypeptides. For example, in one such system, *Autographa californica* nuclear polyhedrosis virus (AcNPV) is used as a vector to express foreign genes in *Spodoptera frugiperda* cells or in *Trichoplusia larvae*. The sequences encoding the hSLAP-2v3 and hSLAP-2v4 polypeptides may be cloned into a non-essential region of the virus such as the polyhedrin gene and placed under control of the polyhedrin promoter. Successful insertion of the hSLAP-2v3 and hSLAP-2v4 polypeptides will render the polyhedrin gene inactive and produce recombinant virus lacking coat protein. The recombinant viruses may then be used to infect, for example, *S. frugiperda* cells or *Trichoplusia larvae* in which the hSLAP-2v3 and hSLAP-2v4 polypeptides product may be expressed (E. K. Engelhard et al., 1994, *Proc. Nat. Acad. Sci.*, 91:3224-3227).

In mammalian host cells, a number of viral-based expression systems may be utilized. In cases where an adenovirus is used as an expression vector, sequences encoding the hSLAP-2v3 and hSLAP-2v4 polypeptides may be ligated into an adenovirus transcription/translation complex containing the late promoter and tripartite leader sequence. Insertion in a non-essential E1 or E3 region of the viral genome may be used to obtain a viable virus which is capable of expressing the hSLAP-2v3 and hSLAP-2v4 polypeptides in infected host cells (J. Logan and T. Shenk, 1984, *Proc. Natl. Acad. Sci.*, 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding the hSLAP-2v3 and hSLAP-2v4 polypeptides. Such signals include the ATG initiation codon and adjacent sequences. In cases where sequences encoding the hSLAP-2v3 and hSLAP-2v4 polypeptides, its initiation codon, and upstream sequences are inserted into the appropriate expression vector, no additional transcriptional or translational control signals may be needed. However, in cases where only coding sequence, or a fragment thereof, is inserted, exogenous translational control signals, including the ATG initiation codon, should be provided. Alternatively, the start codon may be intentionally deleted from the clone sequence. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system that is used, such as those described in the literature (D. Scharf et al., 1994, *Results Probl. Cell Differ.*, 20:125-162).

Moreover, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells having specific cellular machinery and characteristic mechanisms for such post-translational activities (e.g., COS, CHO, HeLa, MDCK, HEK293, and W138) are available from the American Type Culture Collection (ATCC®), American Type Culture Collection (ATCC®), 10801 University Boulevard, Manassas, Va. 20110-2209, and may be chosen to ensure the correct modification and processing of the foreign protein.

For long-term, high-yield production of recombinant proteins, stable expression is preferred. For example, cell lines which stably express the hSLAP-2 protein may be transformed using expression vectors which may contain viral origins of replication and/or endogenous expression elements and a selectable marker gene on the same, or on a separate, vector. Following the introduction of the vector, cells may be allowed to grow for 1-2 days in an enriched cell culture medium before they are switched to selective medium. The purpose of the selectable marker is to confer resistance to selection, and its presence allows the growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the Herpes Simplex Virus thymidine kinase (HSV TK), (M. Wigler et al., 1977, *Cell*, 11:223-32) and adenine phosphoribosyltransferase (I. Lowy et al., 1980, *Cell*, 22:817-23) genes which can be employed in tk$^-$ or aprt$^-$ cells, respectively. Also, anti-metabolite, antibiotic or herbicide resistance can be used as the basis for selection; for example, dhfr, which confers resistance to methotrexate (M. Wigler et al., 1980, *Proc. Natl. Acad. Sci.*, 77:3567-70); npt, which confers resistance to the aminoglycosides neomycin and G-418 (F. Colbere-Garapin et al., 1981, *J. Mol. Biol.*, 150:1-14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (S. C. Hartman and R. C. Mulligan, 1988, *Proc. Natl. Acad. Sci.*, 85:8047-51). Recently, the use of visible markers has gained popularity with such markers as the anthocyanins, β-glucuronidase and its substrate GUS, and luciferase and its substrate luciferin, which are widely used not only to identify transformants, but also to quantify the amount of transient or stable protein expression that is attributable to a specific vector system (C. A. Rhodes et al., 1995, *Methods Mol. Biol.*, 55:121-131).

Although the presence or absence of marker gene expression suggests that the gene of interest is also present, the presence and expression of the desired gene of interest may need to be confirmed. For example, if the hSLAP-2v3 or hSLAP-2v4 nucleic acid sequence is inserted within a marker gene sequence, recombinant cells containing sequences encoding the hSLAP-2v3 or hSLAP-2v4 polypeptide can be identified by the absence of marker gene function. Alternatively, a marker gene can be placed in tandem with a sequence encoding the hSLAP-2v3 or hSLAP-2v4 polypeptides under the control of a single promoter. Expression of the marker gene in response to induction or selection usually indicates co-expression of the tandem gene.

Alternatively, host cells which contain the nucleic acid sequence encoding the hSLAP-2v3 or hSLAP-2v4 polypeptides and which express the hSLAP-2v3 or hSLAP-2v4 polypeptides product may be identified by a variety of procedures known to those having skill in the art. These procedures include, but are not limited to, DNA-DNA or DNA-RNA hybridizations and protein bioassay or immunoassay techniques, including membrane, solution, or chip based technologies, for the detection and/or quantification of nucleic acid or protein.

Preferably, the hSLAP-2v3 and hSLAP-2v4 polypeptides are substantially purified subsequent to expression. hSLAP-2v3 and hSLAP-2v4 proteins can be isolated or purified in a variety of ways known to and practiced by those having skill in the art, depending on what other components may be present in the sample. Standard purification methods include electrophoretic, molecular, immunological and chromatographic techniques, including, but not limited to, ion exchange, hydrophobic affinity and reverse phase HPLC chromatography, and chromatofocusing. For example, the hSLAP-2v3 and hSLAP-2v4 polypeptides can be purified using a standard antibody against hSLAP-2v3 or hSLAP-2v4 polypeptides. Ultrafiltration and diafiltration techniques, in conjunction with protein concentration, are also useful. For general guidance in suitable purification techniques, see R. Scopes, 1982, *Protein Purification*, Springer-Verlag, NY. As will be understood by the skilled practitioner, the degree of purification necessary will vary depending on the intended use of the hSLAP-2 protein; in some instances, no purification will be necessary.

In addition to recombinant production, fragments of the hSLAP-2v3 and hSLAP-2v4 polypeptides may be produced by direct peptide synthesis using solid-phase techniques (J. Merrifield, 1963, *J. Am. Chem. Soc.*, 85:2149-2154). Protein synthesis may be performed using manual techniques or by automation. Automated synthesis may be achieved, for example, using ABI 431A Peptide Synthesizer (PE Biosystems). Various fragments of the hSLAP-2v3 and hSLAP-2v4 polypeptides can be chemically synthesized separately and then combined using chemical methods to produce the full-length molecule.

Detection of Human hSLAP-2 Polynucleotide

The presence of polynucleotide sequences encoding the hSLAP-2v3 and hSLAP-2v4 polypeptides can be detected by DNA-DNA or DNA-RNA hybridization, or by amplification using probes or portions or fragments of polynucleotides encoding the hSLAP-2v3 and hSLAP-2v4 polypeptides. Nucleic acid amplification based assays involve the use of oligonucleotides or oligomers, based on the sequences encoding the hSLAP-2v3 and hSLAP-2v4 polypeptides, to detect transformants containing DNA or RNA encoding the hSLAP-2v3 and hSLAP-2v4 polypeptides.

A wide variety of labels and conjugation techniques are known and employed by those skilled in the art and may be used in various nucleic acid and amino acid assays. Means for producing labeled hybridization or PCR probes for detecting sequences related to polynucleotides encoding the hSLAP-2v3 and hSLAP-2v4 polypeptides include oligo-labeling, nick translation, end-labeling, or PCR amplification using a labeled nucleotide. Alternatively, the sequences encoding the hSLAP-2v3 and hSLAP-2v4 polypeptides, or any portions or fragments thereof, may be cloned into a vector for the production of an mRNA probe. Such vectors are known in the art, are commercially available, and may be used to synthesize RNA probes in vitro by addition of an appropriate RNA polymerase, such as T7, T3, or SP(6) and labeled nucleotides. These procedures may be conducted using a variety of commercially available kits (e.g., Amersham Pharmacia Biotech, Promega and U.S. Biochemical Corp.). Suitable reporter molecules or labels which may be used include radionuclides, enzymes, fluorescent, chemiluminescent, or chromogenic agents, as well as substrates, cofactors, inhibitors, magnetic particles, and the like.

In another of its aspects, this invention relates to a diagnostic kit for detecting hSLAP-2 polynucleotide or polypeptide as it relates to a disease or susceptibility to a disease, particularly autoimmune diseases which may be caused by hyperactivated B cells, as well as diseases which may be caused by hyperactivated T cells (e.g., rheumatoid arthritis; asthma; psoriasis; multiple sclerosis; rejection of organ or tissue transplants; chronic obstructive pulmonary disease; inflammatory bowel diseases, including Crohn's Disease and ulcerative colitis; acute respiratory distress syndrome; and systemic lupus erythematosus), or disorders associated with other types of hematopoietic cells, such as allergies involving mast cells, leukemias and lymphomas, or chronic obstructive pulmonary disorders (as supra). Such a kit comprises one or more of the following:

(a) a hSLAP-2v3 or hSLAP-2v4 polynucleotide, preferably the nucleotide sequence of SEQ ID NO:1, SEQ ID NO:3, or a fragment thereof; or (b) a nucleotide sequence complementary to that of (a); or (c) a hSLAP-2v3 or hSLAP-2v4 polypeptides, preferably the polypeptide of SEQ ID NO: 2, SEQ ID NO:4, or a fragment thereof; or (d) an antibody directed to hSLAP-2v3 or hSLAP-2v4 polypeptide, preferably to the polypeptide of SEQ ID NO: 2, SEQ ID NO:4, or an antibody bindable portion thereof. It will be appreciated that in any such kit, (a), (b), (c) or (d) may comprise a substantial component and that instructions for use can be included.

Human hSLAP-2v3 and hSLAP-2v4 Polypeptides

Production, Detection, Isolation

Host cells transformed with nucleotide sequences encoding the hSLAP-2v3 or hSLAP-2v4 polypeptide, or fragments thereof, may be cultured under conditions suitable for the expression and recovery of the protein from cell culture. The protein produced by a recombinant cell may be secreted or contained intracellularly depending on the sequence and/or the vector used. As will be understood by those having skill in the art, expression vectors containing polynucleotides which encode the hSLAP-2v3 or hSLAP-2v4 protein may be designed to contain signal sequences which direct secretion of the hSLAP-2 protein through a prokaryotic or eukaryotic cell membrane.

Other constructions may be used to join nucleic acid sequences encoding the hSLAP-2v3 or hSLAP-2v4 protein to nucleotide sequence encoding a polypeptide domain which will facilitate purification of soluble proteins. Such purification facilitating domains include, but are not limited to, metal chelating peptides such as histidine-tryptophan modules that allow purification on immobilized metals; protein A domains that allow purification on immobilized immunoglobulin; and the domain utilized in the FLAGS extension/affinity purification system (Immunex Corp.; Seattle, Wash.). The inclusion of cleavable linker sequences such as those specific for Factor XA or enterokinase (Invitrogen, San Diego, Calif.) between the purification domain and the hSLAP-2 protein may be used to facilitate purification.

One such expression vector provides for expression of a fusion protein containing hSLAP-2v3 or hSLAP-2v4-encoding sequence and a nucleic acid encoding 6 histidine residues preceding a thioredoxin or an enterokinase cleavage site. The histidine residues facilitate purification on IMAC (immobilized metal ion affinity chromatography) as described by J. Porath et al., 1992, *Prot. Exp. Purif.*, 3:263-281, while the enterokinase cleavage site provides a means for purifying from the fusion protein. For a discussion of suitable vectors for fusion protein production, see D. J. Kroll et al., 1993; *DNA Cell Biol.*, 12:441-453.

Human artificial chromosomes (HACs) may be used to deliver larger fragments of DNA than can be contained and expressed in a plasmid vector. HACs are linear microchromosomes which may contain DNA sequences of 10K to 10M in size, and contain all of the elements that are required for stable mitotic chromosome segregation and maintenance (see, J. J. Harrington et al., 1997, *Nature Genet.*, 15:345-355). HACs of 6 to 10M are constructed and delivered via conventional delivery methods (e.g., liposomes, polycationic amino polymers, or vesicles) for therapeutic purposes.

A variety of protocols for detecting and measuring the expression of the hSLAP-2v3 and hSLAP-2v4 polypeptides using either polyclonal or monoclonal antibodies specific for the protein are known and practiced in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive with two non-interfering epitopes on the hSLAP-2v3 and hSLAP-2v4 polypeptides is preferred, but a competitive binding assay may also be employed. These and other assays are described in the art as represented by the publication of R. Hampton et al., 1990; *Serological Methods, a Laboratory Manual*, APS Press, St Paul, Minn. and D. E. Maddox et al., 1983; *J. Exp. Med.*, 158:1211-1216).

Antibodies Raised Against Human SLAP-2 and Uses Thereof

Antagonists or inhibitors of the hSLAP-2v3 and hSLAP-2v4 polypeptides of the present invention may be produced using methods which are generally known in the art. In particular, purified hSLAP-2v3 or hSLAP-2v4 protein, or fragments thereof, can be used to produce antibodies, or to screen libraries of pharmaceutical agents or other compounds, particularly, small molecules, synthetic or naturally occurring, to identify those which specifically bind hSLAP-2v3 or hSLAP-2v4. (e.g. Libraries are commercially available from Sigma or Aldrich).

Antibodies specific for the hSLAP-2v3 and hSLAP-2v4 polypeptides, or immunogenic peptide fragments thereof, can be generated using methods that have long been known and conventionally practiced in the art. Such antibodies may include, but are not limited to, polyclonal, monoclonal, chimeric, single chain, Fab fragments, and fragments produced by an Fab expression library. Neutralizing antibodies, (i.e., those which inhibit dimer formation) are especially preferred for therapeutic use.

For the production of antibodies, various hosts including goats, rabbits, sheep, rats, mice, humans, and others, can be immunized by injection with hSLAP-2v3 and hSLAP-2v4 polypeptides, or any peptide fragment or oligopeptide thereof, which has immunogenic properties. Depending on the host species, various adjuvants may be used to increase the immunological response. Nonlimiting examples of suitable adjuvants include Freund's (incomplete), mineral gels such as aluminum hydroxide or silica, and surface-active substances such as lysolecithin, pluronic polyols, polyanions, peptides, oil emulsions, KLH, and dinitrophenol. Adjuvants typically used in humans include BCG (bacilli Calmette Guérin) and *Corynebacterium parvumn*.

Preferably, the peptides, fragments, or oligopeptides used to induce antibodies to hSLAP-2v3 and hSLAP-2v4 polypeptides (i.e., immunogens) have an amino acid sequence having at least five amino acids, and more preferably, at least 7-10 amino acids. It is also preferable that the immunogens are identical to a portion of the amino acid sequence of the natural protein; they may also contain the entire amino acid sequence of a small, naturally occurring molecule. The peptides, fragments or oligopeptides may comprise a single epitope or antigenic determinant or multiple epitopes. Short stretches of hSLAP-2 amino acids may be fused with those of another protein, such as KLH, and antibodies are produced against the chimeric molecule.

Monoclonal antibodies to hSLAP-2v3 and hSLAP-2v4 polypeptides, or immunogenic fragments thereof, may be prepared using any technique which provides for the production of antibody molecules by continuous cell lines in culture. These include, but are not limited to, the hybridoma technique, the human B-cell hybridoma technique, and the EBV-hybridoma technique (G. Kohler et al., 1975, *Nature*, 256:495-497; D. Kozbor et al., 1985, *J. Immunol. Methods*, 81:31-42; R. J. Cote et al., 1983, *Proc. Natl. Acad. Sci. USA*, 80:2026-2030; and S. P. Cole et al., 1984, *Mol. Cell Biol.*, 62:109-120). The production of monoclonal antibodies is well known and routinely used in the art.

According to the present invention, antibodies can be generated from various regions of the hSLAP-2v3 and hSLAP-2v4 polypeptides. Discrete domains of the hSLAP-2 protein (e.g., the proline-rich domain, or a portion thereof, the residues of which are depicted in FIGS. 3A-3B and the SH2 and/or SH3 domain, or a portion thereof, the residues of which are also depicted in FIGS. 3A-3B), may also be suitable for use as immunogens to produce antibodies to human hSLAP-2v3 or hSLAP-2v4.

In addition, techniques developed for the production of "chimeric antibodies," the splicing of mouse antibody genes to human antibody genes to obtain a molecule with appropriate antigen specificity and biological activity can be used (S. L. Morrison et al., 1984, *Proc. Natl. Acad. Sci. USA*, 81:6851-6855; M. S, Neuberger et al., 1984, *Nature*, 312:604-608; and S. Takeda et al., 1985, *Nature*, 314:452-454). Alternatively, techniques described for the production of single chain antibodies may be adapted, using methods known in the art, to produce hSLAP-2v3 and hSLAP-2v4 polypeptides-specific single chain antibodies. Antibodies with related specificity, but of distinct idiotypic composition, may be generated by chain shuffling from random combinatorial immunoglobulin libraries (D. R. Burton, 1991, *Proc. Natl. Acad. Sci. USA*, 88:11120-3). Antibodies may also be produced by inducing in vivo production in the lymphocyte population or by screening recombinant immunoglobulin libraries or panels of highly specific binding reagents as disclosed in the literature (R. Orlandi et al., 1989, *Proc. Natl. Acad. Sci. USA*, 86:3833-3837 and G. Winter et al., 1991, *Nature*, 349:293-299).

Antibody fragments which contain specific binding sites for the hSLAP-2v3 and hSLAP-2v4 polypeptides may also be generated. For example, such fragments include, but are not limited to, F(ab')$_2$ fragments which can be produced by pepsin digestion of the antibody molecule and Fab fragments which can be generated by reducing the disulfide bridges of the F(ab')$_2$ fragments. Alternatively, Fab expression libraries may be constructed to allow rapid and easy identification of monoclonal Fab fragments with the desired specificity (W. D. Huse et al., 1989, *Science*, 254:1275-1281).

Various immunoassays can be used for screening to identify antibodies having the desired specificity. Numerous protocols for competitive binding or immunoradiometric assays using either polyclonal or monoclonal antibodies with established specificities are well known in the art. Such immunoassays typically involve measuring the formation of complexes between the hSLAP-2v3 and hSLAP-2v4 polypeptides and its specific antibody. A two-site, monoclonal-based immunoassay utilizing monoclonal antibodies reactive with two non-interfering hSLAP-2v3 and hSLAP-2v4 polypeptides epitopes is preferred, but a competitive binding assay may also be employed (Maddox, supra).

Therapeutics/Treatments

In an embodiment of the present invention, the polynucleotide encoding the hSLAP-2v3 and hSLAP-2v4 polypeptides, or any fragment or complement thereof; may be used for therapeutic purposes. In one aspect, anti-sense to the polynucleotide encoding the hSLAP-2v3 and hSLAP-2v4 polypeptides may be used in situations in which it would be desirable to block translation of the mRNA. In particular, cells may be transformed with sequences complementary to polynucleotides encoding the hSLAP-2v3 and hSLAP-2v4 polypeptides. Thus, complementary molecules may be used to modulate human hSLAP-2 polynucleotide and polypeptide activity, or to achieve regulation of gene function. Such technology is now well known in the art, and sense or anti-sense oligomers or oligonucleotides, or larger fragments, can be designed from various locations along the coding or control regions of polynucleotide sequences encoding the hSLAP-2v3 and hSLAP-2v4 polypeptides.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express nucleic acid sequence that is complementary to the nucleic acid sequence encoding the hSLAP-2v3 and hSLAP-2v4 polypeptides. These techniques are described both in J. Sambrook et al., supra and in F. M. Ausubel et al., supra.

The gene encoding the hSLAP-2v3 or hSLAP-2v4 polypeptide can be turned off by transforming a cell or tissue with an expression vector that expresses high levels of a hSLAP-2v3 or hSLAP-2v4 polypeptide-encoding polynucleotide, or a fragment thereof. Such constructs may be used to introduce untranslatable sense or anti-sense sequences into a cell. Even in the absence of integration into the DNA, such vectors may continue to transcribe RNA molecules until they are disabled by endogenous nucleases. Transient expression may last for a month or more with a non-replicating vector, and even longer if appropriate replication elements are designed to be part of the vector system.

Modifications of gene expression can be obtained by designing anti-sense molecules or complementary nucleic acid sequences (DNA, RNA, or PNA), to the control, 5', or regulatory regions of the gene encoding the hSLAP-2v3 or hSLAP-2v4 polypeptide, (e.g., signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described (see, for example, J. E. Gee et al., 1994, In: B. E. Huber and B. I. Can, *Molecular and Immunologic Approaches*, Futura Publishing Co.; Mt. Kisco, N.Y.). The anti-sense molecule or complementary sequence may also be designed to block translation of mRNA by preventing the transcript from binding to ribosomes.

Ribozymes, i.e., enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Suitable examples include engineered hammerhead motif ribozyme molecules that can specifically and efficiently catalyze endonucleolytic cleavage of sequences encoding the hSLAP-2v3 or hSLAP-2v4 polypeptide.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes according to the invention may be prepared by any method known in the art for the synthesis of nucleic acid molecules. Such methods include techniques for chemically synthesizing oligonucleotides, for example, solid phase phosphoramidite chemical synthesis. Alternatively, RNA molecules may be generated by in vitro and in vivo transcription of DNA sequences encoding human hSLAP-2v3 or hSLAP-2v4. Such DNA sequences may be incorporated into a wide variety of vectors with suitable RNA polymerase promoters such as T7 or SP. Alternatively, the cDNA constructs that constitutively or inducibly synthesize complementary hSLAP-2v3 or hSLAP-2v4 RNA can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl, rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytosine, guanine, thymine, and uridine which are not as easily recognized by endogenous endonucleases.

Many methods for introducing vectors into cells or tissues are available and are equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

The SH2 domain of SLAP was shown to bind to phosphorylated tyrosine residues in ZAP-70, Syk, and LAT (Tang, J. et al. (1999) *Proc. Natl. Acad. Sci., USA*. 96: 9775-9780), and possibly other signaling proteins (Sosinowski, T. et al. (2000) *J. Exptl. Med.* 191: 463-474). Moreover, hSLAP-2 was also found to bind to ZAP-70 and such binding was determined to be essential for its negative regulation of T-cell signal transduction. (see Pandey et al (J. Biol. Chem., 277(21):19131-

19138 (2002), and Loreto et al (Mol. Cell. Biol., 22(12):4241-4255 (2002)). The SH3 domain of SLAP was determined to most likely bind proline rich (PR) motifs, which may help to transmit important intracellular signals in many cell types. Seven tyrosine residues in the coding sequence of hSLAP-2v3 or hSLAP-2v4 may be sites of phosphorylation by (a) tyrosine kinase(s). Such phosphorylated tyrosine residues may be important for binding to other SH2- or PTB domains involved in cell regulation.

The art teaches that any molecule that binds to ZAP-70 would be expected to affect T-cell receptor signaling and thus would be useful as a target for therapeutic intervention for disorders affecting T-cell antigen receptor signaling, such as T-cell tumors, lymphomas, leukemias, thymomas, and autoimmune disorders, among others on account of the fact that ZAP-70 links the activated T-cell receptor to downstream signaling events that ultimately leads to the transcription of genes such as IL-2, which is a hallmark of T-cell activation. (see Chen et al., Cell 71:649-662 (1992); Zhang et al., Cell 92:83-92 (1998); Chan et al., EMBO J. 14:2499-2508 (1995); Williams et al., J. Biol. Chem. 271:19641-19644 (1996); and Williams et al., Mol. Cell. Biol., 18:1388-1399 (1998).

In one alternative embodiment, the hSLAP-2v3 or hSLAP-2v4 polypeptide may not bind ZAP-70, or may bind ZAP-70 but not affect the ability of ZAP-70 to affect T-cell activation.

In another embodiment of the present invention, an expression vector containing the complement of the polynucleotide encoding the hSLAP-2v3 or hSLAP-2v4 polypeptides or an anti-sense oligonucleotide, may be administered to an individual to treat or prevent immune system related conditions, diseases, or disorders, T-cell and B-cell neoplasms; inflammation disorders, diseases and conditions, rheumatoid arthritis, osteoarthritis, psoriasis, rhinitis, inflammatory bowel disease (Crohn's and ulcerative colitis), allergies, particularly those involving hyperactivity of B-cells and T-cells, or other immune cells, such as mast cells or eosinophils; autoimmune diseases such as systemic lupus erythematosus and multiple sclerosis; pulmonary diseases including asthma, acute respiratory distress syndrome, and chronic obstructive pulmonary disorder; tissue/organ rejection; and cancer.

A variety of specialized oligonucleotide delivery techniques may be employed, for example, encapsulation in unilamellar liposomes and reconstituted Sendai virus envelopes for RNA and DNA delivery (Arad et al., 1986, *Biochem. Biophys. Acta.*, 859:88-94).

In another embodiment, the proteins, antagonists, antibodies, intracellular antibodies, agonists, complementary sequences, or vectors of the present invention can be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Any of the therapeutic methods described above may be applied to any individual in need of such therapy, including, for example, mammals such as dogs, cats, cows, horses, rabbits, monkeys, and most preferably, humans.

Screening Methods

The hSLAP-2v3 or hSLAP-2v4 protein and nucleic acid can be used in screening assays of candidate bioactive agents that modulate hSLAP-2v3 or hSLAP-2v4 bioactivity, for potential use to treat T- and B-cell disorders, such as tumors, lymphomas, and leukemias, or to treat inflammation disorders, such as those involving T-cells. In addition, hSLAP-2v3 or hSLAP-2v4 protein and encoding nucleic acid can be used as effectors in methods to affect T-cell activation. By "modulate" herein is meant that the bioactivity of hSLAP-2v3 or hSLAP-2v4 is altered, i.e., either increased or decreased. In a preferred embodiment, hSLAP-2v3 or hSLAP-2v4 bioactivity is inhibited. hSLAP-2v3 and hSLAP-2v4 are members of the class of adapter proteins involved in T-cell activation and T-cell responses; thus, it may play a role in antigen-presenting cells such as B-cells. Accordingly, hSLAP-2v3 or hSLAP-2v4 can be used as a target to screen for inhibitors of its function or expression.

Inhibitors of human hSLAP-2v3 or hSLAP-2v4 may be identified by screening compounds to ascertain their effect on hSLAP-2v3 or hSLAP-2v4 activity. As described herein, in some embodiments of the present invention, compounds are screened to identify inhibitors by contacting human hSLAP-2v3 or hSLAP-2v4 with a molecule with which it binds or associates, (e.g., possibly ZAP-70, Syk, and LAT as suggested by published data with the SLAP protein; Tang, J. et al. (1999) *Proc. Natl. Acad. Sci. USA* 96:9775-9780; as well as in Pandey et al and Loreto et al), in the presence or absence of a test compound. Under conditions of the assay, the inhibitors will prevent or reduce binding of human hSLAP-2v3 or hSLAP-2v4 to ZAP-70, for example. Antibodies which inhibit hSLAP-2v3 or hSLAP-2v4/ZAP-70 binding are useful as inhibitors and, therefore as positive controls in the assay.

In a similar fashion, activators of human hSLAP-2v3 or hSLAP-2v4 may be identified by screening compounds to ascertain their effect on hSLAP-2v3 or hSLAP-2v4/ZAP-70 binding, for example. In some embodiments of the present invention, compounds are screened to identify activators by contacting human hSLAP-2v3 or hSLAP-2v4 with ZAP-70 in the presence or absence of a test compound. Under conditions of the assay, the activators will enhance, accelerate or increase binding of human hSLAP-2v3 or hSLAP-2v4 to ZAP-70. Antibodies which inhibit hSLAP-2v3 or hSLAP-2v4/ZAP-70 binding are useful as negative controls in such assays.

In another embodiment, an assay is provided to identify compounds that inhibit the phosphorylation of hSLAP-2v3 or hSLAP-2v4 by tyrosine kinases such as, for example but not limited to, certain cellular receptors. In one aspect, hSLAP-2v3 or hSLAP-2v4 is bound to solid substrate and the reaction buffer contains $^{32}$P-gamma-ATP. Tyrosine kinase is added in the presence or absence of a test compound. Test compounds are identified that result in a decrease in the amount of $^{32}$P label that is incorporated into hSLAP-2v3 or hSLAP-2v4, compared with the level of phosphorylation observed in their absence. Kits are provided which comprise a container with hSLAP-2v3 or hSLAP-2v4 fixed to a solid phase, a container with the reaction buffer, optionally containing $^{32}$P-gamma-ATP, and a container with tyrosine kinase. Kits may optionally have positive and/or negative controls. Such kits typically also have instructions for performing such assays.

In another embodiment of the present invention, hSLAP-2v3 or hSLAP-2v4 proteins and nucleic acids are used in screening assays to identify and detect candidate bioactive agents that modulate hSLAP-2v3 or hSLAP-2v4 bioactivity, for potential use to treat autoimmune diseases which may be caused by hyperactivated B cells, as well as to treat diseases which may be caused by hyperactivated T cells, in addition to other immune system related conditions, diseases, or disorders, T-cell and B-cell neoplasms; inflammation disorders, diseases and conditions, rheumatoid arthritis, osteoarthritis, psoriasis, rhinitis, inflammatory bowel disease (Crohn's and ulcerative colitis), allergies, particularly those involving hyperactivity of B-cells and T-cells, or other immune cells, such as mast cells or eosinophils; autoimmune diseases such as systemic lupus erythematosus and multiple sclerosis; pulmonary diseases including asthma, acute respiratory distress syndrome, and chronic obstructive pulmonary disorder; tissue/organ rejection; and cancer.

In a related embodiment, the methods comprise screening for a bioactive agent capable of inhibiting the bioactivity of a hSLAP-2v3 or hSLAP-2v4 protein. By "bioactivity" herein is meant the binding of the hSLAP-2v3 or hSLAP-2v4 to any of its targets, for example, including ZAP-70, Syk, and LAT, as suggested by published data with SLAP protein, as well as published data for hSLAP-2 (see Pandey et al, and Loreto et al.). Thus, bioactive agents that prevent hSLAP-2v3 or hSLAP-2v4 binding, i.e., interrupt or block or inhibit the interaction of hSLAP-2v3 or hSLAP-2v4 and its target molecule, may be found. The method comprises combining the hSLAP-2v3 or hSLAP-2v4 protein and a candidate bioactive agent, and determining the binding of the candidate agent to hSLAP-2v3 or hSLAP-2v4 protein.

Generally, in performing such methods, a hSLAP-2v3 or hSLAP-2v4 polypeptides is non-diffusably bound to an insoluble support having isolated sample receiving areas (e.g. a microtiter plate, an array, etc.). The criteria for suitable insoluble supports are that they can be made of any composition to which polypeptides can be bound, they are readily separated from soluble material, and they are otherwise compatible with the overall method of screening. The surface of such supports may be solid or porous and of any convenient size or shape. Examples of suitable insoluble supports include microtiter plates, arrays, membranes and beads. These are typically made of glass, plastic (e.g., polystyrene), polysaccharides, nylon or nitrocellulose. Microtiter plates and arrays are especially convenient, because a large number of assays can be carried out simultaneously, using small amounts of reagents and samples. The particular manner of binding the polypeptide is not crucial, so long as it is compatible with the reagents and overall methods of the invention, maintains the activity of the peptide and is non-diffusable. Preferred methods of binding include the use of antibodies (which should not hinder the binding of hSLAP-2v3 or hSLAP-2v4 to its associated proteins), direct binding to "sticky" or ionic supports, chemical crosslinking, etc. Following binding of the polypeptide, excess unbound material is removed by washing. The sample receiving areas may then be blocked as needed through incubation with bovine serum albumin (BSA), casein or other innocuous/non-reactive protein.

A candidate bioactive agent is added to the assay. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like. The term "agent" as used herein describes any molecule, e.g., protein, oligopeptide, small organic molecule, polysaccharide, polynucleotide, etc., having the capability of directly or indirectly altering the bioactivity of hSLAP-2v3 or hSLAP-2v4 proteins. Generally a plurality of assay mixtures are run in parallel with different agent concentrations to obtain a differential response to the various concentrations. Typically, one of these concentrations serves as a negative control, i.e., at zero concentration, or below the level of detection.

Candidate agents encompass numerous chemical classes, though typically they are organic molecules, preferably small organic compounds having a molecular weight of more than 100 and less than about 10,000 daltons, preferably less than about 2000 to 5000 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. In addition, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

The determination of the binding of the candidate bioactive agent to the hSLAP-2v3 or hSLAP-2v4 polypeptide may be accomplished in a number of ways practiced in the art. In one aspect, the candidate bioactive agent is labeled, and binding is determined directly. Where the screening assay is a binding assay, one or more of the molecules may be joined to a label, where the label can directly or indirectly provide a detectable signal. Various labels include radioisotopes, fluorescent and chemiluminescent compounds, specific binding molecules, particles, e.g. magnetic particles, and the like. Specific binding molecules include pairs, such as biotin and streptavidin, digoxin and antidigoxin etc. For the specific-binding members, the complementary member would normally be labeled with a molecule which allows detection, in accordance with known procedures. In some embodiments, only one of the components is labeled. Alternatively, more than one component may be labeled with different labels; for example, the hSLAP-2v3 or hSLAP-2v4 polypeptide may be labeled with one fluorophor and the candidate agent labeled with another In one embodiment, the candidate bioactive agent is labeled. Labeled candidate bioactive agents are incubated with the hSLAP-2v3 or hSLAP-2v4 polypeptide for a time sufficient to allow binding, if present. Incubations may be performed at any temperature which facilitates optimal activity, typically between 4° C. and 40° C. Incubation periods are selected for optimum activity, but may also be optimized to facilitate rapid high throughput screening. Typically between 0.1 and 1 hour is sufficient. Excess reagent is generally removed or washed away. The presence or absence of the labeled component is detected to determine and indicate binding.

In a preferred embodiment, the screening method comprises combining a hSLAP-2v3 or hSLAP-2v4 protein, a candidate bioactive agent, and either ZAP-70 or another of the signaling proteins that associate with hSLAP-2v3 or hSLAP-2v4 (e.g., Syk, LAT), and determining the binding of hSLAP-2v3 or hSLAP-2v4 to either ZAP-70 or other signaling protein to determine the effect of the candidate bioactive agent on the hSLAP-2v3 or hSLAP-2v4-signaling protein interaction.

Another embodiment of this invention encompasses small molecule (e.g., drug) or compound screening and detection assays which involve the detection or identification of small molecules or compounds that can bind to a given protein, i.e., the hSLAP-2v3 or hSLAP-2v4 protein. Particularly preferred are assays suitable for high throughput screening methodologies. In such binding-based screening or detection assays, a functional assay is not typically required. All that is needed is a target protein, preferably substantially purified, and a library or panel of compounds (e.g., ligands, drugs, small molecules) to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, *Gen. Eng. News,* 20 (8)). The assay allows the detection of small molecules (e.g., drugs, ligands) that bind to expressed, and preferably purified, hSLAP-2v3 and hSLAP-2v4 polypeptides based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

In a differential screening method to identity bioactive agents that are capable of modulating the bioactivity of the hSLAP-2v3 or hSLAP-2v4 protein, hSLAP-2v3 or hSLAP-2v4 polypeptide is combined with either ZAP-70 or another signaling molecule which interacts with hSLAP-2v3 or hSLAP-2v4 in a first sample. A second sample comprises a candidate bioactive agent, hSLAP-2v3 or hSLAP-2v4 polypeptide and either ZAP-70 or other hSLAP-2v3 or hSLAP-2v4 interacting signaling molecule. The binding of hSLAP-2v3 or hSLAP-2v4 to either ZAP-70 or other signaling molecule is determined for both samples, and a change, or difference in binding, between the two samples indicates the presence of an agent capable of modulating the bioactivity of hSLAP-2v3 or hSLAP-2v4. Alternatively, a differential screening method is utilized to identify drug candidates that bind to the native hSLAP-2v3 or hSLAP-2v4, but cannot bind to modified hSLAP-2v3 or hSLAP-2v4 proteins, or variant hSLAP-2v3 or hSLAP-2v4 proteins, for example, those that have modifications which eliminate or decrease bioactivity of a hSLAP-2v3 or hSLAP-2v4 protein.

Preferably in such methods, all control and test samples are performed in at least triplicate to obtain statistically significant results. Incubation of all samples is for a time sufficient for the binding of the hSLAP-2v3 or hSLAP-2v4 proteins and the ZAP-70 and/or other signaling protein. Following incubation, all samples are washed free of non-specifically bound material and the amount of bound, labeled material determined. For example, where a radiolabel is employed as a label, the samples may be counted in a scintillation counter to determine the amount of labeled compound.

A variety of other reagents may be included in the screening assay. Such reagents include, but are not limited to, salts, neutral proteins, e.g. albumin, detergents, etc., which may be used to facilitate optimal protein-protein binding and/or reduce non-specific or background interactions. In addition, reagents that otherwise improve the efficiency of the assay, such as protease inhibitors, nuclease inhibitors, anti-microbial agents, etc. may be used. Further, the mixture of components in the method may be added in any order that provides for the requisite binding.

Kits are included as an embodiment of the present invention which comprise containers with reagents necessary to screen test compounds. Such kits include human hSLAP-2 and instructions for performing the assay. For example, kits may include means to detect and/or measure human hSLAP-2v3 or hSLAP-2v4 binding using antibodies that bind to human hSLAP-2v3 or hSLAP-2v4/ZAP-70 complex, but not to uncomplexed proteins, or antibodies that bind to uncomplexed proteins but not the human hSLAP-2v3 or hSLAP-2v4/ZAP-70 complex. Optionally antibodies raised against human hSLAP-2v3 or hSLAP-2v4 are provided as a control.

Pharmaceutical Compositions

A further embodiment of the present invention embraces the administration of a pharmaceutical composition, in conjunction with a pharmaceutically acceptable carrier, diluent, or excipient, for any of the above-described therapeutic uses and effects. Such pharmaceutical compositions may comprise hSLAP-2 nucleic acid, polypeptide, or peptides, antibodies to hSLAP-2v3 or hSLAP-2v4 polypeptide, or fragments thereof, mimetics, agonists (e.g., activators), antagonists (e.g., inhibitors) of the hSLAP-2v3 or hSLAP-2v4 polypeptide or polynucleotide. The compositions may be administered alone or in combination with at least one other agent, such as a stabilizing compound, which may be administered in any sterile, biocompatible pharmaceutical carrier, including, but not limited to, saline, buffered saline, dextrose, and water. The compositions may be administered to a patient alone, or in combination with other agents, drugs, hormones, or biological response modifiers.

The pharmaceutical compositions for use in the present invention can be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, vaginal, or rectal means.

In addition to the active ingredients (i.e., the hSLAP-2v3 or hSLAP-2v4 nucleic acid or polypeptide, or functional fragments thereof), the pharmaceutical compositions may contain suitable pharmaceutically acceptable carriers or excipients comprising auxiliaries which facilitate processing of the active compounds into preparations which can be used pharmaceutically. Further details on techniques for formulation and administration are provided in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained by the combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropyl-methylcellulose, or sodium carboxymethylcellulose; gums, including arabic and tragacanth, and proteins such as gelatin and collagen. If desired, disintegrating or solubilizing agents may be added, such as cross-linked polyvinyl pyrrolidone, agar, alginic acid, or a physiologically acceptable salt thereof, such as sodium alginate.

Dragee cores may be used in conjunction with physiologically suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification, or to characterize the quantity of active compound, i.e., dosage.

Pharmaceutical preparations, which can be used orally, include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. In addition, suspensions of the active compounds may be prepared as appropriate oily injection suspensions. Suitable lipophilic solvents or vehicles include fatty oils such as sesame oil, or synthetic fatty acid esters, such as ethyloleate or triglycerides, or liposomes. Optionally, the suspension may also contain suitable stabilizers or agents which increase the solubility of the compounds to allow for the preparation of highly concentrated solutions.

For topical or nasal administration, penetrants or permeation agents that are appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, and the like. Salts tend to be more soluble in aqueous solvents, or other protonic solvents, than are the corresponding free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, combined with a buffer prior to use. After the pharmaceutical compositions have been prepared, they can be placed in an appropriate container and labeled for treatment of an indicated condition. For administration of the hSLAP-2 product, such labeling would include amount, frequency, and method of administration.

Pharmaceutical compositions suitable for use in the present invention include compositions wherein the active ingredients are contained in an effective amount to achieve the intended purpose. The determination of an effective dose or amount is well within the capability of those skilled in the art. For any compound, the therapeutically effective dose can be estimated initially either in cell culture assays, e.g., using neoplastic cells, or in animal models, usually mice, rabbits, dogs, or pigs. The animal model may also be used to determine the appropriate concentration range and route of administration. Such information can then be used and extrapolated to determine useful doses and routes for administration in humans.

A therapeutically effective dose refers to that amount of active ingredient, for example, the hSLAP-2v3 or hSLAP-2v4 polypeptide, or active fragments thereof, antibodies to the hSLAP-2v3 or hSLAP-2v4 polypeptide, agonists or antagonists of the hSLAP-2v3 or hSLAP-2v4 polypeptide, which ameliorates, reduces, or eliminates the symptoms or condition. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio of toxic to therapeutic effects is the therapeutic index, which can be expressed as the ratio, $LD_{50}/ED_{50}$. Pharmaceutical compositions which exhibit large therapeutic indices are preferred. The data obtained from cell culture assays and animal studies are used in determining a range of dosages for human use. Preferred dosage contained in a pharmaceutical composition is within a range of circulating concentrations that include the ED50 with little or no toxicity. The dosage varies within this range depending upon the dosage form employed, sensitivity of the patient, and the route of administration.

The exact dosage will be determined by the practitioner, who will consider the factors related to the individual requiring treatment. Dosage and administration are adjusted to provide sufficient levels of the active moiety or to maintain the desired effect. Factors which may be taken into account include the severity of the individual's disease state, general health of the patient, age, weight, and gender of the patient, diet, time and frequency of administration, drug combination(s), reaction sensitivities, and tolerance/response to therapy. As a general guide, long-acting pharmaceutical compositions may be administered every 3 to 4 days, every week, or once every two weeks, depending on half-life and clearance rate of the particular formulation.

Normal dosage amounts may vary from 0.1 to 100,000 micrograms (μg), up to a total dose of about 1 gram (g), depending upon the route of administration. Guidance as to particular dosages and methods of delivery is provided in the literature and is generally available to practitioners in the art. Those skilled in the art will employ different formulations for nucleotides than for proteins or their inhibitors. Similarly, delivery of polynucleotides or polypeptides will be specific to particular cells, conditions, locations, and the like.

Assays and Diagnostics

In another embodiment of the present invention, antibodies which specifically bind to the hSLAP-2v3 or hSLAP-2v4 polypeptide may be used for the diagnosis of conditions or diseases characterized by expression (or overexpression) of the hSLAP-2 polynucleotide or polypeptide, or in assays to monitor patients being treated with hSLAP-2v3 or hSLAP-2v4 polypeptide, or its agonists, antagonists, or inhibitors. The antibodies useful for diagnostic purposes may be prepared in the same manner as those described above for use in therapeutic methods. Diagnostic assays for the hSLAP-2v3 or hSLAP-2v4 polypeptide include methods which utilize the antibody and a label to detect the protein in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

Several assay protocols including ELISA, RIA, and FACS for measuring the hSLAP-2v3 or hSLAP-2v4 polypeptide are known in the art and provide a basis for diagnosing altered or abnormal levels of hSLAP-2v3 or hSLAP-2v4 polypeptide expression. Normal or standard values for hSLAP-2v3 or hSLAP-2v4 polypeptide expression are established by combining body fluids or cell extracts taken from normal mammalian subjects, preferably human, with antibody to the hSLAP-2v3 or hSLAP-2v4 polypeptide under conditions suitable for complex formation. The amount of standard complex formation may be quantified by various methods; photometric means are preferred. Quantities of the hSLAP-2v3 or hSLAP-2v4 polypeptide expressed in subject sample, control sample, and disease samples from biopsied tissues are compared with the standard values. Deviation between standard and subject values establishes the parameters for diagnosing disease.

According to another embodiment of the present invention, the polynucleotides encoding hSLAP-2v3 or hSLAP-2v4 polypeptide may be used for diagnostic purposes. The polynucleotides which may be used include oligonucleotide sequences, complementary RNA and DNA molecules, and PNAs. The polynucleotides may be used to detect and quantify hSLAP-2-encoding nucleic acid expression in biopsied tissues in which expression (or under- or over-expression) of hSLAP-2 polynucleotide may be correlated with disease. The diagnostic assay may be used to distinguish between the absence, presence, and excess expression of hSLAP-2, and to monitor regulation of hSLAP-2 polynucleotide levels during therapeutic treatment or intervention.

In a related aspect, hybridization with PCR probes which are capable of detecting polynucleotide sequences, including genomic sequences, encoding hSLAP-2v3 or hSLAP-2v4 polypeptide, or closely related molecules, may be used to identify nucleic acid sequences which encode the hSLAP-2v3 or hSLAP-2v4 polypeptide. The specificity of the probe, whether it is made from a highly specific region, e.g., about 8 to 10 or 12 or 15 contiguous nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding the hSLAP-2v3 or hSLAP-2v4 polypeptide, alleles thereof, or related sequences.

In preferred embodiments, the present invention also encompasses methods of diagnosing one or more disorders referenced herein comprising a) determining the expression level of RNA encoding a polypeptide comprising the sequence of amino acids 2 to 241 of SEQ ID NO:2 or amino acids 2 to 221 of SEQ ID NO:4 in a normal tissue sample and in a test tissue sample by measuring RNA of said polypeptide; and b) comparing said expression level of said polypeptide from said test tissue sample with said expression level of said polypeptide from said normal test sample; wherein either an elevated or decreased expression level of said polypeptide in said test tissue sample relative to the expression level of said polypeptide in said normal tissue sample is indicative of the presence of said disease or disorder. Said measurement may be performed either by quantitiative PCR, including RT-PCR, protein quantitation using mass spectrometry, antibody detection, or any other nucleic acid or protein detection and measuring means.

The present invention also encompasses measuring RNA comprising hybridization between said RNA to an isolated nucleic acid consisting of a complete complement of at least 17 contiguous nucleotides of nucleotides of SEQ ID NO:1 or SEQ ID NO:3, wherein said hybridization is performed under conditions at least as stringent as hybridization in 2.2 mM MgCl2, 50 mM KCl, 10 mM Tris•HCL, pH 9, and 0.1% Triton X-100 at 42 C. Preferably, such measurement is performed under conditions in which the specific expression level of RNA encoding a polypeptide comprising the sequence of SEQ ID NO:2 or SEQ ID NO:4 is detected.

The present invention also encompasses measuring RNA comprising a second isolated nucleic acid consisting of at least 17 contiguous nucleotides of SEQ ID NO:1 or SEQ ID NO:3, wherein said isolated nucleic acid is directed to the antisense strand, and said second isolated nucleic acid is directed to the sense strand, wherein said hybridization is followed by at least one amplification step.

Probes may also be used for the detection of related sequences, and should preferably contain at least 50%, preferably greater than 80%, of the nucleotides encoding hSLAP-2v3 or hSLAP-2v4 polypeptide. The hybridization probes of this invention may be DNA or RNA and may be derived from the nucleotide sequence of SEQ ID NO:1, or from genomic sequence including promoter, enhancer elements, and introns of the naturally occurring hSLAP-2 protein.

Methods for producing specific hybridization probes for DNA encoding the hSLAP-2v3 or hSLAP-2v4 polypeptide include the cloning of nucleic acid sequence that encodes the hSLAP-2v3 or hSLAP-2v4 polypeptide, or hSLAP-2 derivatives, into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of detector/reporter groups, e.g., radionuclides such as $^{32}P$ or $^{35}S$, or enzymatic labels, such as alkaline phosphatase coupled to the probe via avidin/biotin coupling systems, and the like.

The polynucleotide sequence encoding the hSLAP-2v3 or hSLAP-2v4 polypeptide may be used in Southern or Northern analysis, dot blot, or other membrane-based technologies; in PCR technologies; or in dip stick, pin, ELISA or chip assays utilizing fluids or tissues from patient biopsies to detect the status of, e.g., levels or overexpression of hSLAP-2, or to detect altered hSLAP-2 expression. Such qualitative or quantitative methods are well known in the art.

In a particular aspect, the nucleotide sequence encoding the hSLAP-2v3 or hSLAP-2v4 polypeptide may be useful in assays that detect activation or induction of various B- and T-cell-related neoplasms or cancers, particularly those mentioned supra. The nucleotide sequence encoding the hSLAP-2v3 or hSLAP-2v4 polypeptide may be labeled by standard methods, and added to a fluid or tissue sample from a patient under conditions suitable for the formation of hybridization complexes. After a suitable incubation period, the sample is washed and the signal is quantified and compared with a standard value. If the amount of signal in the biopsied or extracted sample is significantly altered from that of a comparable control sample, the nucleotide sequence has hybridized with nucleotide sequence present in the sample, and the presence of altered levels of nucleotide sequence encoding the hSLAP-2v3 or hSLAP-2v4 polypeptide in the sample indicates the presence of the associated disease. Such assays may also be used to evaluate the efficacy of a particular therapeutic treatment regimen in animal studies, in clinical trials, or in monitoring the treatment of an individual patient.

To provide a basis for the diagnosis of disease associated with expression of hSLAP-2v3 or hSLAP-2v4, a normal or standard profile for expression is established. This may be accomplished by combining body fluids or cell extracts taken from normal subjects, either animal or human, with a sequence, or a fragment thereof, which encodes the hSLAP-2v3 or hSLAP-2v4 polypeptide, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject (patient) values is used to establish the presence of disease.

Once disease is established and a treatment protocol is initiated, hybridization assays may be repeated on a regular basis to evaluate whether the level of expression in the patient begins to approximate that which is observed in a normal individual. The results obtained from successive assays may be used to show the efficacy of treatment over a period ranging from several days to months.

With respect to cancer, the presence of an abnormal amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier, thereby preventing the development or further progression of the cancer.

Additional diagnostic uses for oligonucleotides designed from the nucleic acid sequence encoding the hSLAP-2v3 or hSLAP-2v4 polypeptide may involve the use of PCR. Such oligomers may be chemically synthesized, generated enzymatically, or produced from a recombinant source. Oligomers will preferably comprise two nucleotide sequences, one with sense orientation (5'→3') and another with anti-sense (3'→5'), employed under optimized conditions for identification of a specific gene or condition. The same two oligomers, nested sets of oligomers, or even a degenerate pool of oligomers may be employed under less stringent conditions for detection and/or quantification of closely related DNA or RNA sequences.

Methods suitable for quantifying the expression of hSLAP-2v3 or hSLAP-2v4 include radiolabeling or biotinylating nucleotides, co-amplification of a control nucleic acid, and standard curves onto which the experimental results are interpolated (P. C. Melby et al., 1993, *J. Immunol. Methods,* 159:235-244; and C. Duplaa et al., 1993, *Anal. Biochem.,* 229-236). The speed of quantifying multiple samples may be accelerated by running the assay in an ELISA format where the oligomer of interest is presented in various dilutions and a spectrophotometric or colorimetric response gives rapid quantification.

In another embodiment of the present invention, oligonucleotides, or longer fragments derived from the hSLAP-2v3 or hSLAP-2v4 polynucleotide sequence described herein may be used as targets in a microarray. The microarray can be used to monitor the expression level of large numbers of genes simultaneously (to produce a transcript image), and to identify genetic variants, mutations and polymorphisms. This information may be used to determine gene function, to understand the genetic basis of a disease, to diagnose disease, and to develop and monitor the activities of therapeutic agents. In a particular aspect, the microarray is prepared and used according to the methods described in WO 95/11995 (Chee et al.); D. J. Lockhart et al., 1996, *Nature Biotechnology,* 14:1675-1680; and M. Schena et al., 1996, *Proc. Natl. Acad. Sci. USA,* 93:10614-10619). Microarrays are further described in U.S. Pat. No. 6,015,702 to P. Lal et al.

In another embodiment of this invention, the nucleic acid sequence which encodes the hSLAP-2v3 or hSLAP-2v4 polypeptide may also be used to generate hybridization probes which are useful for mapping the naturally occurring genomic sequence. The sequences may be mapped to a particular chromosome, to a specific region of a chromosome, or to artificial chromosome constructions (HACs), yeast artificial chromosomes (YACs), bacterial artificial chromosomes (BACs), bacterial PI constructions, or single chromosome cDNA libraries, as reviewed by C. M. Price, 1993, *Blood Rev.,* 7:127-134 and by B. J. Trask, 1991, *Trends Genet.,* 7:149-154.

In another embodiment of the present invention, the hSLAP-2v3 or hSLAP-2v4 polypeptide, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between the hSLAP-2v3 or hSLAP-2v4 polypeptide, or portion thereof, and the agent being tested, may be measured utilizing techniques commonly practiced in the art and as described above.

Another technique for drug screening which may be used provides for high throughput screening of compounds having suitable binding affinity to the protein of interest, for example, as described in WO 84/03564. In this method, as applied to the hSLAP-2v3 or hSLAP-2v4 protein, large numbers of different small test compounds are synthesized on a solid substrate, such as plastic pins or some other surface. The test compounds are reacted with the hSLAP-2v3 or hSLAP-2v4 polypeptide, or fragments thereof, and washed. Bound hSLAP-2v3 or hSLAP-2v4 polypeptide is then detected by methods well known in the art. Purified hSLAP-2v3 or hSLAP-2v4 polypeptide can also be coated directly onto plates for use in the aforementioned drug screening techniques. Alternatively, non-neutralizing antibodies can be used to capture the peptide and immobilize it on a solid support.

In a further embodiment of this invention, competitive drug screening assays can be used in which neutralizing antibodies capable of binding hSLAP-2v3 or hSLAP-2v4 polypeptide specifically compete with a test compound for binding to hSLAP-2v3 or hSLAP-2v4 polypeptide. In this manner, the antibodies can be used to detect the presence of any peptide which shares one or more antigenic determinants with the hSLAP-2v3 or hSLAP-2v4 polypeptide.

Transgenics and Knock Outs

The present invention further encompasses transgenic non-human mammals, preferably mice, that comprise a recombinant expression vector harboring a nucleic acid sequence that encodes human hSLAP-2v3 or hSLAP-2v4 comprising the amino acid sequence of SEQ ID NO:2 or SEQ ID NO:4.

Transgenic non-human mammals useful to produce recombinant proteins are well known to the skilled practitioner, as are the expression vectors necessary and the techniques for generating transgenic animals. Generally, the transgenic animal comprises a recombinant expression vector in which the nucleotide sequence that encodes human hSLAP-2v3 or hSLAP-2v4 is operably linked to a tissue specific promoter whereby the coding sequence is only expressed in that specific tissue. For example, the tissue specific promoter can be a mammary cell specific promoter and the recombinant protein so expressed is recovered from the animal's milk.

The transgenic animals, particularly transgenic mice, containing a nucleic acid molecule which encodes human hSLAP-2v3 or hSLAP-2v4 may be used as animal models for studying in vivo the overexpression of hSLAP-2v3 or hSLAP-2v4 and for use in drug evaluation and discovery efforts to find compounds effective to inhibit or modulate the activity of hSLAP-2v3 or hSLAP-2v4, such as, for example, compounds for treating immune system related conditions, diseases, or disorders, T-cell and B-cell neoplasms; inflammation disorders, diseases and conditions, rheumatoid arthritis, osteoarthritis, psoriasis, rhinitis, inflammatory bowel disease (Crohn's and ulcerative colitis), allergies, particularly those involving hyperactivity of B-cells and T-cells, or other immune cells, such as mast cells or eosinophils; autoimmune diseases such as systemic lupus erythematosus and multiple sclerosis; pulmonary diseases including asthma, acute respiratory distress syndrome, and chronic obstructive pulmonary disorder; tissue/organ rejection; and cancer. One having ordinary skill in the art using standard techniques, such as those taught in U.S. Pat. No. 4,873,191, issued Oct. 10, 1989 to Wagner et al. and in U.S. Pat. No. 4,736,866, issued Apr. 12, 1988 to Leder et al., can produce transgenic animals which produce the human hSLAP-2, or splice variants thereof, and use the animals in drug evaluation and discovery projects.

Another aspect of the present invention relates to knockout mice and methods of using the same. In particular, transgenic mice may be generated which are homozygous for a mutated, non-functional hSLAP-2v3 or hSLAP-2v4 gene which is introduced into the animals using well-known techniques. The knockout mice produce no functional hSLAP-2 and thus are useful to study the function of hSLAP-2v3 or hSLAP-2v4. Furthermore, the mice may be used in assays to study the effect of test compounds in hSLAP-2v3 or hSLAP-2v4 deficient animals. For instance, hSLAP-2v3 or hSLAP-2v4-deficient mice can be used to determine if, how and to what extent hSLAP-2v3 or hSLAP-2v4 inhibitors will effect the animal and thus address concerns associated with inhibiting the activity of the molecule.

Methods of generating genetically deficient "knockout" mice are well known and are disclosed in M. R. Capecchi, 1989, *Science*, 244:1288-1292 and P. Li et al., 1995, *Cell*, 80:401-411. The human hSLAP-2v3 or hSLAP-2v4 cDNA clone can be used to isolate a murine hSLAP-2v3 or hSLAP-2v4 genomic clone. The genomic clone can be used to prepare a hSLAP-2v3 or hSLAP-2v4 targeting construct which can disrupt the hSLAP-2v3 or hSLAP-2v4 gene in the mouse by homologous recombination. The targeting construct contains a non-functioning portion of the hSLAP-2v3 or hSLAP-2v4 gene which inserts in place of the functioning portion of the native mouse gene. The non-functioning insert generally contains an insertion in the exon that encodes the active region of hSLAP-2v3 or hSLAP-2v4. The targeting construct can contain markers for both positive and negative selection. The positive selection marker allows for the selective elimination of cells which do not carry the marker, while the negative selection marker allows for the elimination of cells that carry the marker.

For example, a first selectable marker is a positive marker that will allow for the survival of cells carrying it. In some instances, the first selectable marker is an antibiotic resistance gene, such as the neomycin resistance gene, which can be placed within the coding sequence of the hSLAP-2v3 or hSLAP-2v4 gene to render it non-functional, while at the same time rendering the construct selectable. The antibiotic resistance gene is within the homologous region which can recombine with native sequences. Thus, upon homologous recombination, the non-functional and antibiotic resistance selectable gene sequences will be taken up. Knockout mice may be used as models, in particular, the Cre-Lox model, for studying B- and T-cell related disorder and hyperactivity and screening compounds for treating these disorders.

The targeting construct also contains a second selectable marker which is a negative selectable marker. Cells with the negative selectable marker will be eliminated. The second selectable marker is outside the recombination region. Thus, if the entire construct is present in the cell, both markers will be present. If the construct has recombined with native sequences, the first selectable marker will be incorporated into the genome and the second will be lost. The herpes simplex virus thymidine kinase (HSV tk) gene is an example of a negative selectable marker which can be used as a second marker to eliminate cells that carry it. Cells with the HSV tk gene are selectively killed in the presence of gangcyclovir.

Cells are transfected with targeting constructs and then selected for the presence of the first selection marker and the absence of the second. Constructs/DNA are then injected into the blastocyst stage and implanted into pseudopregnant females. Chimeric offspring which are capable of transferring the recombinant genes in their germline are selected, mated and their offspring examined for heterozygous carriers of the recombined genes. Mating of the heterozygous offspring can then be used to generate fully homozygous offspring which constitute hSLAP-2v3 or hSLAP-2v4-deficient knockout mice.

EXAMPLES

The Examples below are provided to illustrate the subject invention and are not intended to limit the invention.

Example 1

Method of Identifying the Novel hSLAP-2 Human Variants of the Present Invention

Polynucleotide sequences encoding the novel hSLAP-2 variants of the present invention were identified by a combination of structural threading and genomic mining methodologies.

Typical genome mining methods capitalize on sequence similarity as the basis for assigning gene function. However, the primary structure of a distantly related unknown gene (<30 percent identity at the level of the amino acid sequence) cannot always yield predicatable information leading to the structure of that gene, and is not always a good predictor of function. However, if there is a correlation between amino acid sequence and protein structure the characterization of function becomes easier.

It has been shown that clear sequence similarity implies structural similarity (sequence identity >50%). In addition it has also been shown that structural similarity exists for proteins even when the sequence similarity lies in the "twilight zone" (<30% sequence identity). There are several methods for detection of similar 3D folds between two polypeptides that have been developed. These methods are used to identify protein structural similarity, also know as similarity of 3D fold. The application of these methods is described collectively as Fold Recognition.

Fold recognition was originally envisioned as a tool to be used for validation of experimentally determined structures or hypothetical models. Prior to 1990, the three-dimensional protein databases contained several 3D structures which were not recognized as incorrect until a subsequent 3D structure was determined for the same molecule. Several fold recognition methods were developed and automated in the early 1990s including 3D profiles developed by the Eisenberg laboratory (Luthy et al., 1992, Fischer & Eisenberg, 1996) and protein threading as implemented by the Sippl group (Sippl, 1990; Sippl & Weitckus, 1992; Sippl, 1993), Thornton and Jones (Jones et al., 1992), Skolnick & Godzik (Godzik, 1992) laboratories.

These fold recognition tools were immediately used for validation of experimentally determined structures in the public Protein Data Bank (PDB, Bernstein et al. 1977). It was also recognized that these profile and threading methods could be used to evaluate the quality of molecular models constructed by comparative and homology modeling (Sali et al., Proteins 23:318-26 (1995)). The principle of fold recognition is that a library of known protein structures (derived from the Protein Data Bank, Bernstein et al. 1977) can be used to find the best 3D template that matches a given query sequence. Fold recognition methods such as protein threading fit a query sequence directly onto the cartesian coordinates of template structures. The plausibility of the molecular model created by the threading of a sequence onto a template three dimensional structure is evaluated by a scoring function constructed from a (statistical) knowledge database of known protein structure. To exploit structural information inherent in the molecular model, functional sites can be evaluated so that the structural models can be used to assign biochemical function. The Rose laboratory (Xu et al. 1999) made two such successful predictions on proteins from the *Methanococcus* genome that were classified as "hypothetical". The functional predictions were subsequently confirmed experimentally.

Fold recognition methods have been applied to microbial genome annotation (Fischer & Eisenberg, Proc. Natl. Acad. Sci., USA 94:11929, 1997; Huynen et al. 1998; Jones et al. 1998; Rychlewski et al. 1998; Rychlewski et al. 1999; Pawlowski et al. 1999). For each of the annotation methods cited above, screening of the fold predictions showed that fold predictions could be used to extend functional annotations in a genome. The functional conservation of a gene is based upon conservation of specific residues in active or other functional sites. Results varied depending upon the protein structure library used and the genome annotated. For purposes of genome annotation, novel folds cannot be recognized by fold recognition methods. Current estimates suggest that between 60 and 80 percent of fold domains are known. Experimental methods such as X-ray or NMR spectroscopy can be used to elucidate the three dimensional structures for these novel folds and this information is constantly being added to the public structure database, PDB. Addition of this information will increase the ability of fold recognition methods to detect three dimensional fold similarities.

Correlation of protein sequence with protein structure next brings the "paradox" of structural genomics. To what extent can the function of a protein be deduced from structure? The correlation of protein structure and function was explored by the Sippl group (Koppensteiner et al. 2000) who showed that proteins that have similar folds usually have similar functions. The study concluded that, even when sequence similarity was low (e.g., less than 30% identity), in 66% of the cases structural similarity corresponded to similarity in function. Published studies on genome annotation that utilize fold recognition technology suggest that, if sequence based methods can annotate 20-40% of a genome with high confidence, an additional 5-20% of the genome can be reliably annotated using fold recognition methods. In summary, it is clear that fold recognition methods can be used to complement the sequenced-based bioinformatics methods (mentioned above) to uncover additional functional relationships for genomic sequences.

Methodology

The goal of this method was to use the structural information from a family of protein domains to provide enhanced recognition and functional assignment for novel (hypothetical) and incorrectly annotated genome sequences Developed protocol is similar to the sequence-based profile methods such as PSI-BLAST (Altschul et al. 1997). It has been shown that the sequence based profile methods can incorporate position specific variation within a given protein family to extend the ability to detect remote sequence and functional conservation. In order to augment mutation information available for specific protein families, a protein threading protocol has been developed that enhances the sequence information by incorporating three dimensional residue interaction preferences for a related family of protein structures. The result provides a structural signature that, when applied across a protein family, allows for the recognition of structural similarity even in the absence of homology.

The protocol is best described as a structural genomics approach to genome mining. Briefly, there are four stages to this protocol for genome mining:

Protocol Genome Sequences

1. Template Library Generation

2. Genome Wide Fold RecognitionList 1

3. Novelty ScanList 1→List 2→List 3

4. in silico PredictionList 3→List 4

1. Template Library Generation

The first stage is the generation of the template library that will be used for fold recognition. This is the most critical stage since protein threading is dependent upon the library of known structures used for template matching. The goal of this stage was to gather the three dimensional structures for a specific protein family or superfamily. Methods which can be used to generate template libraries include but are not limited to:

A) Selection based upon previous structural classification databases available SCOP, CATH, DALI.

B) Selection based upon characterization of single domains that correspond to catalytic or functional domains of interest within the protein family of interest.

C) Selection which incorporates proprietary (in-house) Bristol-Myers Squibb three dimensional structures.

D) Selection of templates from the Protein Data Bank (Bernstein et al. 1977) using numerous sequence and profile based methods (some of which are available on the PDB web site www.rcsb.org/pdb.

E) Selection of templates can also be made using three dimensional structural comparison tools (Zu-Kang & Sippl 1996, Lackner et al. 2000) to collect and compare related three dimensional structures.

The preferred protocol for stage 1, Template Library Generation utilizes a combination of the above mentioned methods which would result in a comprehensive assembly of related protein domains of known structure and related functions.

2. Genome Wide Fold Recognition

Stage two consists of threading the entire genome (genome can be defined as a large number of sequences from an organism) onto each structure in the template library. For protein threading, the PROCERYON suite of software (Proceryon Biosciences, New York) was used with the protocol that was automated by programming (perl) scripts. The PROCERYON threading software fits a query sequence directly onto the cartesian coordinates of template structures. The plausibility of the fitted model was evaluated by a scoring function constructed from statistical knowledge based potentials that were derived from proteins of known three-dimensional structure. The threading scores of interest are the pairwise, surface, combined (pairwise interaction score and the surface score, P/S) energy scores and the sequence identity score (SEQ and ID). The scores for each genome sequence threaded onto each template was stored in a database and an additional score (Threshold Index) calculated. Threshold index is a single score that is a combination of the combined energy score and the sequence (identity score). In order to extract an initial list of genes (List 1) for post threading processing the threshold index score was used in combination with sequence identity and raw sequence length (number of amino acids). A list of genes (List 1) that met the following criteria were selected from this stage two process:

Threading index>50

Sequence identity>15%

Sequence length>100 amino acids and <700 amino acids

3. Novelty Scan

The list of gene sequences (List 1) resulting from the previous stage were processed in stage three using two successive tactics. The first tactic was to "back-thread" the genomic list (List 1) against a template library that contains at least one representative of each protein and functional domain. For this study we used the PDB40 for the template library. The PDB40 is a template library generated from all known protein structures that have less than 40% identity to each other. This tactic was aimed at testing the initial structural assignment used to identify the sequence(s) from the previous two stages. The goal was to determine what structural similarity exists between the query sequence and members of the protein and functional domain templates. The results of the back-threading were compared to the original structural assignment. Sequences were removed from the list (List 1) if more significant structural and functional relationships were found to templates from the protein and functional domain library (PDB40). The sequences remaining on the list (List 2) were passed onto the second tactic.

The second tactic was to perform successive exhaustive BLAST searches on the list (List 2) against a series of sequence databases which may include but are not limited to the following databases: non-redundant protein sequences, non-redundant nucleotide sequences, ESTs, Incyte Templates (LifeSeq Gold, Incyte Pharmaceuticals, Inc.) and databases of patented genes and protein sequences (Genseq Database, Derwent, Inc). The result of this stage (Stage 3) was the generation of a list (List 3) of gene sequences for which a putative biological function was determined and the novelty of the sequence assignment assessed by back-threading and exhaustive BLAST searches.

4. in silico Prediction

Each sequence in the list (List 3) was analyzed manually for possible functional conservation to members of the protein family template library and related sequences (Stage 1). Preferred procedures for this validation include but are not limited to:

A) Pairwise sequence alignment and conservation of functional site residues.

B) Multiple sequence alignment of members of the protein family template library and/or related protein sequences.

C) Multiple sequence alignments with proteins of known function whose relationships were determined based upon profile search methods such as PSI-BLAST and Hidden Markov Models (eg. Pfam, etc.).

D) Three dimensional homology or comparative modeling where a three dimensional model is used to help validate function.

E) Conservation profiles, sequence or structural motifs used to characterize the functional residues in catalytic, binding, allosteric and other functional sites.

F) Manual adjustment of the sequence alignment where the sequence(s) are aligned "by hand" for comparison to multiple sequence alignments derived from any or all of the steps A-E above.

The results of Stage 4 was a list (List 4) of sequences for which there was structural and or functional characterization based upon the in silico protocol.

The partial hSLAP-2v3 (also referred to as BMY_HPP34) polynucleotide (SEQ ID NO:5) and polypeptide (SEQ ID NO:6) sequence of the present invention was first identified as belonging to the phosphatase family using the above structural threading methods based upon its structural alignment to the human Shp-2 sequence and the human CDC25B sequence. The partial hSLAP-2v3 sequence was used to BLAST against the human genome database. This resulted in the identification of human BAC AC06831 as the portion of the genome harboring this gene. The GENEWISEDB algorithm was then applied to the BAC AL050318 sequence to elucidate the exon/intron structural of the hSLAP-2v3 gene.

Appropriate primers were designed based upon the genomic structure of the hSLAP-2v3 gene and the full-length clone was isolated as described herein.

Example 2

Method of Constructing a Size Fractionated Brain and Testis cDNA Library

Poly $A^+$ RNA from Clontech was treated with DNase I to remove genomic DNA contamination. The RNA was converted into double stranded cDNA using the SUPERSCRIPT® Plasmid System for cDNA Synthesis and Plasmid Cloning (Life Technologies). The cDNA was size fractionated on a TRANSGENOMIC® HPLC size exclusion column (TosoHass) with dimensions of 7.8 mm×30 cm and a particle size of 10 μm. Tris buffered saline was used as the mobile phase, and the column was run at a flow rate of 0.5 ml/min. The system was calibrated using a 1 kb ladder to determine which fractions should be pooled to obtain the largest cDNA library. Generally, fractions that eluted in the range of 12 to 15 minutes were used. The cDNA was precipitated, concentrated and then ligated into the Sal I/Not I sites in pSPORT. Following electroporation of the cDNA into DH12S, DNA from the resulting colonies were prepared and subjected to Sal I/Not I restriction enzyme digestion. Generally, the average insert size of libraries made by this procedure was greater than 3.5 Kb and the overall complexity of the library was greater than 10⁷ independent clones. The library was amplified in semi-solid agar for 2 days at 30 C. An aliquot (200 microliters) of the amplified library was inoculated into a 200 ml culture for single-stranded DNA isolation by super-infection with a fi helper phage. The single-stranded circular DNA was concentrated by ethanol precipitation, resuspended at a concentration of one microgram per microliter and used for the cDNA capture experiments.

Example 3

Method of Converting Double Stranded cDNA Libraries into Single Strand Circular Forms

Preparation of Culture

LB medium (200 mL+400 ul carb) was inoculated with 0.2 to 1 ml of thawed cDNA library. The culture was incubated, shaking at 250 rpm at 37° C. for 45 min. The optical density of the culture was measured. The OD600 was preferably between 0.025 and 0.040. One mL M13K07 helper phage was added to the culture and grown for 2 hours. At that time, 500 uL Kanamycin (30 mg/mL) was added and incubation continued for 15-18 hours.

Preparation of Cells for Precipitation

Cultures were poured into six 50 mL tubes. Cells were centrifuged at 10000 rpm in an HB-6 rotor for 15 minutes at 4° C. The supernatant was retrieved and cells discarded. The supernatant was filtered through a 0.2 um filter. DNase I (12000 units from Gibco) was added and incubated at room temperature for 90 minutes.

PEG Precipitation of DNA

Fifty mL of ice-cold 40% PEG 8000, 2.5 M NaCl, 10 mM $MgSO_4$ was added to the cell pellets. The solution was mixed and distributed into 6 centrifuge tubes and covered with parafilm. The tubes were incubated on wet ice for 1 hour (or at 4° C. overnight).

Phage were pelleted at 10000 rpm in an HB-6 rotor for 20 minutes at 4° C. The supernatant was discarded and the sides of the tubes wiped dry. The pellets were resuspended in 1 mL TE, pH 8.

The resuspended pellets were placed in a 14 mL SARSTEDT® tube (6 mL total). SDS was added to 0.1% (60 uL of stock 10% SDS). Proteinase K (60 uL of 20 mg/mL) was then added and incubated at 42 C for 1 hour.

DNA was extracted with phenol/chloroform by first adding 1 mL of 5M NaCl followed by an equal volume of phenol/chloroform (6 mL). The mixture was vortexed and centrifuged at 5K in an HB-6 rotor for 5 minutes at 4° C. The aqueous (top) phase was transferred to a new SARSTEDT® tube. Extractions were repeated until no interface was visible.

The DNA was precipitated in ethanol by adding 2 volumes of 100% ethanol and precipitating overnight at −20° C. The DNA was centrifuged at 10000 rpm in HB-6 rotor for 20 minutes at 4° C. The ethanol was discarded and the pellets resuspended in 700 uL 70% ethanol. The resuspended pellets were centrifuged at 14000 rpm for 10 minutes at 4° C. The ethanol was discarded and the pellets dried by vacuum.

Oligosaccharides were then removed by resuspending the pellet in 50 uL TE, pH 8. The solutions were frozen on dry ice for 10 minutes and centrifuged at 14000 rpm for 15 minutes at 4° C. The supernatant was transferred to a new tube and the volume recorded.

The concentration of DNA was determined by measuring absorbance at 260/280. DNA was diluted 1:100 in a quartz cuvette (3 uL DNA+297 uL TE). The following equation was used to calculate DNA concentration:

$$(32 \text{ ug/mL} * OD)(mL/100 \text{ uL})(100)(OD260) = \text{DNA concentration}$$

The preferred purity ratio was 1.7-2.0.

The DNA was diluted to 1 ug/uL with TB, pH 8 and stored at 4° C.

To test the quality of single-stranded DNA (ssDNA) the following reaction mixtures were prepared:
1. DNA mix per reaction
   a. 1 uL of 5 ng/uL ssDNA (1:200 dilution of VI.D.2 above)
   b. 11 uL dH2O
   c. 1.5 uL 10 uM T7 SPORT primer (fresh dilution of stock)
   d. 1.5 uL 10× Precision-Taq buffer
2. Repair mix per reaction
   a. 4 uL 5 mM dNTPs (1.25 mM each)
   b. 1.5 uL 10× Precision-Taq buffer
   c. 9.25 uL dH2O
   d. 0.25 uL Precision-Taq polymerase
   e. Preheat cocktail at 70° C. until middle of thermal cycle The DNA mixes were aliquoted into PCR tubes and thermal cycle carried out as follows:
1. 95° C., 20 sec
2. 59° C., 1 min; add 15 uL repair mix
3. 73° C., 23 min Ethanol precipitation of the ssDNA was performed by adding 15 ug glycogen, 16 uL 7.5 M $NH_4OAc$, 125 uL 100% ethanol. The sample was centrifuged at 14000 rpm for 30 minutes at 4° C. and the pellet washed with 125 uL 70% ethanol. The ethanol was discarded and pellet dried by vacuum. The pellet was resuspended in 10 uL TB, pH 8.

The DNA was electroporated into DH10B or DH12S cells. A DNA mixture consisting of:
1. 2 uL repaired library (=1.0×10−3 ug)
2. 1 uL 1 ng/uL unrepaired library (=1.0×10−3 ug)
3. 1 uL 0.01 ug/uL pUC19 positive control DNA (=1×10−5 ug)

was aliquoted to Eppendorf tubes. Cells were thawed on ice-water. Forty uL of cells were added to each DNA aliquot by pipetting into a chilled cuvette placed between metal plates. Electroporation was carried out at 1.8 kV. Immediately following electroporation, 1 mL SOC(SOB+glucose+$Mg^{++}$) media was added to the cuvette, then transferred to a 15 mL tube. Cells were allowed to recover for 1 hr at 37° C. with shaking (225 rpm). Cells were then plated according to the following dilution scheme:

A. Dilutions of Culture
1. Serial dilutions of culture in 1:10 increments (20 uL into 180 uL LB broth)
2. Repaired dilutions
   a. 1:100
   b. 1:1K
   c. 1:10K
3. Unrepaired dilutions
   a. 1:10
   b. 1:100
4. Positive control dilutions
   a. 1:10
   b. 1:100

100 uL of each dilution was plated on small LB+carb plates and incubated at 37° C. overnight. Colonies were counted to calculate titer as follows:
1. use smallest countable dilution
2. (# of colonies)(dilution factor)(200 uL/100 uL)(1000 uL/20 uL)=CFUs
3. CFUs/ug DNA used=CFU/ug % Background=(unrepaired CFU/ug/repaired CFU/ug)×100%

Example 4

Method of Cloning the Novel Human hSLAP-2v3 and v2 Polypeptides of the Present Invention One microliter of anti-sense biotinylated oligos (or sense oligos when annealing to single stranded DNA from pSPORT2 vector), containing one hundred and fifty nanograms of 1 to 50 different 80mer oligo probes, was added to six microliters (six micrograms) of a mixture of up to 15 single-stranded covalently closed circular cDNA libraries and seven microliters of 100% formamide in a 0.5 ml PCR tube. The sequence of the 80mer oligo used was as follows:

```
                                             (SEQ ID NO: 8)
5'-AGGATGCAGGGCGGCTGAGGCGGACTGACAGAGAGTAAGAGCCTCTC

CTGGTCTGGCTCTCCCGGATGAGGAAGGCCCCT -3'.
```

The mixture was heated in a thermal cycler to 95° C. for 2 min. Fourteen microliters of 2× hybridization buffer (50% formamide, 1.5 M NaCl, 0.04 M NaPO$_4$, pH 7.2, 5 min EDTA, 0.2% SDS) was added to the heated probe/cDNA library mixture and incubated at 42° C. for 26 hours. Hybrids between the biotinylated oligo and the circular cDNA were isolated by diluting the hybridization mixture to 220 microliters solution containing 1 M NaCl, 10 mm Tris-HCl pH 7.5, 1 mM EDTA, pH 8.0 and adding 125 microliters of streptavidin magnetic beads. This solution was incubated at 42° C. for 60 min, and mixed every 5 min to re-suspend the beads. The beads were separated from the solution with a magnet and washed three times in 200 microliters of 0.1×SSPE, 0.1% SDS at 45° C.

The single stranded cDNA was released from the biotinylated oligo/streptavidin magnetic bead complex by adding 50 microliters of 0.1 N NaOH and incubating at room temperature for 10 min. Six microliters of 3 M sodium acetate was added along with 15 micrograms of glycogen and the solution ethanol precipitated with 120 microliters of 100% ethanol. The precipitated DNA was resuspended in 12 microliters of TB (10 mM TrisHCl, pH 8.0), 1 mM EDTA, pH 8.0). The single-stranded cDNA was converted into double-stranded DNA in a thermal cycler by mixing 5 microliters of the captured DNA with 1.5 microliters of 10 micromolar standard SP6 primer for libraries in pSPORT 1 and 2 and 17 primer for libraries in pCMVSPORT and 1.5 microliters of 10×PCR buffer.

Sequences of primers used to repair single-stranded circular DNA isolated from the primary selection were as follows:

```
T7Sport5'-TAATACGACTCACTATAGGG-3'   (SEQ ID NO: 9)

SP6Sport5'- ATTTAGGTGACACTATAG -3'  (SEQ ID NO: 10)
```

The mixture was heated to 95° C. for 20 seconds and the temperature gradually brought down to 59° C. Fifteen microliters of a repair mix, that was preheated to 70° C. was added to the DNA (repair mix contains 4 microliters of 5 mM dNTPs (1.25 mM each), 1.5 microliters of 10×PCR buffer, 9.25 microliters of water, and 0.25 microliters of Taq polymerase). The solution incubation temperature was raised back to 73° C. and incubated for 23 mm. The repaired DNA was ethanol precipitated and resuspended in 10 microliters of TB. Electroporation was carried out using two microliters DNA per 40 microliters of E. coli DH12S cells. Three hundred and thirty three microliters were plated onto one 150-mm plate of LB agar plus 100 micrograms/milliliter of ampicillin. After overnight incubation at 37° C., the colonies from all plates were harvested by scraping into 10 ml of LB medium+50 micrograms/milliliter of ampicillin and 2 ml of sterile glycerol.

The second round of selection was initiated by making single-stranded circular DNA from the primary selected library using the method listed above. The purified single-stranded circular DNA was then assayed with gene-specific primers for each of the targeted sequences using standard PCR conditions.

The sequences of the Gene-Specific-Primer ("GSP") pairs used to identify the targeted hSLAP-2 cDNAs in the primary selected single stranded cDNA libraries were as follows:

```
                                        (SEQ ID NO: 11)
   hSLAP-2 Left Primer 1:    AGGTGGCTGTATGAGGGC (SEQ ID NO: 12)
   hSLAP-2 Right Primer 1:   TCTCCTGGTCTGGCTCTCC
```

The secondary hybridization was carried out using only those 80mer biotinylated probes whose targeted sequences were positive with the GSPs. The resulting single-stranded circular DNA was converted to double strands using the anti-sense oligo for each target sequence as the repair primer (the sense primer was used for material captured from pSPORT2 libraries. The resulting double stranded DNA was electroporated into DH10B and the resulting colonies inoculated into 96 deep well blocks. Following overnight growth, DNA was prepared and sequentially screened for each of the targeted sequences using the GSPs. The DNA was also cut with Sal I and Not I and the inserts sized by agarose gel electrophoresis.

Those cDNA clones that were positive by PCR had the inserts sized and two clones were chosen for DNA sequencing for each gene. Two splice variants of hSLAP-2 (SEQ ID NO:7) were identified and named hSLAP-2v3 and hSLAP-2v4. The full-length sequence of hSLAP-2v3 is provided in FIGS. 1A-B (SEQ ID NO:1) and the full-length sequence of hSLAP-2v4 is provided in FIGS. 2A-B (SEQ ID NO:3).

Example 5

Functional Demonstration that hSLAP-2 is a Negative Regulator of Intracellular T-Cell Signal Transduction The function of hSLAP-2 as a negative regulator of intracellular T-cell signal transduction has already been described in co-pending U.S. Ser. No. 09/988,971, filed Nov. 20, 2001 (Bristol-Myers Squibb Company), now U.S. Pat. No. 7,101, 686; and demonstrated to have such activity in WO 02/42452, published May 30$^{th}$, 2002; Holland et al (J. Exp. Med., 194

(9):1263-1276 (2001); Pandey et al (J. Biol. Chem., 277(21): 19131-19138 (2002), and Loreto et al (Mol. Cell. Biol., 22(12):4241-4255 (2002).

Materials and Methods

Both the transfection and NFAT luciferase experiments were performed essentially as described in Loreto, McGlade, Liu et al. (Curr. Biol., 1999, Vol. 9:67-75)("Liu") and Berry et al. (Oncogene 2001, Vol. 20: 1203-1211)("Berry") except that the Jurkat cells were stably transfected with the NFAT reporter construct and electroporation conditions were modified (300 V, 975 uF).

Cell lines. Jurkat NFAT4 mmx is a Jurkat/NFAT-promoter reporter cell line constructed with the NFAT promoter linked to the luciferase gene in a pGL3 vector and stably transfected into the Jurkat cell line (Molecumetics, Bellevue, Wash.).

Cell Culture. The Jurkat/NFAT promoter-luciferase cell line was maintained in culture media of RPMI Medium 1640 (Gibco Cat. No. 11875-085, Grand Island, N.Y.)/10% FBS (Gibco Cat. No. 16140-071 Grand Island, N.Y.), 1× Penicillin-Streptomycin (Gibco Cat. No. 15140-122, Grand Island, N.Y.)/20 mM L-Glutamine (Gibco Cat. No. 25030-081, Grand Island, N.Y.) and 500 ug/ml GENETICIN® (Gibco Cat. No. 10131-035 Grand Island, N.Y.).

Constructs. SLAP-2_GFP plasmid and the Control_GFP plasmid were constructed by conventional techniques. SLAP-2_GFP included an insert encoding the following polypeptide:

(SEQ ID NO: 7)
MGSLPSRRKSLPSPSLSSSVQGQGPVTMEAERSKATAVALGSFPAGGPAE

LSLRLGEPLTIVSEDGDWWTVLSEVSGREYNIPSVHVAKVSHGWLYEGLS

REKAEELLLLPGNPGGAFLIRESQTRRGSYSLSVRLSRPASWDRIRHYRI

HCLDNGWLYISPRLTFPSLQALVDHYSELADDICCLLKEPCVLQRAGPLP

GKDIPLPVTVQRTPLNWKELDSSLLFSEAATGEESLLSEGLRESLSFYIS

LNDEAVSLDDAKGGRADPAFLYKVVDLEGPRFEQKLISEEDLNMHTGHHH

HHH.

The Control_GFP plasmid contains an arbitrary gene insert for control purposes. Both are in a GFP vector, a pcDNA base with a Gateway cassette, myc and His tag epitopes, IRES element and eGFP sequence. The eGFP was used to assess transfection efficiency.

Transient transfections. Exponentially growing Jurkat/NFAT promoter-luciferase cells were spun down and resuspended in RPMI Medium 1640 at 1×10$^7$ cells/ml in aliquots of 800 µl. Each aliquot of cells received 0, 20 µg or 40 µg of SLAP-2_GFP plasmid or Control_GFP plasmid. The cell/DNA mixture was incubated at room temperature for ten minutes, transferred to a 0.4 cm GENE PULSER® Cuvette (Bio-Rad cat. No. 165-2088, Hercules, Calif.) and then electroporated (300 V, 975 µF) in a GENE PULSER® II (Bio-Rad, Hercules, Calif.), following manufacturer's instructions. The electroporated cell/DNA mixture was placed on ice for teen minutes and then transferred to a T25 flask containing 10 ml of culture media. Cells were incubated for 40 hours at 37° C., 5% $CO_2$.

NFAT promoter-luciferase assays. At 40 hours after transfection, cells were centrifuged and resuspended in assay media (RPMI Medium 1640 without phenol red (Gibco Cat. No. 11835-030, Grand Island, N.Y.)/10% Charcoal/Dextran treated-FBS (HyClone Cat. No. SH30068.03)/1× Penicillin-Streptomycin (Gibco Cat. No. 15140-122)/20 mM L-Gln (Gibco Cat. No. 25030-081, Grand Island, N.Y.). Six replicates of each transfection were plated in 96-well assay plates (CulturePlate-96, PerkinElmer Cat. No. 6005680, Boston, Mass.) at 40,000 viable cells/well in a 100 µl volume. The cells were either left unstimulated or stimulated with 0.5 µg/ml final concentration of anti-human CD3 antibody, clone G19-4 (Bristol-Myers Squibb Company, Princeton, N.J.), and incubated at 37° C., 5% $CO_2$. After six hours, 20 µl of STEADY-GLO® substrate from the Luciferase Assay System (Promega Cat. No. E2510, Madison Wis.) was added to each well and the lucifease activity was measured with a TOPCOUNT® NXT (Packard/PerkinElmer, Boston, Mass.). See Liu and Berry.

Flow cytometry. Assessment of transfection efficiency by FACs analysis. About 1×10$^6$ cells were harvested and resuspended in phosphate-buffered saline (PBS)/and then analysed using a FACScan (BD, San Jose, Calif.). GFP fluorescence was excited at 488 nm and emission was measured with a 530/30 nm bandpass filter. The gate was set on live cells. Histograms for green fluorescent protein-positive cells were created by using CellQuest software.

Results

To determine the effect of hSLAP-2 on T cell receptor signaling, NFAT activation was measured using a NFAT promoter-luciferase reporter system. Jurkat/NFAT promoter-luciferase cells was transiently transfected with 20 µg and 40 µg of hSLAP-2_GFP or a control_GFP DNA and its effect was examined on luciferase activity 40 hours post-transfection and after stimulation with anti-human CD3 antibody for six hours. Transfection efficiency was measured by FACs analysis (see FIG. 6). The results are consistent with other findings (see Holland, Pandey, Loreto, and McGlade) that show that transfection of 40 µg of hSLAP-2 DNA into a T-cell NFAT promoter-luciferase reporter cell system significantly inhibits anti-CD3-induced NFAT promoter activation with a p-value of 1×10$^{10}$. Transfection with 20 ug of hSLAP-2_GFP DNA did not show a significant amount of inhibition when compared to the control.

Activation of anti-CD3 triggers an intracellular signaling cascade that leads to the activation of specific nuclear transcription factors, including NFAT. As shown in FIG. 7, hSLAP-2 inhibits anti-human CD3 antibody mediated NFAT promoter activation in a Jurkat cell line. These results are consistent with other findings that show that overexpression of SLAP-2 negatively regulates T cell receptor signaling. See, for instance, Holland, Pandey, Loreto, and McGlade.

Since hSLAP-2v3 and hSLAP-2v4 are minor variants of hSLAP-2 and have both the SH2 and SH3 domains required for SLAP adaptor protein function, it is expected that hSLAP-2v3 and hSLAP-2v4 would both be capable of negatively regulating intracellular T-cell signaling as well. The results provided in Example 6 and outlined in FIG. 8 confirm that both hSLAP-2v3 and hSLAP-2v4 retain wild-type function.

Example 6

Functional Demonstration that Both hSLAP-2v3 and hSLAP-2v4 are also Negative Regulators of Intracellular T-Cell Signal Transduction In order to examine the intracellular T-cell signaling activity of hSLAP-2v3 and hSLAP-2v4, the following experiments were performed.

Materials and Methods

Both the transfection and NFAT luciferase experiments were performed essentially as described in Loreto, McGlade, Liu et al. (*Curr. Biol.*, 1999, Vol. 9:67-75)("Liu") and Berry et al. (*Oncogene* 2001, Vol. 20: 1203-1211)("Berry") except that the Jurkat cells were stably transfected with the NFAT reporter construct, electroporation conditions were modified (300 V, 975 uF), and the stably transfected NFAT reporter cells were transiently transfected using the DUAL-GLO® Luciferase Assay System (Promega, Catalog No. E2920).

Cell lines. Jurkat NFAT4 mmx is a Jurkat/NFAT-promoter reporter cell line constructed with the NFAT promoter linked to the luciferase gene in a pGL3 vector and stably transfected into the Jurkat cell line (Molecumetics, Bellevue, Wash.).

Cell Culture. The Jurkat/NFAT promoter-luciferase cell line was maintained in culture media of RPMI Medium 1640 (Gibco Cat. No. 11875-085, Grand Island, N.Y.)/10% FBS (Gibco Cat. No. 16140-071 Grand Island, N.Y.), 1× Penicillin-Streptomycin (Gibco Cat. No. 15140-122, Grand Island, N.Y.)/20 mM L-Glutamine (Gibco Cat. No. 25030-081, Grand Island, N.Y.) and 500 ug/ml GENETICIN® (Gibco Cat. No. 10131-035 Grand Island, N.Y.).

Constructs. Luciferase vectors containing the coding region for the wild-type SLAP-2 (SEQ ID NO:7), hSLAP-2v3 (SEQ ID NO:2), and hSLAP-2v4 (SEQ ID NO:4) were constructed by conventional techniques. The Control plasmid contains an arbitrary gene insert (ADF) for control purposes. An expression construct containing the renilla coding region was included in each transfection to assess transfection efficiency and to normalize the data.

Transient transfections. Exponentially growing Jurkat/NFAT promoter-luciferase cells ($10 \times 10^6$ cells into 15-ml blue capped tubes) were spun down and resuspended in 750 µl cold OptiMem per tube. Each aliquot of cells received 40 µg of SLAP-2, hSLAP-2v3, hSLAP-2v4, or Control plasmid, in addition to 1 µl of *Renilla* luciferase DNA (1.3 ug). One of the cell aliquots received only 1 µl of *Renilla* luciferase DNA (1.3 ug), and another received no DNA. The cell/DNA mixture was incubated at room temperature for ten minutes, transferred to a 0.4 cm GENE PULSER® Cuvette (Bio-Rad cat. No. 165-2088, Hercules, Calif.) and then electroporated (300 V, 975 µF) in a GENE PULSER® II (Bio-Rad, Hercules, Calif.), following manufacturer's instructions. The electroporated cell/DNA mixture was placed on ice for ten minutes and then transferred to a T25 flask containing 10 ml of culture media. Cells were incubated for 40 hours at 37° C., 5% $CO_2$.

NFAT promoter-luciferase assays. At 40 hours after transfection, cells were centrifuged and resuspended in 500 ml assay media (RPMI Medium 1640 without phenol red (Gibco Cat. No. 11835-030, Grand Island, N.Y.), 5 ml FBS (Gibco Cat. No. 16140-071), and 5 ml Penicillin-Streptomycin (Gibco Cat. No. 15140-122). Three replicates of each transfection were plated in 96-well assay plates (CulturePlate-96, PerkinElmer Cat. No. 6005680, Boston, Mass.) at 40,000 viable cells/well in a 100 µl volume. The cells were either left unstimulated or stimulated with 1.0 µg/ml final concentration of anti-human CD3 antibody, clone G19-4 (Bristol-Myers Squibb Company, Princeton, N.J.), and incubated at 37° C., 5% $CO_2$. After six hours, 30 µl of room temperature DUAL-GLO® Luciferase Substrate from the Luciferase Assay System (Promega Cat. No. E2920, Madison Wis.) was added to each well. After at least ten minutes at room temperature, measure Firefly luciferase activity with the TOPCOUNT® NXT (Packard/PerkinElmer, Boston, Mass.). Dilute the room temperature DUAL-GLO® Stop & Glo Reagent 1:100 into the room temperature Buffer. Then 30 µl of this diluted solution was added to each well. After ten minutes at room temperature, measure *Renilla* luciferase activity was measured with a TOPCOUNT® NXT (Packard/PerkinElmer, Boston, Mass.).

Transfection efficiencies were controlled by normalizing the luciferase reporter counts with the renilla reported counts. The resulting normalized data is provided in FIG. 8.

As shown, all of the SLAP-2 constructs appeared to inhibit the NFAT-luciferase activity compared to the control ADF plasmid in this Jurkat NFAT reporter luciferase assay using 40 ug of DNA per transfection. Accordingly, it is clear that both hSLAP-2v3 or hSLAP-2v4 retain wild-type T-cell negative signaling function of hSLAP-2.

Example 7

Complementary Polynucleotides

Anti-sense molecules or nucleic acid sequence complementary to the hSLAP-2v3 or hSLAP-2v4 protein-encoding sequence, or any part thereof, is used to decrease or to inhibit the expression of naturally occurring hSLAP-2v3 or hSLAP-2v4. Although the use of anti-sense or complementary oligonucleotides comprising about 15 to 35 base-pairs is described, essentially the same procedure is used with smaller or larger nucleic acid sequence fragments. An oligonucleotide based on the coding sequence of hSLAP-2v3 or hSLAP-2v4 proteins, as shown in FIGS. 1A-B and 2A-B, is used to inhibit expression of naturally occurring hSLAP-2v3 or hSLAP-2v4. The complementary oligonucleotide is designed from the most unique 5' sequence (FIG. 1A-B or 2A-B), and is used either to inhibit transcription by preventing promoter binding to the coding sequence, or to inhibit translation by preventing the ribosome from binding to the hSLAP-2v3 or hSLAP-2v4 protein-encoding transcripts. Using an appropriate portion of the signal and 5' sequence of SEQ ID NO:1 or SEQ ID NO:3, an effective anti-sense oligonucleotide includes any of about 15-35 nucleotides spanning the region which translates into the signal or 5' coding sequence of the polypeptide as shown in FIG. 1A-B or 2A-B. Appropriate oligonucleotides are designed using OLIGO 4.06 software and the hSLAP-2v3 or hSLAP-2v4 protein coding sequence (SEQ ID NO:2 or SEQ ID NO:4).

Example 8

Purification of Naturally Occurring hSLAP-2v3 or hSLAP-2v4 Proteins Using Specific Antibodies Naturally occurring or recombinant hSLAP-2v3 or hSLAP-2v4 polypeptides are substantially purified by immunoaffinity chromatography using antibodies specific for the hSLAP-2v3 or hSLAP-2v4 polypeptide2, or a peptide derived therefrom. An immunoaffinity column is constructed by covalently coupling polypeptide antibody raised against hSLAP-2v3 or hSLAP-2v4 to an activated chromatographic resin, such as CNBr-activated SEPHAROSE® (Amersham Pharmacia Biotech, Inc.; Piscataway, N.J.). After the coupling, the resin is blocked and washed according to the manufacturer's instructions.

Medium containing hSLAP-2v3 or hSLAP-2v4 polypeptide is passed over the immunoaffinity column, and the column is washed under conditions that allow the preferential absorbance of the hSLAP-2v3 or hSLAP-2v4 polypeptides (e.g., high ionic strength buffers in the presence of detergent). The column is eluted under conditions that disrupt antibody/hSLAP-2v3 or hSLAP-2v4 polypeptides binding (e.g., a buffer of pH 2-3, or a high concentration of a chaotrope, such as urea or thiocyanate ion), and hSLAP-2v3 or hSLAP-2v4 polypeptide is collected.

Example 9

Identification of Molecules that Interact with the Human hSLAP-2v3 or hSLAP-2v4 Proteins hSLAP-2v3 or hSLAP-2v4 polypeptides, or biologically active fragments thereof, are labeled with $^{125}$I Bolton-Hunter reagent (Bolton et al., 1973, *Biochem. J.,* 133:529). Candidate molecules previously arrayed in wells of a multi-welled plate are incubated with the labeled hSLAP-2v3 or hSLAP-2v4 polypeptides, washed, and any wells having labeled hSLAP-2v3 or hSLAP-2v4 polypeptide-candidate molecule complexes are assayed. Data obtained using different concentrations of the hSLAP-2v3 or hSLAP-2v4 polypeptides are used to calculate values for the number, affinity and association of the hSLAP-2v3 or hSLAP-2v4 polypeptides with the candidate molecules. In addition, data may be obtained using fusion proteins such as GST- or polyhistidine tagged fusion proteins, co-immunoprecipitation and/or Western immunoblotting, etc.

Example 10

Expression Profiling of the Novel Human hSLAP-2v3 or hSLAP-2v4 Polypeptides

The following PCR primer pair may be used to measure the steady state levels of hSLAP-2v3 or hSLAP-2v4 mRNA by quantitative PCR:

| GPCR Clone | Expression Profile Oligo Sequence |
|---|---|
| hSLAP-2v3-s | AGGTGGCTGTATGAGGGC (SEQ ID NO: 11) |
| hSLAP-2v3-a | TCTCCTGGTCTGGCTCTCC (SEQ ID NO: 12) |

Briefly, first strand cDNA may be made from commercially available mRNA. The relative amount of cDNA used in each assay can be determined by performing a parallel experiment using a primer pair for a gene expressed in equal amounts in all tissues, cyclophilin. The cyclophilin primer pair would ideally detect small variations in the amount of cDNA in each sample and these data can then be used for normalization of the data obtained with the primer pair for this gene. The PCR data may be converted into a relative assessment of the difference in transcript abundance amongst the tissues tested.

Example 11

Bacterial Expression of a Polypeptide

A polynucleotide encoding a polypeptide of the present invention is amplified using PCR oligonucleotide primers corresponding to the 5' and 3' ends of the DNA sequence, as outlined herein, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Ampr), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the *E. coli* strain M15/rep4 (Qiagen, Inc.) which contains multiple copies of the plasmid pREP4, that expresses the lad repressor and also confers kanamycin resistance (Kanr). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D. 600) of between 0.4 and 0.6. IPTG (Isopropyl-B-D-thiogalacto pyranoside) is then added to a final concentration of 1 mM. IPTG induces by inactivating the lad repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3-4 hours at 4 degree C. The cell debris is removed by centrifugation, and the supernatant containing the polypeptide is loaded onto a nickel-nitrilo-triacetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM imidazole. Imidazole is removed by a final dialyzing step against PBS or 50 mM sodium acetate pH 6 buffer plus 200 mM NaCl. The purified protein is stored at 4 degree C. or frozen at −80 degree C.

Example 12

Cloning and Expression of a Polypeptide in a Baculovirus Expression System

In this example, the plasmid shuttle vector pAc373 is used to insert a polynucleotide into a baculovirus to express a polypeptide. A typical baculovirus expression vector contains the strong polyhedrin promoter of the *Autographa californica* nuclear polyhedrosis virus (AcMNPV) followed by convenient restriction sites, which may include, for example BamHI, Xba I and Asp718. The polyadenylation site of the simian virus 40 ("SV40") is often used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31-39 (1989).

A polynucleotide encoding a polypeptide of the present invention is amplified using PCR oligonucleotide primers corresponding to the 5' and 3' ends of the DNA sequence to synthesize insertion fragments. The primers used to amplify the cDNA insert should preferably contain restriction sites at the 5' end of the primers in order to clone the amplified product into the expression vector. Specifically, the cDNA sequence contained in the deposited clone, including the AUG initiation codon and the naturally associated leader sequence identified elsewhere herein (if applicable), is amplified using the PCR protocol. If the naturally occurring signal sequence is used to produce the protein, the vector used does not need a second signal peptide. Alternatively, the vector can be modified to include a baculovirus leader sequence, using the standard methods described in Summers et al., "A Manual of Methods for Baculovirus Vectors and Insect Cell Culture Procedures" Texas Agricultural Experimental Station Bulletin No. 1555 (1987).

The amplified fragment is isolated from a 1% agarose gel using a commercially available kit ("GENECLEAN®" BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("GENECLEAN®" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transformed with 1.0 ug of a commercially available linearized baculovirus DNA ("BACULOGOLD®" baculovirus DNA", Pharmingen, San Diego, Calif.), using the lipofection method described by Felgner et al., Proc. Natl. Acad. Sci. USA. 84:7413-7417 (1987). One ug of BACULOGOLD® virus DNA and 5 ug of the plasmid are mixed in a sterile well of a microtiter plate containing 50 ul of serum-free Grace's medium (Life Technologies Inc., Gaithersburg, Md.). Afterwards, 10 ul LIPOFECTIN® plus 90 ul Grace's medium are added, mixed and incubated for 15 minutes at room temperature. Then the transfection mixture is added drop-wise to Sf9 insect cells (ATCC® CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9-10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of 35S-methionine and 5 uCi 35S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 13

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC® 37152), pSV2dhfr (ATCC® 37146), pBC12MI (ATCC® 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transformation with a selectable marker such as dhfr, gpt, neomycin, hygromycin allows the identification and isolation of the transformed cells.

The transformed gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357-1370 (1978); Hamlin, J. L. and Ma, C., Biochem. et Biophys. Acta, 1097:107-143 (1990); Page, M. J. and Sydenham, M. A., Biotechnology 9:64-68 (1991).) Another useful selection marker is the enzyme glutamine synthase (GS) (Murphy et al., Biochem J. 227:277-279 (1991); Bebbington et al., Bio/Technology 10:169-175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

A polynucleotide of the present invention is amplified according to the protocol outlined in herein. If the naturally occurring signal sequence is used to produce the protein, the vector does not need a second signal peptide. Alternatively, if the naturally occurring signal sequence is not used, the vector can be modified to include a heterologous signal sequence. (See, e.g., WO 96/34891.) The amplified fragment is isolated from a 1% agarose gel using a commercially available kit ("GENECLEAN®" BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. E. coli HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transformation. Five µg of an expression plasmid is cotransformed with 0.5 ug of the plasmid pSVneo using LIPOFECTIN® (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100-200 uM. Expression of the desired gene product is analyzed, for instance, by SDS-PAGE and Western blot or by reversed phase HPLC analysis.

Example 14

Method of Creating N- and C-Terminal Deletion Mutants Corresponding to the hSLAP-2v3 and hSLAP-2v4 Polypeptide of the Present Invention As described elsewhere herein, the present invention encompasses the creation of N- and C-terminal deletion mutants, in addition to any combination of N- and C-terminal deletions thereof, corresponding to the hSLAP-2v3 and hSLAP-2v4 polypeptide of the present invention. A number of methods are available to one skilled in the art for creating such mutants. Such methods may include a combination of PCR amplification and gene cloning methodology. Although one of skill in the art of molecular biology, through the use of the teachings provided or referenced herein, and/or otherwise known in the art as standard methods, could readily create each deletion mutant of the present invention, exemplary methods are described below.

Briefly, using the isolated cDNA clone encoding the full-length hSLAP-2v3 or hSLAP-2v4 polypeptide sequence, appropriate primers of about 15-25 nucleotides derived from the desired 5' and 3' positions of SEQ ID NO:1 or SEQ ID NO:3 may be designed to PCR amplify, and subsequently clone, the intended N- and/or C-terminal deletion mutant. Such primers could comprise, for example, an initiation and stop codon for the 5' and 3' primer, respectively. Such primers may also comprise restriction sites to facilitate cloning of the deletion mutant post amplification. Moreover, the primers may comprise additional sequences, such as, for example, flag-tag sequences, kozac sequences, or other sequences discussed and/or referenced herein.

Representative PCR amplification conditions are provided below, although the skilled artisan would appreciate that other conditions may be required for efficient amplification. A 100 ul PCR reaction mixture may be prepared using 10 ng of the template DNA (cDNA clone of hSLAP-2v3 and hSLAP-2v4), 200 uM 4dNTPs, 1 uM primers, 0.25 U Taq DNA polymerase (PE), and standard Taq DNA polymerase buffer. Typical PCR cycling condition are as follows:

| | |
|---|---|
| 20-25 cycles: | 45 sec, 93 degrees |
| | 2 min, 50 degrees |
| | 2 min, 72 degrees |
| 1 cycle: | 10 min, 72 degrees |

After the final extension step of PCR, 5 U Klenow Fragment may be added and incubated for 15 min at 30 degrees.

Upon digestion of the fragment with the NotI and SaiI restriction enzymes, the fragment could be cloned into an appropriate expression and/or cloning vector which has been similarly digested (e.g., pSport1, among others). The skilled artisan would appreciate that other plasmids could be equally substituted, and may be desirable in certain circumstances. The digested fragment and vector are then ligated using a DNA ligase, and then used to transform competent E. coli cells using methods provided herein and/or otherwise known in the art.

The 5' primer sequence for amplifying any additional N-terminal deletion mutants may be determined by reference to the following formula: (S+(X*3)) to ((S+(X*3))+25), wherein 'S' is equal to the nucleotide position of the initiating start codon of the hSLAP-2v3 or hSLAP-2v4 gene (SEQ ID NO:1 or SEQ ID NO:3), and 'X' is equal to the most N-terminal amino acid of the intended N-terminal deletion mutant. The first term will provide the start 5' nucleotide position of the 5' primer, while the second term will provide the end 3' nucleotide position of the 5' primer corresponding to sense strand of SEQ ID NO:1 or SEQ ID NO:3. Once the corresponding nucleotide positions of the primer are determined, the final nucleotide sequence may be created by the addition of applicable restriction site sequences to the 5' end of the sequence, for example. As referenced herein, the addition of other sequences to the 5' primer may be desired in certain circumstances (e.g., kozac sequences, etc.).

The 3' primer sequence for amplifying any additional N-terminal deletion mutants may be determined by reference to the following formula: (S+(X*3)) to ((S+(X*3))-25), wherein 'S' is equal to the nucleotide position of the initiating start codon of the hSLAP-2v3 or hSLAP-2v4 gene (SEQ ID NO:1 or SEQ ID NO:3), and 'X' is equal to the most C-terminal amino acid of the intended N-terminal deletion mutant. The first term will provide the start 5' nucleotide position of the 3' primer, while the second term will provide the end 3' nucleotide position of the 3' primer corresponding to the anti-sense strand of SEQ ID NO:1 or SEQ ID NO:3. Once the corresponding nucleotide positions of the primer are determined, the final nucleotide sequence may be created by the addition of applicable restriction site sequences to the 5' end of the sequence, for example. As referenced herein, the addition of other sequences to the 3' primer may be desired in certain circumstances (e.g., stop codon sequences, etc.). The skilled artisan would appreciate that modifications of the above nucleotide positions may be necessary for optimizing PCR amplification.

The same general formulas provided above may be used in identifying the 5' and 3' primer sequences for amplifying any C-terminal deletion mutant of the present invention. Moreover, the same general formulas provided above may be used in identifying the 5' and 3' primer sequences for amplifying any combination of N-terminal and C-terminal deletion mutant of the present invention. The skilled artisan would appreciate that modifications of the above nucleotide positions may be necessary for optimizing PCR amplification.

Example 15

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example described herein; see also EPA 394,827; Traunecker, et al., Nature 331:84-86 (1988).) Similarly, fusion to IgG-1, IgG-3, and albumin increases the half-life time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector. Note that the polynucleotide is cloned without a stop codon, otherwise a fusion protein will not be produced.

The naturally occurring signal sequence may be used to produce the protein (if applicable). Alternatively, if the naturally occurring signal sequence is not used, the vector can be modified to include a heterologous signal sequence. (See, e.g., WO 96/34891 and/or U.S. Pat. No. 6,066,781, supra.)

Human IgG Fc Region (SEQ ID NO: 13)
GGGATCCGGAGCCCAAATCTTCTGACAAAACTCACACATGCCCACCGTGC

CCAGCACCTGAATTCGAGGGTGCACCGTCAGTCTTCCTCTTCCCCCCAAA

ACCCAAGGACACCCTCATGATCTCCCGGACTCCTGAGGTCACATGCGTGG

TGGTGGACGTAAGCCACGAAGACCCTGAGGTCAAGTTCAACTGGTACGTG

GACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

ACCCCCATCGAGAAAACCATCTCCAAAGCCAAAGGGCAGCCCCGAGAACC

ACAGGTGTACACCCTGCCCCCATCCCGGGATGAGCTGACCAAGAACCAGG

TCAGCCTGACCTGCCTGGTCAAAGGCTTCTATCCAAGCGACATCGCCGTG

GAGTGGGAGAGCAATGGGCAGCCGGAGAACAACTACAAGACCACGCCTCC

CGTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGG

GTAAATGAGTGCGACGGCCGCGACTCTAGAGGAT.

Example 16

Production of an Antibody from a Polypeptide

The antibodies of the present invention can be prepared by a variety of methods. (See, Current Protocols, Chapter 2.) As one example of such methods, cells expressing a polypeptide of the present invention are administered to an animal to induce the production of sera containing polyclonal antibodies. In a preferred method, a preparation of the protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563-681 (1981).) In general, such procedures involve immunizing an animal (preferably a mouse) with polypeptide or, more preferably, with a polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC®. After fusion, the resulting hybridoma cells are selectively maintained in HAT medium, and then cloned by limiting dilution as described by Wands et al. (Gastroenterology 80:225-232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones that produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and $F(ab')_2$ and other fragments of the antibodies of the present invention may be used according to the methods disclosed herein. Such fragments are typically produced by proteolytic cleavage, using enzymes such as papain (to produce Fab fragments) or pepsin (to produce $F(ab')_2$ fragments). Alternatively, protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 86/01533; Robinson et al., WO 87/02671; Boulianne et al., Nature 312:643 (1984); Neuberger et al., Nature 314:268 (1985).)

Moreover, in another preferred method, the antibodies directed against the polypeptides of the present invention may be produced in plants. Specific methods are disclosed in U.S. Pat. Nos. 5,959,177, and 6,080,560, which are hereby incorporated in their entirety herein. The methods not only describe methods of expressing antibodies, but also the means of assembling foreign multimeric proteins in plants (i.e., antibodies, etc.), and the subsequent secretion of such antibodies from the plant.

Example 17

Method of Enhancing the Biological Activity/Functional Characteristics of Invention Through Molecular Evolution Although many of the most biologically active proteins known are highly effective for their specified function in an organism, they often possess characteristics that make them undesirable for transgenic, therapeutic, and/or industrial applications. Among these traits, a short physiological half-life is the most prominent problem, and is present either at the level of the protein, or the level of the proteins mRNA. The ability to extend the half-life, for example, would be particularly important for a proteins use in gene therapy, transgenic animal production, the bioprocess production and purification of the protein, and use of the protein as a chemical modulator among others. Therefore, there is a need to identify novel variants of isolated proteins possessing characteristics which enhance their application as a therapeutic for treating diseases of animal origin, in addition to the proteins applicability to common industrial and pharmaceutical applications.

Thus, one aspect of the present invention relates to the ability to enhance specific characteristics of invention through directed molecular evolution. Such an enhancement may, in a non-limiting example, benefit the inventions utility as an essential component in a kit, the inventions physical attributes such as its solubility, structure, or codon optimization, the inventions specific biological activity, including any associated enzymatic activity, the proteins enzyme kinetics, the proteins $K_i$, $K_{cat}$, $K_m$, $V_{max}$, $K_d$, protein-protein activity, protein-DNA binding activity, antagonist/inhibitory activity (including direct or indirect interaction), agonist activity (including direct or indirect interaction), the proteins antigenicity (e.g., where it would be desirable to either increase or decrease the antigenic potential of the protein), the immunogenicity of the protein, the ability of the protein to form dimers, trimers, or multimers with either itself or other proteins, the antigenic efficacy of the invention, including its subsequent use a preventative treatment for disease or disease states, or as an effector for targeting diseased genes. Moreover, the ability to enhance specific characteristics of a protein may also be applicable to changing the characterized activity of an enzyme to an activity completely unrelated to its initially characterized activity. Other desirable enhancements of the invention would be specific to each individual protein, and would thus be well known in the art and contemplated by the present invention.

Directed evolution is comprised of several steps. The first step is to establish a library of variants for the gene or protein of interest. The most important step is to then select for those variants that entail the activity you wish to identify. The design of the screen is essential since your screen should be selective enough to eliminate non-useful variants, but not so stringent as to eliminate all variants. The last step is then to repeat the above steps using the best variant from the previous screen. Each successive cycle, can then be tailored as necessary, such as increasing the stringency of the screen, for example.

Over the years, there have been a number of methods developed to introduce mutations into macromolecules. Some of these methods include, random mutagenesis, "error-prone" PCR, chemical mutagenesis, site-directed mutagenesis, and other methods well known in the art (for a comprehensive listing of current mutagenesis methods, see Maniatis, Molecular Cloning: A Laboratory Manual, Cold Spring Harbor Press, Cold Spring, N.Y. (1982)). Typically, such methods have been used, for example, as tools for identifying the core functional region(s) of a protein or the function of specific domains of a protein (if a multi-domain protein). However, such methods have more recently been applied to the identification of macromolecule variants with specific or enhanced characteristics.

Random mutagenesis has been the most widely recognized method to date. Typically, this has been carried out either through the use of "error-prone" PCR (as described in Moore, J., et al, Nature Biotechnology 14:458, (1996), or through the application of randomized synthetic oligonucleotides corresponding to specific regions of interest (as described by Derbyshire, K. M. et al, Gene, 46:145-152, (1986), and Hill, D E, et al, Methods Enzymol., 55:559-568, (1987). Both approaches have limits to the level of mutagenesis that can be obtained. However, either approach enables the investigator to effectively control the rate of mutagenesis. This is particularly important considering the fact that mutations beneficial to the activity of the enzyme are fairly rare. In fact, using too high a level of mutagenesis may counter or inhibit the desired benefit of a useful mutation.

While both of the aforementioned methods are effective for creating randomized pools of macromolecule variants, a third method, termed "DNA Shuffling", or "sexual PCR" (WPC, Stemmer, PNAS, 91:10747, (1994)) has recently been elucidated. DNA shuffling has also been referred to as "directed molecular evolution", "exon-shuffling", "directed enzyme evolution", "in vitro evolution", and "artificial evolution". Such reference terms are known in the art and are encompassed by the invention. This new, preferred, method apparently overcomes the limitations of the previous methods in that it not only propagates positive traits, but simultaneously eliminates negative traits in the resulting progeny.

DNA shuffling accomplishes this task by combining the principal of in vitro recombination, along with the method of "error-prone" PCR. In effect, you begin with a randomly digested pool of small fragments of your gene, created by Dnase I digestion, and then introduce said random fragments into an "error-prone" PCR assembly reaction. During the PCR reaction, the randomly sized DNA fragments not only hybridize to their cognate strand, but also may hybridize to other DNA fragments corresponding to different regions of the polynucleotide of interest—regions not typically accessible via hybridization of the entire polynucleotide. Moreover, since the PCR assembly reaction utilizes "error-prone" PCR reaction conditions, random mutations are introduced during the DNA synthesis step of the PCR reaction for all of the fragments—further diversifying the potential hybridization sites during the annealing step of the reaction.

A variety of reaction conditions could be utilized to carry-out the DNA shuffling reaction. However, specific reaction conditions for DNA shuffling are provided, for example, in PNAS, 91:10747, (1994). Briefly:

Prepare the DNA substrate to be subjected to the DNA shuffling reaction. Preparation may be in the form of simply purifying the DNA from contaminating cellular material, chemicals, buffers, oligonucleotide primers, deoxynucleotides, RNAs, etc., and may entail the use of DNA purification kits as those provided by Qiagen, Inc., or by the Promega, Corp., for example.

Once the DNA substrate has been purified, it would be subjected to Dnase I digestion. About 2-4 ug of the DNA substrate(s) would be digested with 0.0015 units of Dnase I (Sigma) per ul in 100 ul of 50 mM Tris-HCL, pH 7.4/1 mM MgCl2 for 10-20 min. at room temperature. The resulting fragments of 10-50 bp could then be purified by running them through a 2% low-melting point agarose gel by electrophoresis onto DE81 ion-exchange paper (Whatmann) or could be purified using MICROCON® concentrators (Amicon) of the appropriate molecular weight cutoff, or could use oligonucleotide purification columns (Qiagen), in addition to other methods known in the art. If using DE81 ion-exchange paper, the 10-50 bp fragments could be eluted from said paper using 1M NaCl, followed by ethanol precipitation.

The resulting purified fragments would then be subjected to a PCR assembly reaction by re-suspension in a PCR mixture containing: 2 mM of each dNTP, 2.2 mM MgCl2, 50 mM KCl, 10 mM Tris•HCL, pH 9.0, and 0.1% Triton X-100, at a final fragment concentration of 10-30 ng/ul. No primers are added at this point. Taq DNA polymerase (Promega) would be used at 2.5 units per 100 ul of reaction mixture. A PCR program of 94 C for 60 s; 94 C for 30 s, 50-55 C for 30 s, and 72 C for 30 s using 30-45 cycles, followed by 72 C for 5 min using an MJ RESEARCH® (Cambridge, Mass.) PTC-150 thermocycler. After the assembly reaction is completed, a 1:40 dilution of the resulting primerless product would then be introduced into a PCR mixture (using the same buffer mixture used for the assembly reaction) containing 0.8 um of each primer and subjecting this mixture to 15 cycles of PCR (using 94 C for 30 s, 50 C for 30 s, and 72 C for 30 s). The referred primers would be primers corresponding to the nucleic acid sequences of the polynucleotide(s) utilized in the shuffling reaction. Said primers could consist of modified nucleic acid base pairs using methods known in the art and referred to else where herein, or could contain additional sequences (i.e., for adding restriction sites, mutating specific base-pairs, etc.).

The resulting shuffled, assembled, and amplified product can be purified using methods well known in the art (e.g., QIAGEN® PCR purification kits) and then subsequently cloned using appropriate restriction enzymes.

Although a number of variations of DNA shuffling have been published to date, such variations would be obvious to the skilled artisan and are encompassed by the invention. The DNA shuffling method can also be tailored to the desired level of mutagenesis using the methods described by Zhao, et al. (Nucl Acid Res., 25(6):1307-1308, (1997).

As described above, once the randomized pool has been created, it can then be subjected to a specific screen to identify the variant possessing the desired characteristic(s). Once the variant has been identified, DNA corresponding to the variant could then be used as the DNA substrate for initiating another round of DNA shuffling. This cycle of shuffling, selecting the optimized variant of interest, and then re-shuffling, can be repeated until the ultimate variant is obtained. Examples of model screens applied to identify variants created using DNA shuffling technology may be found in the following publications: J. C., Moore, et al., J. Mol. Biol., 272:336-347, (1997), F. R., Cross, et al., Mol. Cell. Biol., 18:2923-2931, (1998), and A. Crameri., et al., Nat. Biotech., 15:436-438, (1997).

DNA shuffling has several advantages. First, it makes use of beneficial mutations. When combined with screening, DNA shuffling allows the discovery of the best mutational combinations and does not assume that the best combination contains all the mutations in a population. Secondly, recombination occurs simultaneously with point mutagenesis. An effect of forcing DNA polymerase to synthesize full-length genes from the small fragment DNA pool is a background mutagenesis rate. In combination with a stringent selection method, enzymatic activity has been evolved up to 16000 fold increase over the wild-type form of the enzyme. In essence, the background mutagenesis yielded the genetic variability on which recombination acted to enhance the activity.

A third feature of recombination is that it can be used to remove deleterious mutations. As discussed above, during the process of the randomization, for every one beneficial mutation, there may be at least one or more neutral or inhibitory mutations. Such mutations can be removed by including in the assembly reaction an excess of the wild-type random-size fragments, in addition to the random-size fragments of the selected mutant from the previous selection. During the next selection, some of the most active variants of the polynucleotide/polypeptide/enzyme, should have lost the inhibitory mutations.

Finally, recombination enables parallel processing. This represents a significant advantage since there are likely multiple characteristics that would make a protein more desirable (e.g. solubility, activity, etc.). Since it is increasingly difficult to screen for more than one desirable trait at a time, other methods of molecular evolution tend to be inhibitory. However, using recombination, it would be possible to combine the randomized fragments of the best representative variants for the various traits, and then select for multiple properties at once.

DNA shuffling can also be applied to the polynucleotides and polypeptides of the present invention to decrease their immunogenicity in a specified host. For example, a particular variant of the present invention may be created and isolated using DNA shuffling technology. Such a variant may have all of the desired characteristics, though may be highly immunogenic in a host due to its novel intrinsic structure. Specifically, the desired characteristic may cause the polypeptide to have a non-native structure which could no longer be recognized as a "self" molecule, but rather as a "foreign", and thus activate a host immune response directed against the novel variant. Such a limitation can be overcome, for example, by including a copy of the gene sequence for a xenobiotic ortholog of the native protein in with the gene sequence of the novel variant gene in one or more cycles of DNA shuffling. The molar ratio of the ortholog and novel variant DNAs could be varied accordingly. Ideally, the resulting hybrid variant identified would contain at least some of the coding sequence which enabled the xenobiotic protein to evade the host immune system, and additionally, the coding sequence of the original novel variant that provided the desired characteristics.

Likewise, the invention encompasses the application of DNA shuffling technology to the evolution of polynucleotides and polypeptides of the invention, wherein one or more cycles of DNA shuffling include, in addition to the gene template DNA, oligonucleotides coding for known allelic sequences, optimized codon sequences, known variant sequences, known polynucleotide polymorphism sequences, known ortholog sequences, known homologue sequences, additional homologous sequences, additional non-homologous sequences, sequences from another species, and any number and combination of the above.

In addition to the described methods above, there are a number of related methods that may also be applicable, or desirable in certain cases. Representative among these are the methods discussed in PCT applications WO 98/31700, and WO 98/32845, which are hereby incorporated by reference. Furthermore, related methods can also be applied to the polynucleotide sequences of the present invention in order to evolve invention for creating ideal variants for use in gene therapy, protein engineering, evolution of whole cells containing the variant, or in the evolution of entire enzyme pathways containing polynucleotides of the invention as described in PCT applications WO 98/13485, WO 98/13487, WO 98/27230, WO 98/31837, and Crameri, A., et al., Nat. Biotech., 15:436-438, (1997), respectively.

Additional methods of applying "DNA Shuffling" technology to the polynucleotides and polypeptides of the present invention, including their proposed applications, may be found in U.S. Pat. No. 5,605,793; PCT Application No. WO 95/22625; PCT Application No. WO 97/20078; PCT Application No. WO 97/35966; and PCT Application No. WO 98/42832; PCT Application No. WO 00/09727 specifically provides methods for applying DNA shuffling to the identification of herbicide selective crops which could be applied to the polynucleotides and polypeptides of the present invention; additionally, PCT Application No. WO 00/12680 provides methods and compositions for generating, modifying, adapting, and optimizing polynucleotide sequences that confer detectable phenotypic properties on plant species; each of the above are hereby incorporated in their entirety herein for all purposes.

One skilled in the art could easily modify the exemplified studies to test the activity of polynucleotides of the invention (e.g., gene therapy), agonists, and/or antagonists of polynucleotides or polypeptides of the invention.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, GENBANK® Accession numbers, SWISS-PROT® Accession numbers, or other disclosures) in the Background of the Invention, Detailed Description, Brief Description of the Figures, and Examples is hereby incorporated herein by reference in their entirety. Further, the hard copy of the Sequence Listing submitted herewith, in addition to its corresponding Computer Readable Form, are incorporated herein by reference in their entireties.

What is claimed is:

1. An isolated nucleic acid molecule comprising a polynucleotide selected from the group consisting of:
   (a) a polynucleotide encoding a polypeptide comprising the amino acid sequence of amino acids 1 to 241 of SEQ ID NO:2; and
   (b) a polynucleotide encoding a polypeptide comprising the amino acid sequence of amino acids 2 to 241 of SEQ ID NO:2, wherein said polynucleotide of (a) and (b) is cDNA or mRNA.

2. The isolated nucleic acid molecule of claim 1, wherein said polynucleotide is (a).

3. The isolated nucleic acid molecule of claim 2, wherein said polynucleotide comprises nucleotides 29 to 751 of SEQ ID NO:1.

4. The isolated nucleic acid molecule of claim 1, wherein said polynucleotide is (b).

5. The isolated nucleic acid molecule of claim 4, wherein said polynucleotide comprises nucleotides 32 to 751 of SEQ ID NO:1.

6. A recombinant vector comprising the isolated nucleic acid molecule of claim 1.

7. An isolated recombinant host cell comprising the recombinant vector of claim 6.

8. A method of making and recovering a polypeptide comprising:
   (a) culturing the isolated recombinant host cell of claim 7 under conditions such that said polypeptide is expressed; and
   (b) recovering said polypeptide.

9. The isolated nucleic acid molecule of claim 1, wherein said nucleic acid molecule further comprises a heterologous nucleic acid.

10. The isolated nucleic acid molecule of claim 9 wherein said heterologous nucleic acid encodes a heterologous polypeptide and wherein said heterologous polypeptide is the Fc domain of immunoglobulin.

11. An isolated nucleic acid molecule comprising a nucleotide sequence that is at least 95.0% identical to a polynucleotide encoding a polypeptide comprising the amino acid sequence of amino acids 1 to 241 of SEQ ID NO:2, wherein percent identity is calculated using a CLUSTALW global sequence alignment using default parameters, and wherein said nucleotide sequence encodes a polypeptide that is capable of negatively regulating intracellular T-cell signal transduction in mammalian cells in which said polypeptide is recombinantly expressed wherein said isolated nucleic acid molecule is cDNA or mRNA.

12. An isolated nucleic acid molecule comprising a polynucleotide that encodes a polypeptide that is at least 95.0% identical to the amino acid sequence of SEQ ID NO:2, wherein percent identity is calculated using a CLUSTALW global sequence alignment using default parameters, and wherein said polypeptide is capable of negatively regulating intracellular T-cell signal transduction in mammalian cells in which said polypeptide is recombinantly expressed, wherein said polynucleotide is cDNA or mRNA.

13. An isolated nucleic acid molecule comprising a polynucleotide encoding a polypeptide comprising at least 222 contiguous amino acids of SEQ ID NO:2, wherein the encoded polypeptide is capable of negatively regulating intracellular T-cell signal transduction in mammalian cells in which said polypeptide is recombinantly expressed, wherein said polynucleotide is cDNA or mRNA.

14. The isolated nucleic acid molecule of claim 13, wherein said polynucleotide comprises at least 666 contiguous nucleotides of SEQ ID NO:1.

15. An isolated nucleic acid molecule comprising a cDNA that encodes the amino acid sequence of amino acids 1 to 241 of SEQ ID NO:2 contained in ATCC Deposit No. PTA-7622.

16. An isolated nucleic acid molecule comprising a polynucleotide that is fully complementary to the nucleotide sequence of the polynucleotide of (a) or (b) of claim 1.

17. An isolated nucleic acid molecule comprising a polynucleotide encoding a polypeptide comprising the amino acid sequence of amino acids 20 to 241 of SEQ ID NO:2, wherein the encoded polypeptide is capable of negatively regulating intracellular T-cell signal transduction in mammalian cells in which said polypeptide is recombinantly expressed, wherein said polynucleotide is cDNA or mRNA.

18. The isolated nucleic acid molecule of claim 17, wherein said nucleic acid molecule comprises nucleotides 86 to 751 of SEQ ID NO:1.

19. An isolated nucleic acid molecule comprising a polynucleotide encoding a polypeptide comprising the amino acid sequence of amino acids 1 to 222 of SEQ ID NO:2, wherein said encoded polypeptide is capable of negatively regulating intracellular T-cell signal transduction in mammalian cells in which said polypeptide is recombinantly expressed, wherein said polynucleotide is cDNA or mRNA.

20. The isolated nucleic acid molecule of claim 19, wherein said nucleic acid molecule comprises nucleotides 29 to 694 of SEQ ID NO:1.

* * * * *

SEQUENCE LISTING

<160> NUMBER OF SEQ ID NOS: 14

<210> SEQ ID NO 1
<211> LENGTH: 919
<212> TYPE: DNA
<213> ORGANISM: Homo sapiens
<220> FEATURE:

<221> NAME/KEY: CDS
<222> LOCATION: (29)..(751)

<400> SEQUENCE: 1

```
gtgcttctga gtgctctgct gaggaaca atg gga agt ctg ccc agc aga aga         52
                                Met Gly Ser Leu Pro Ser Arg Arg
                                  1               5 aaa tct ctg cca agc cca agc ttg agt tcc tct gtc caa ggc cag gga        100
Lys Ser Leu Pro Ser Pro Ser Leu Ser Ser Ser Val Gln Gly Gln Gly
 10                  15                  20 cct gtg acc atg gaa gca gag aga agc aag gcc aca gcc gtg gcc ctg       148
Pro Val Thr Met Glu Ala Glu Arg Ser Lys Ala Thr Ala Val Ala Leu
 25                  30                  35                  40 ggc agt ttc ccg gca ggt ggc ccg gcc gag ctg tcg ctg aga ctc ggg       196
Gly Ser Phe Pro Ala Gly Gly Pro Ala Glu Leu Ser Leu Arg Leu Gly
                 45                  50                  55 gag cca ttg acc atc gtc tct gag gat gga gac tgg tgg acg gtg ctg       244
Glu Pro Leu Thr Ile Val Ser Glu Asp Gly Asp Trp Trp Thr Val Leu
             60                  65                  70 tct gaa gtc tca ggc aga gag tat aac atc ccc agc gtc cac gtg gcc       292
Ser Glu Val Ser Gly Arg Glu Tyr Asn Ile Pro Ser Val His Val Ala
         75                  80                  85 aaa gtc tcc cat ggg tgg ctg tat gag ggc ctg agc agg gag aaa gca       340
Lys Val Ser His Gly Trp Leu Tyr Glu Gly Leu Ser Arg Glu Lys Ala
     90                  95                 100 gag gaa ctg ctg ttg tta cct ggg aac cct gga ggg gcc ttc ctc atc       388
Glu Glu Leu Leu Leu Leu Pro Gly Asn Pro Gly Gly Ala Phe Leu Ile
105                 110                 115                 120 cgg gag agc cag acc agg aga ggc tct tac tct ctg tca gtc cgc ctc       436
Arg Glu Ser Gln Thr Arg Arg Gly Ser Tyr Ser Leu Ser Val Arg Leu
                125                 130                 135 agc cgc cct gca tcc tgg gac cgg atc aga cac tac agg atc cac tgc       484
Ser Arg Pro Ala Ser Trp Asp Arg Ile Arg His Tyr Arg Ile His Cys
            140                 145                 150 ctt gac aat ggc tgg ctg tac atc tca ccg cgc ctc acc ttc ccc tca       532
Leu Asp Asn Gly Trp Leu Tyr Ile Ser Pro Arg Leu Thr Phe Pro Ser
        155                 160                 165 ctc cag gcc ctg gtg gac cat tac tct gag ctg gcg gat gac atc tgc       580
Leu Gln Ala Leu Val Asp His Tyr Ser Glu Leu Ala Asp Asp Ile Cys
    170                 175                 180 tgc cta ctc aag gag ccc tgt gtc ctg cag agg gct ggc ccg ctc cct       628
Cys Leu Leu Lys Glu Pro Cys Val Leu Gln Arg Ala Gly Pro Leu Pro
185                 190                 195                 200 ggc aag gat ata ccc cta cct gtg act gtg cag agg aca cca ctc aac       676
Gly Lys Asp Ile Pro Leu Pro Val Thr Val Gln Arg Thr Pro Leu Asn
                205                 210                 215 tgg aaa gag ctg gac aga tgc tgc atg tac tgt gct atg gac cac gca       724
Trp Lys Glu Leu Asp Arg Cys Cys Met Tyr Cys Ala Met Asp His Ala
            220                 225                 230 cat aca gcc atg ctg ttt cag aag act tgaaatgcca ttgatagttt            771
His Thr Ala Met Leu Phe Gln Lys Thr
        235                 240 aaaaactcta cacccgatgg agaatcgagg aagacaattt aatgtttcat ctgaatccag    831
aggtgcatca aattaaatga cagctccact tggcaaaaaa aaaaaaaaaa aaaaaaaaaa    891
aaaaaaaaaa aaaaaaaaaa aaaaaaa                                       919
```

<210> SEQ ID NO 2
<211> LENGTH: 241
<212> TYPE: PRT

<213> ORGANISM: Homo sapiens

<400> SEQUENCE: 2

```
Met Gly Ser Leu Pro Ser Arg Arg Lys Ser Leu Pro Ser Pro Ser Leu
1               5                   10                  15

Ser Ser Ser Val Gln Gly Gln Gly Pro Val Thr Met Glu Ala Glu Arg
            20                  25                  30

Ser Lys Ala Thr Ala Val Ala Leu Gly Ser Phe Pro Ala Gly Gly Pro
        35                  40                  45

Ala Glu Leu Ser Leu Arg Leu Gly Glu Pro Leu Thr Ile Val Ser Glu
    50                  55                  60

Asp Gly Asp Trp Trp Thr Val Leu Ser Glu Val Ser Gly Arg Glu Tyr
65                  70                  75                  80

Asn Ile Pro Ser Val His Val Ala Lys Val Ser His Gly Trp Leu Tyr
                85                  90                  95

Glu Gly Leu Ser Arg Glu Lys Ala Glu Glu Leu Leu Leu Leu Pro Gly
            100                 105                 110

Asn Pro Gly Gly Ala Phe Leu Ile Arg Glu Ser Gln Thr Arg Arg Gly
        115                 120                 125

Ser Tyr Ser Leu Ser Val Arg Leu Ser Arg Pro Ala Ser Trp Asp Arg
130                 135                 140

Ile Arg His Tyr Arg Ile His Cys Leu Asp Asn Gly Trp Leu Tyr Ile
145                 150                 155                 160

Ser Pro Arg Leu Thr Phe Pro Ser Leu Gln Ala Leu Val Asp His Tyr
                165                 170                 175

Ser Glu Leu Ala Asp Asp Ile Cys Cys Leu Leu Lys Glu Pro Cys Val
            180                 185                 190

Leu Gln Arg Ala Gly Pro Leu Pro Gly Lys Asp Ile Pro Leu Pro Val
        195                 200                 205

Thr Val Gln Arg Thr Pro Leu Asn Trp Lys Glu Leu Asp Arg Cys Cys
    210                 215                 220

Met Tyr Cys Ala Met Asp His Ala His Thr Ala Met Leu Phe Gln Lys
225                 230                 235                 240

Thr
```

<210> SEQ ID NO 3
<211> LENGTH: 1456
<212> TYPE: DNA
<213> ORGANISM: Homo sapiens
<220> FEATURE:
<221> NAME/KEY: CDS
<222> LOCATION: (274)..(936)

<400> SEQUENCE: 3

```
gggcagctga tccatccctg gtgtacaaac tgctgactgc agacagatgc tgagctaccc        60
aaaccaacac ctagcctctc cctgaagatc ctcccaggct gagagagttc tgggtgtcct       120
aggaccaagg acactggcag acttccagaa gggcccccaa agccctaacc tgtccagcca       180
gagcatgcgt ctcagcagag ctgtcttccc aagcctttga tgacaaacca atttccctcg       240
atgatgtgct tctgagtgct gctgagga aca atg gga agt ctg ccc agc aga           294
                                 Met Gly Ser Leu Pro Ser Arg
                                 1               5 aga aaa tct ctg cca agc cca agc ttg agt tcc tct gtc caa ggc cag          342
Arg Lys Ser Leu Pro Ser Pro Ser Leu Ser Ser Ser Val Gln Gly Gln
        10                  15                  20 gga cct gtg acc atg gaa gca gag aga agc aag gcc aca gcc gtg gcc          390
```

```
                Gly Pro Val Thr Met Glu Ala Glu Arg Ser Lys Ala Thr Ala Val Ala
                            25                  30                  35 ctg ggc agt ttc ccg gca ggt ggc ccg gcc gag ctg tcg ctg aga ctc        438
Leu Gly Ser Phe Pro Ala Gly Gly Pro Ala Glu Leu Ser Leu Arg Leu
 40                  45                  50                  55 ggg gag cca ttg acc atc gtc tct gag gat gga gac tgg tgg acg gtg        486
Gly Glu Pro Leu Thr Ile Val Ser Glu Asp Gly Asp Trp Trp Thr Val
                 60                  65                  70 ctg tct gaa gtc tca ggc aga gag tat aac atc ccc agc gtc cac gtg        534
Leu Ser Glu Val Ser Gly Arg Glu Tyr Asn Ile Pro Ser Val His Val
             75                  80                  85 gcc aaa gtc tcc cat ggg tgg ctg tat gag ggc ctg agc agg gag aaa        582
Ala Lys Val Ser His Gly Trp Leu Tyr Glu Gly Leu Ser Arg Glu Lys
         90                  95                 100 gca gag gaa ctg ctg ttg tta cct ggg aac cct gga ggg gcc ttc ctc        630
Ala Glu Glu Leu Leu Leu Leu Pro Gly Asn Pro Gly Gly Ala Phe Leu
    105                 110                 115 atc cgg gag agc cag acc agg aga ggc tct tac tct ctg tca gtc cgc        678
Ile Arg Glu Ser Gln Thr Arg Arg Gly Ser Tyr Ser Leu Ser Val Arg
120                 125                 130                 135 ctc agc cgc cct gca tcc tgg gac cgg atc aga cac tac agg atc cac        726
Leu Ser Arg Pro Ala Ser Trp Asp Arg Ile Arg His Tyr Arg Ile His
                140                 145                 150 tgc ctt gac aat ggc tgg ctg tac atc tca ccg cgc ctc acc ttc ccc        774
Cys Leu Asp Asn Gly Trp Leu Tyr Ile Ser Pro Arg Leu Thr Phe Pro
            155                 160                 165 tca ctc cag gcc ctg gtg gac cat tac tct gag ggc tgg ccc gct ccc        822
Ser Leu Gln Ala Leu Val Asp His Tyr Ser Glu Gly Trp Pro Ala Pro
        170                 175                 180 tgg caa gga tat acc cct acc tgt gac tgt gca gag gac acc act caa        870
Trp Gln Gly Tyr Thr Pro Thr Cys Asp Cys Ala Glu Asp Thr Thr Gln
    185                 190                 195 ctg gaa aga gct gga cag gaa ctt cag gaa gga aaa tcc act tcg gca        918
Leu Glu Arg Ala Gly Gln Glu Leu Gln Glu Gly Lys Ser Thr Ser Ala
200                 205                 210                 215 gcc cag aaa acc aag aaa tgactgcaaa tataatacgc ttttcaagct              966
Ala Gln Lys Thr Lys Lys
                220 acctggaatc aagctgtttg tgatggcccc ttccagatca tggagcagag ttacgaagca    1026 tcctccgaat gggacgagta agaacgttct gaagtcccaa ccaattctcg cacatatctg    1086 gtggcgtttc tccaccccca cacctcacac tcacccagcg ggtggtctca gtctcccctc    1146 ttgactcatg cttatcaaag tattcggtcc tttacattca acaagcaaca gcagctcaag    1206 attagcgagc tcactatgt gcaaaaggct ttaatgtacc acagtacccc acttcagagt     1266 tattctgagt taaacgagat tccgcttgca gagcacctgg cacgtagaaa gcattctcag    1326 cagaagtctg ttactgttaa tgtttgtgct acttaattcg aaagaaacaa gtaacctact    1386 caaaacccta ctgcacataa aaggcggagg ccgaatcgaa aaaaaaaaa aaaaaaaaa      1446 aaaaaaaag                                                             1456

<210> SEQ ID NO 4
<211> LENGTH: 221
<212> TYPE: PRT
<213> ORGANISM: Homo sapiens

<400> SEQUENCE: 4

Met Gly Ser Leu Pro Ser Arg Arg Lys Ser Leu Pro Pro Ser Leu
 1               5                  10                  15
```

Ser Ser Ser Val Gln Gly Gln Gly Pro Val Thr Met Glu Ala Glu Arg
                20                  25                  30

Ser Lys Ala Thr Ala Val Ala Leu Gly Ser Phe Pro Ala Gly Gly Pro
            35                  40                  45

Ala Glu Leu Ser Leu Arg Leu Gly Glu Pro Leu Thr Ile Val Ser Glu
    50                  55                  60

Asp Gly Asp Trp Trp Thr Val Leu Ser Glu Val Ser Gly Arg Glu Tyr
65                  70                  75                  80

Asn Ile Pro Ser Val His Val Ala Lys Val Ser His Gly Trp Leu Tyr
                85                  90                  95

Glu Gly Leu Ser Arg Glu Lys Ala Glu Leu Leu Leu Leu Pro Gly
            100                 105                 110

Asn Pro Gly Gly Ala Phe Leu Ile Arg Glu Ser Gln Thr Arg Arg Gly
            115                 120                 125

Ser Tyr Ser Leu Ser Val Arg Leu Ser Arg Pro Ala Ser Trp Asp Arg
    130                 135                 140

Ile Arg His Tyr Arg Ile His Cys Leu Asp Asn Gly Trp Leu Tyr Ile
145                 150                 155                 160

Ser Pro Arg Leu Thr Phe Pro Ser Leu Gln Ala Leu Val Asp His Tyr
                165                 170                 175

Ser Glu Gly Trp Pro Ala Pro Trp Gln Gly Tyr Thr Pro Thr Cys Asp
            180                 185                 190

Cys Ala Glu Asp Thr Thr Gln Leu Glu Arg Ala Gly Gln Glu Leu Gln
            195                 200                 205

Glu Gly Lys Ser Thr Ser Ala Ala Gln Lys Thr Lys Lys
    210                 215                 220

<210> SEQ ID NO 5
<211> LENGTH: 252
<212> TYPE: DNA
<213> ORGANISM: Homo sapiens

<400> SEQUENCE: 5
aggtggctgt atgagggcct gagcagggag aaagcagagg aactgctgtt gttacctggg      60
aaccctggag gggccttcct catccgggag agccagacca ggagaggctc ttactctctg     120
tcagtccgcc tcagccgccc tgcatcctgg accggatca gacactacag gatccactgc      180
cttgacaatg gctggctgta catctcaccg cgcctcacct tccctcact ccaggccctg      240 gtggaccatt ac                                                         252

<210> SEQ ID NO 6
<211> LENGTH: 84
<212> TYPE: PRT
<213> ORGANISM: Homo sapiens

<400> SEQUENCE: 6

Arg Trp Leu Tyr Glu Gly Leu Ser Arg Glu Lys Ala Glu Glu Leu Leu
1               5                   10                  15

Leu Leu Pro Gly Asn Pro Gly Gly Ala Phe Leu Ile Arg Glu Ser Gln
            20                  25                  30

Thr Arg Arg Gly Ser Tyr Ser Leu Ser Val Arg Leu Ser Arg Pro Ala
        35                  40                  45

Ser Trp Asp Arg Ile Arg His Tyr Arg Ile His Cys Leu Asp Asn Gly
    50                  55                  60

Trp Leu Tyr Ile Ser Pro Arg Leu Thr Phe Pro Ser Leu Gln Ala Leu 65          70          75          80
Val Asp His Tyr

<210> SEQ ID NO 7
<211> LENGTH: 261
<212> TYPE: PRT
<213> ORGANISM: Homo sapiens

<400> SEQUENCE: 7

Met Gly Ser Leu Pro Ser Arg Arg Lys Ser Leu Pro Ser Pro Ser Leu
1               5                   10                  15

Ser Ser Ser Val Gln Gly Gln Gly Pro Val Thr Met Glu Ala Glu Arg
            20                  25                  30

Ser Lys Ala Thr Ala Val Ala Leu Gly Ser Phe Pro Ala Gly Gly Pro
        35                  40                  45

Ala Glu Leu Ser Leu Arg Leu Gly Glu Pro Leu Thr Ile Val Ser Glu
    50                  55                  60

Asp Gly Asp Trp Trp Thr Val Leu Ser Glu Val Ser Gly Arg Glu Tyr
65                  70                  75                  80

Asn Ile Pro Ser Val His Val Ala Lys Val Ser His Gly Trp Leu Tyr
                85                  90                  95

Glu Gly Leu Ser Arg Glu Lys Ala Glu Glu Leu Leu Leu Leu Pro Gly
            100                 105                 110

Asn Pro Gly Gly Ala Phe Leu Ile Arg Glu Ser Gln Thr Arg Arg Gly
        115                 120                 125

Ser Tyr Ser Leu Ser Val Arg Leu Ser Arg Pro Ala Ser Trp Asp Arg
    130                 135                 140

Ile Arg His Tyr Arg Ile His Cys Leu Asp Asn Gly Trp Leu Tyr Ile
145                 150                 155                 160

Ser Pro Arg Leu Thr Phe Pro Ser Leu Gln Ala Leu Val Asp His Tyr
                165                 170                 175

Ser Glu Leu Ala Asp Asp Ile Cys Cys Leu Leu Lys Glu Pro Cys Val
            180                 185                 190

Leu Gln Arg Ala Gly Pro Leu Pro Gly Lys Asp Ile Pro Leu Pro Val
        195                 200                 205

Thr Val Gln Arg Thr Pro Leu Asn Trp Lys Glu Leu Asp Ser Ser Leu
    210                 215                 220

Leu Phe Ser Glu Ala Ala Thr Gly Glu Glu Ser Leu Leu Ser Glu Gly
225                 230                 235                 240

Leu Arg Glu Ser Leu Ser Phe Tyr Ile Ser Leu Asn Asp Glu Ala Val
                245                 250                 255

Ser Leu Asp Asp Ala
            260

<210> SEQ ID NO 8
<211> LENGTH: 80
<212> TYPE: DNA
<213> ORGANISM: Homo sapiens

<400> SEQUENCE: 8
aggatgcagg gcggctgagg cggactgaca gagagtaaga gcctctcctg gtctggctct    60
cccggatgag gaaggccccct                                              80

<210> SEQ ID NO 9
<211> LENGTH: 20
<212> TYPE: DNA

<213> ORGANISM: Bacteriophage T7

<400> SEQUENCE: 9
taatacgact cactataggg          20

<210> SEQ ID NO 10
<211> LENGTH: 18
<212> TYPE: DNA
<213> ORGANISM: Bacteriophage SP6

<400> SEQUENCE: 10
atttaggtga cactatag          18

<210> SEQ ID NO 11
<211> LENGTH: 18
<212> TYPE: DNA
<213> ORGANISM: Homo sapiens

<400> SEQUENCE: 11
aggtggctgt atgagggc          18

<210> SEQ ID NO 12
<211> LENGTH: 19
<212> TYPE: DNA
<213> ORGANISM: Homo sapiens

<400> SEQUENCE: 12
tctcctggtc tggctctcc          19

<210> SEQ ID NO 13
<211> LENGTH: 733
<212> TYPE: DNA
<213> ORGANISM: Homo sapiens

<400> SEQUENCE: 13
gggatccgga gcccaaatct tctgacaaaa ctcacacatg cccaccgtgc ccagcacctg     60
aattcgaggg tgcaccgtca gtcttcctct tccccccaaa acccaaggac accctcatga    120
tctcccggac tcctgaggtc acatgcgtgg tggtggacgt aagccacgaa gaccctgagg    180
tcaagttcaa ctggtacgtg gacggcgtgg aggtgcataa tgccaagaca aagccgcggg    240
aggagcagta caacagcacg taccgtgtgg tcagcgtcct caccgtcctg caccaggact    300
ggctgaatgg caaggagtac aagtgcaagg tctccaacaa agccctccca acccccatcg    360
agaaaaccat ctccaaagcc aaagggcagc ccgagaacc acaggtgtac accctgcccc     420
catcccggga tgagctgacc aagaaccagg tcagcctgac ctgcctggtc aaaggcttct    480
atccaagcga catcgccgtg gagtgggaga gcaatgggca gccggagaac aactacaaga    540
ccacgcctcc cgtgctggac tccgacggct ccttcttcct ctacagcaag ctcaccgtgg    600
acaagagcag gtggcagcag gggaacgtct tctcatgctc cgtgatgcat gaggctctgc    660
acaaccacta cacgcagaag agcctctccc tgtctccggg taaatgagtg cgacggccgc    720
gactctagag gat         733

<210> SEQ ID NO 14
<211> LENGTH: 210
<212> TYPE: PRT
<213> ORGANISM: Homo sapiens

```
<400> SEQUENCE: 14

Met Gly Ser Leu Pro Ser Arg Arg Lys Ser Leu Pro Ser Pro Ser Leu
1               5                   10                  15

Ser Ser Ser Val Gln Gly Gln Gly Pro Val Thr Met Glu Ala Glu Arg
            20                  25                  30

Ser Lys Ala Thr Ala Val Ala Leu Gly Ser Phe Pro Ala Gly Gly Pro
        35                  40                  45

Ala Glu Leu Ser Leu Arg Leu Gly Glu Pro Leu Thr Ile Val Ser Glu
    50                  55                  60

Asp Gly Asp Trp Trp Thr Val Leu Ser Glu Val Ser Gly Arg Glu Tyr
65                  70                  75                  80

Asn Ile Pro Ser Val His Val Ala Lys Val Ser His Gly Trp Leu Tyr
            85                  90                  95

Glu Gly Leu Ser Arg Glu Lys Ala Glu Glu Leu Leu Leu Leu Pro Gly
            100                 105                 110

Asn Pro Gly Gly Ala Phe Leu Ile Arg Glu Ser Gln Thr Arg Arg Gly
        115                 120                 125

Ser Tyr Ser Leu Ser Val Arg Leu Ser Arg Pro Ala Ser Trp Asp Arg
    130                 135                 140

Ile Arg His Tyr Arg Ile His Cys Leu Asp Asn Gly Trp Leu Tyr Ile
145                 150                 155                 160

Ser Pro Arg Leu Thr Phe Pro Ser Leu Gln Ala Leu Val Asp His Tyr
            165                 170                 175

Ser Glu Gly Trp Pro Ala Pro Trp Gln Gly Tyr Thr Pro Thr Cys Asp
            180                 185                 190

Cys Ala Glu Asp Thr Thr Gln Leu Glu Arg Ala Gly Gln Leu Pro Pro
            195                 200                 205

Val Phe
    210
```